(12) United States Patent
Edmunds et al.

(10) Patent No.: US 12,134,612 B2
(45) Date of Patent: Nov. 5, 2024

(54) PESTICIDALLY ACTIVE POLYCYCLIC DERIVATIVES WITH SULFUR CONTAINING SUBSTITUENTS

(71) Applicant: SYNGENTA PARTICIPATIONS AG, Basel (CH)

(72) Inventors: Andrew Edmunds, Stein (CH); Michel Muehlebach, Stein (CH); Pierre Joseph Marcel Jung, Stein (CH); André Jeanguenat, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 766 days.

(21) Appl. No.: 17/235,321

(22) Filed: Apr. 20, 2021

(65) Prior Publication Data

US 2021/0332039 A1 Oct. 28, 2021

Related U.S. Application Data

(60) Division of application No. 16/201,408, filed on Nov. 27, 2018, now Pat. No. 10,981,907, which is a continuation of application No. 15/541,786, filed as application No. PCT/EP2016/050593 on Jan. 14, 2016, now Pat. No. 10,138,238.

(30) Foreign Application Priority Data

Jan. 19, 2015 (EP) ..................... 15151643

(51) Int. Cl.
*C07D 471/04* (2006.01)
*A01N 43/90* (2006.01)
*C07D 487/04* (2006.01)

(52) U.S. Cl.
CPC ........... *C07D 471/04* (2013.01); *A01N 43/90* (2013.01); *C07D 487/04* (2013.01)

(58) Field of Classification Search
CPC ............................ C07D 471/04; C07D 487/04
See application file for complete search history.

(56) References Cited

U.S. PATENT DOCUMENTS

| | | | |
|---|---|---|---|
| 10,138,238 | B2 | 11/2018 | Edmunds et al. |
| 2014/0194290 | A1 | 7/2014 | Takahashi et al. |
| 2017/0367332 | A1 | 12/2017 | Edmunds et al. |
| 2018/0002345 | A1 | 1/2018 | Fischer et al. |
| 2018/0271099 | A1 | 9/2018 | Fischer et al. |
| 2019/0021329 | A1 | 1/2019 | Wilcke et al. |
| 2019/0150447 | A1 | 5/2019 | Oohira et al. |

FOREIGN PATENT DOCUMENTS

| | | |
|---|---|---|
| CN | 103717598 A | 4/2014 |
| CN | 107428764 A | 12/2017 |
| CN | 108137548 A | 6/2018 |
| CN | 108349973 A | 7/2018 |
| CN | 108779118 A | 11/2018 |
| EP | 2975039 A1 | 1/2016 |
| JP | 2014005263 A | 1/2014 |
| JP | 2014065675 A | 4/2014 |
| JP | 2018505881 A | 3/2018 |
| JP | 2019502713 A | 1/2019 |
| WO | 2013018928 A1 | 2/2013 |
| WO | 2014049889 A1 | 4/2014 |
| WO | 2014142292 A1 | 9/2014 |
| WO | 2015000715 A1 | 1/2015 |
| WO | WO2015121136 A1 * | 8/2015 |
| WO | 2016124563 A1 | 8/2016 |
| WO | 2017082132 A1 | 5/2017 |
| WO | 2017121674 A1 | 7/2017 |

OTHER PUBLICATIONS

IPRP and Written Opinion for PCT/EP2016/050593, mailed Aug. 3, 2017.
Extended European Search Report for EP 15151643.2, mailed Jul. 9, 2015.
International Search Report and Written Opinion for PCT/EP2016/050593, mailed Jun. 28, 2016.

* cited by examiner

*Primary Examiner* — Kamal A Saeed
*Assistant Examiner* — Karen Cheng
(74) *Attorney, Agent, or Firm* — BakerHostetler; Toni-Junell Herbert

(57) ABSTRACT

Polycyclic derivatives of formula I

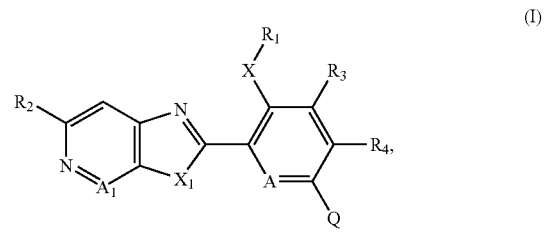

wherein the substituents are as defined in claim 1, and the agrochemically acceptable salts salts, stereoisomers, enantiomers, tautomers and N-oxides of those compounds, can be used as insecticides and can be prepared in a manner known per se.

12 Claims, No Drawings

PESTICIDALLY ACTIVE POLYCYCLIC DERIVATIVES WITH SULFUR CONTAINING SUBSTITUENTS

CROSS REFERENCE TO RELATED APPLICATIONS

This application is a divisional of U.S. patent application Ser. No. 16/201,408, filed Nov. 27, 2018, which is a continuation application of U.S. patent application Ser. No. 15/541,786, filed Jul. 6, 2017, which is a 371 National Stage application of International Application No. PCT/EP2016/050593, filed Jan. 14, 2016, which claims priority to European Patent Application No. 15151643.2, filed Jan. 19, 2015, the entire contents of which are hereby incorporated by reference.

The present invention relates to pesticidally active, in particular insecticidally active polycyclic derivatives containing sulfur substituents, to compositions comprising those compounds, and to their use for controlling animal pests, including arthropods and in particular insects or representatives of the order Acarina.

Heterocyclic compounds with pesticidal action are known and described, for example, in WO 2012/086848, WO 2013/018928, WO 2014/142292, WO 2015/133603, WO2015/000715 and WO 2015/121136 There have now been found novel pesticidally active polycyclic ring derivatives with sulphur containing phenyl and pyridyl substituents.

The present invention accordingly relates to compounds of formula I,

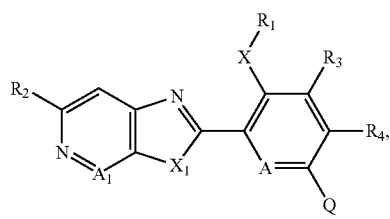

(I)

wherein
A represents CH, N or the N-oxide;
$A_1$ is CH, N or the N-oxide;
Q is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur,
with the proviso that each ring system cannot contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulfur, with the proviso that said ring system cannot contain more than one oxygen atom and more than one sulfur atom; or
Q is $C_3$-$C_6$cycloalkyl, or $C_3$-$C_6$cycloalkyl mono- or polysubstituted by substituents selected from the group consisting of halogen, cyano, $CONH_2$, carboxyl, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl; or
Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl; or
Q is $C_1$-$C_6$alkyl, or $C_1$-$C_6$alkyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl;
X is S, SO or $SO_2$;
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_1$ is $C_3$-$C_6$cycloalkyl-$C_1$-$C_4$alkyl mono- or polysubstituted by substituents selected from the group consisting of halogen, cyano and $C_1$-$C_4$alkyl; or
$R_1$ is $C_2$-$C_6$alkenyl, $C_2$-$C_6$haloalkenyl or $C_2$-$C_6$alkynyl;
$R_2$ is halogen, cyano, $C_1$-$C_6$haloalkyl or $C_1$-$C_6$haloalkyl substituted by one or two substituents selected from the group consisting of hydroxyl, methoxy and cyano; or $R_2$ is $C_1$-$C_4$haloalkylsulfanyl, $C_1$-$C_4$haloalkylsulfinyl, $C_1$-$C_4$haloalkylsulfonyl, $O(C_1$-$C_4$haloalkyl), or —C(O) $C_1$-$C_4$haloalkyl; or $R_2$ is $C_3$-$C_6$cycloalkyl which can be mono- or polysubstituted by substituents selected from the group consisting of halogen, cyano and $C_1$-$C_4$alkyl;

$X_1$ is $NR_5$; wherein $R_5$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl; or $X_1$ is oxygen or sulfur;

$R_3$ is hydrogen or $C_1$-$C_2$-alkyl;

$R_4$ is hydrogen, halogen or $C_1$-$C_3$haloalkyl;

and agrochemically acceptable salts, stereoisomers, enantiomers, tautomers of the compounds of formula I.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated. $C_1$-di-alkylamino is dimethylamino.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

Haloalkylsulfanyl is for example trifluoromethylsulfanyl, 2,2,2-trifluoroethylsulfanyl, and pentafluoroethylsulfanyl.

Haloalkylsulfinyl is for example trifluoromethylsulfinyl, 2,2,2-trifluoroethylsulfinyl, or pentafluoroethylsulfinyl.

Haloalkylsulfonyl is for example trifluoromethylsulfonyl, 2,2,2-trifluoroethylsulfonyl, and pentafluoroethylsulfonyl.

Cycloalkyl is, for example, cyclopropyl, cyclobutyl, cyclopentyl and cyclohexyl.

In the context of this invention, examples of a five- to six-membered, aromatic, partially saturated or fully saturated ring system that are linked via a nitrogen atom to the ring which contains the group A, are for example, pyrazole, pyrrole, pyrrolidine, pyrrolidine-2-one, piperidine, morpholine, imidazole, triazole and pyridine-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

The compounds of formula I according to the invention also include hydrates which may be formed during the salt formation.

According to the present invention, a five- to ten-membered monocyclic or fused bicyclic hetero-ring system which can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms or a three- to ten-membered, monocyclic or fused bicyclic ring system which may be aromatic, partially saturated or fully saturated is, depending of the number of ring members, preferably selected from the group consisting of the following heterocyclic groups:

pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl, pyranyl; quinazolinyl; isoquinolinyl; indolizinyl; isobenzofuranylnaphthyridinyl; quinoxalinyl; cinnolinyl; phthalazinyl; benzothiazolyl; benzoxazolyl; benzotriazolyl; indazolyl; indolyl; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3-yl)-; (1H-pyrazol-4-yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H-imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-; (1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-thiadiazol-4-yl)-; (1,3,4-thiadiazol-5-yl)-; (1H-tetrazol-1- yl)-; (1H-tetrazol-5-yl)-; (2H-tetrazol-5-yl)-; (2-pyridyl)-; (3-pyridyl)-; (4-pyridyl)-; (2-pyrimidinyl)-; (4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; (1,2,4-triazin-3-yl)-; (furazan-3-yl)-; (2-quinolinyl)-; (3-quinolinyl)-; (4-quinolinyl)-; (5-quinolinyl)-; (6-quinolinyl)-; (3-isoquinolnyl)-; (4-isoquinolnyl)-; (2-quinozolinyl)-; (2-quinoxalinyl)-; (5-quinoxalinyl)-; (pyrido[2,3-b]pyrazin-7-yl)-; (benzoxazol-5-yl)-; (benzothiazol-5-yl)-; (benzo[b]thien-2-yl)- and (benzo[1,2,5]oxadiazol-5-yl)-; indolinyl and tetrahydroquinolynyl.

In preferred compounds of formula I, Q is selected from the group consisting of J-0 to J-50:

J-10
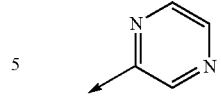

J-11
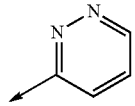

J-12
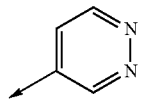

J-13
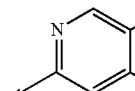

J-14
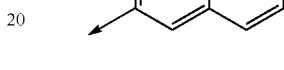

J-15
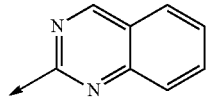

J-16
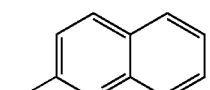

J-17
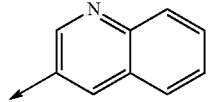

J-18
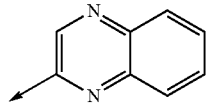

J-19
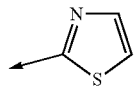

J-20
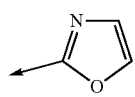

J-21
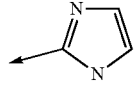

J-22
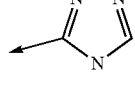

J-23
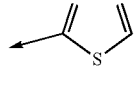

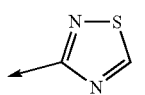
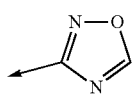
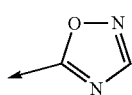
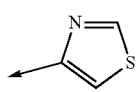
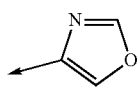
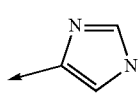
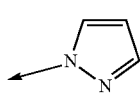
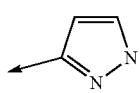
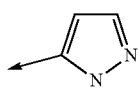
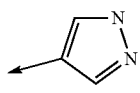
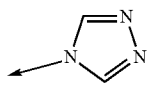
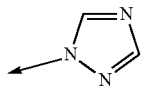
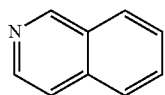
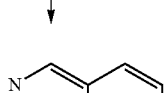
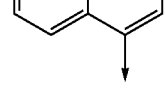
J-24
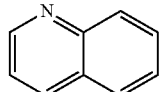
J-25
J-26
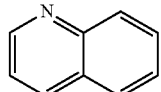
J-27
J-28
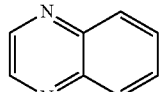
J-29
J-30
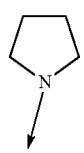
J-31
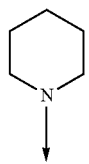
J-32
J-33
J-34
J-35
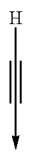
J-36
J-37
J-38
J-39
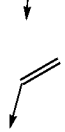
J-40
J-41
J-42
J-43
J-44
J-45
J-46
J-47

-continued

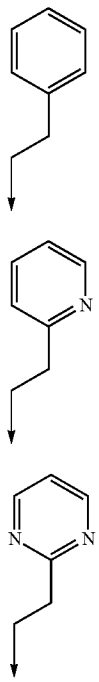

J-48

J-49

J-50 wherein each group J-0 to J-50 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

A preferred group of compounds of formula I is represented by the compounds of formula I-1

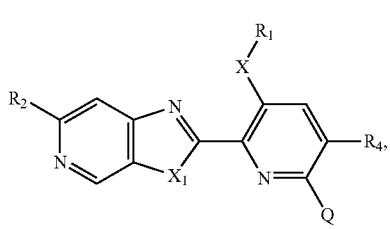

(I-1)

wherein $R_2$, $R_4$, A, X and Q are as defined under formula I above; and wherein $R_1$ is methyl, ethyl, n-propyl, i-propyl or cyclopropylmethyl; $R_4$ is hydrogen, halogen or $C_1$-$C_3$haloalkyl; $X_1$ is N-methyl, oxygen or sulfur; and agrochemically acceptable salts, stereoisomers, enantiomers, tautomers and N-oxides of the compounds of formula I-1.

In said preferred group of compounds of formula I-1, $R_2$ is preferably $C_1$-$C_4$haloalkyl, halogen, $C_1$-$C_4$haloalkylsulfanyl, $C_1$-$C_4$haloalkylsulfinyl or $C_1$-$C_4$haloalkylsulfonyl; X is $SO_2$; $R_1$ is preferably ethyl; $X_1$ is preferably N-methyl; and $R_4$ is preferably hydrogen or $C_1$-$C_2$haloalkyl.

In said preferred group of compounds of formula I-1, Q is selected from the group consisting of J-0 to J-50 (where the arrow represents the point of attachment of the heterocycle to the radical Q):

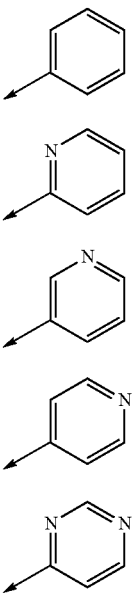

J-0

J-1

J-2

J-3

J-4

J-5

J-6

J-7

J-8

J-9

J-10

J-11

J-12

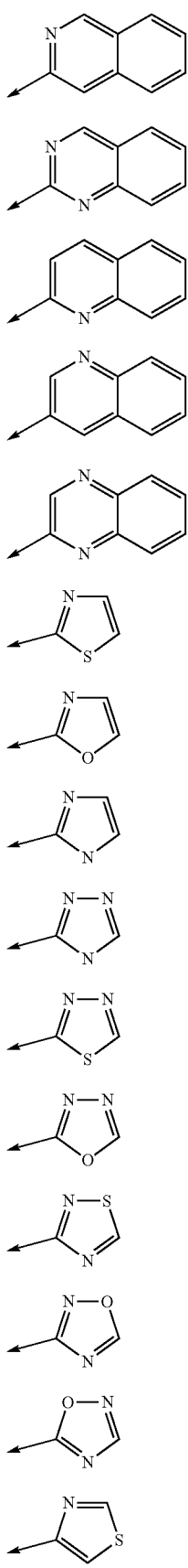
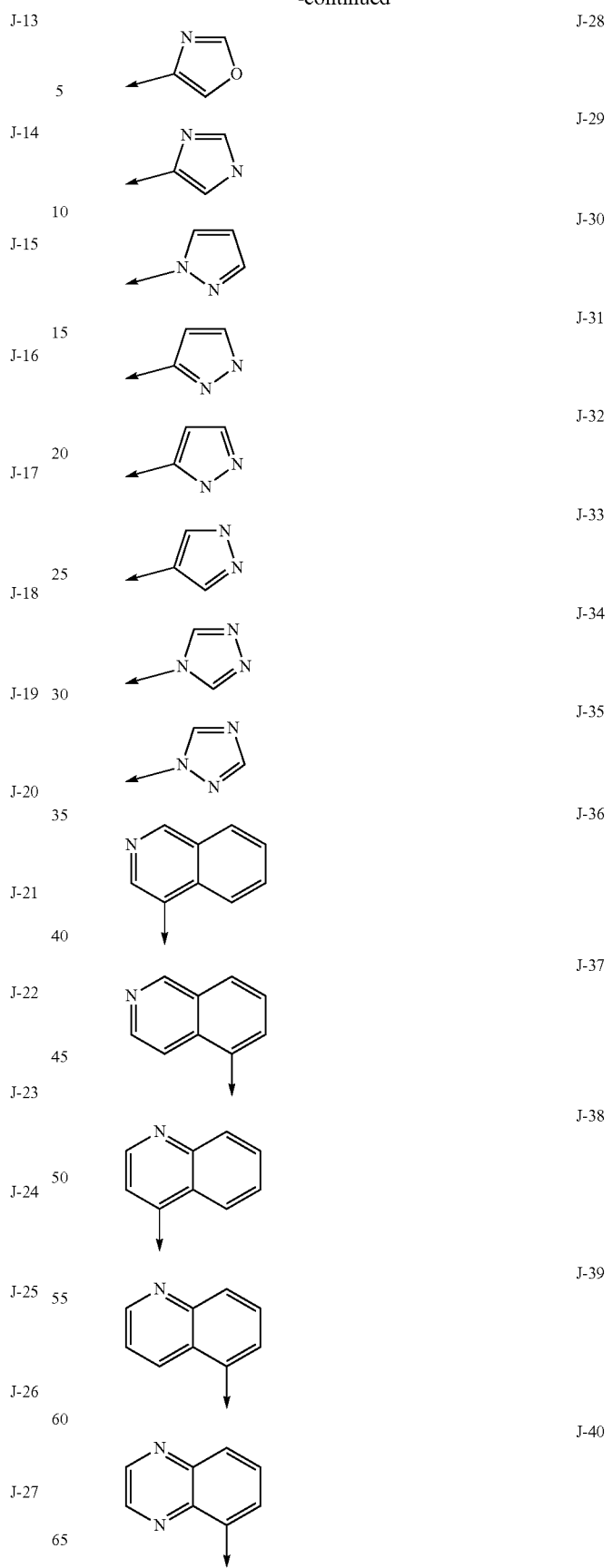

J-41 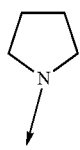

J-42 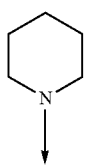

J-43 

J-44 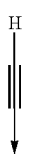

J-45 

J-46 

J-47 

J-48 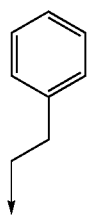

J-49 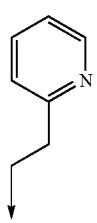

J-50 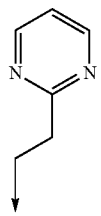

wherein each group J-0 to J-50 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

Further preferred compounds of formula I are represented by the compounds of formula I-2

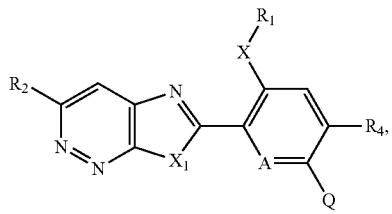 (I-2)

wherein $R_2$, $R_4$, A, X and Q are as defined under formula I above; and wherein $R_1$ is methyl, ethyl, n-propyl, i-propyl or cyclopropylmethyl; $R_4$ is hydrogen, halogen or $C_1$-$C_3$haloalkyl; $X_1$ is N-methyl, oxygen or sulfur; and agrochemically acceptable salts, stereoisomers, enantiomers, tautomers and N-oxides of the compounds of formula I-2.

In said preferred group of compounds of formula I-2, $R_2$ is preferably $C_1$-$C_4$haloalkyl, halogen, $C_1$-$C_4$haloalkylsulfanyl, $C_1$-$C_4$haloalkylsulfinyl or $C_1$-$C_4$haloalkylsulfonyl; X is $SO_2$; $R_1$ is preferably ethyl; $X_1$ is preferably N-methyl; and $R_4$ is preferably hydrogen or $C_1$-$C_2$haloalkyl.

In said preferred group of compounds of formula I-2, Q is selected from the group consisting of J-0 to J-50 (where the arrow represents the point of attachment of the heterocycle to the radical Q):

J-0 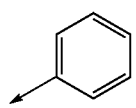

J-1 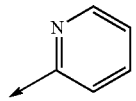

J-2 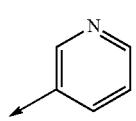

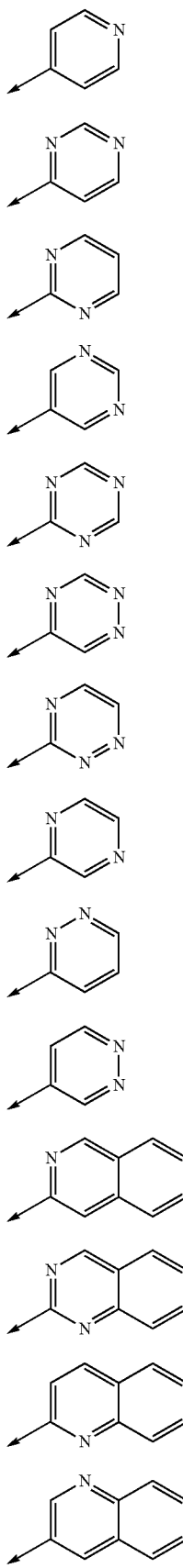
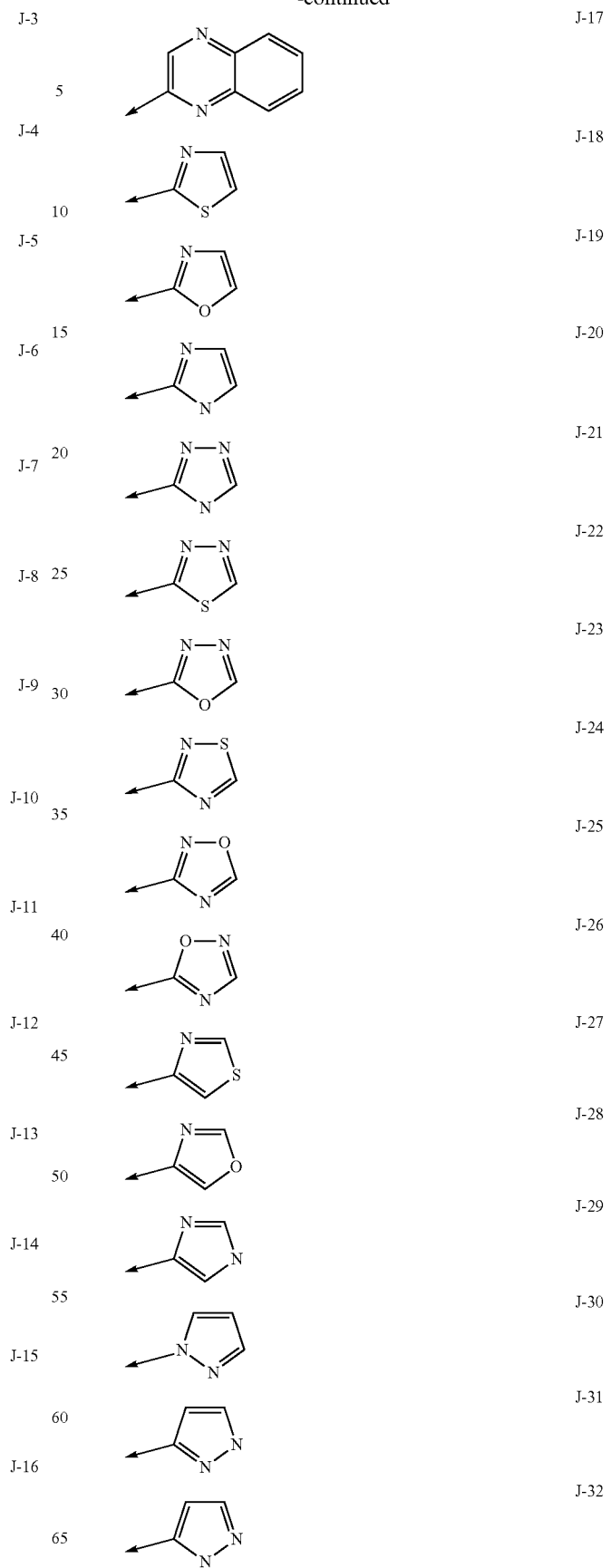

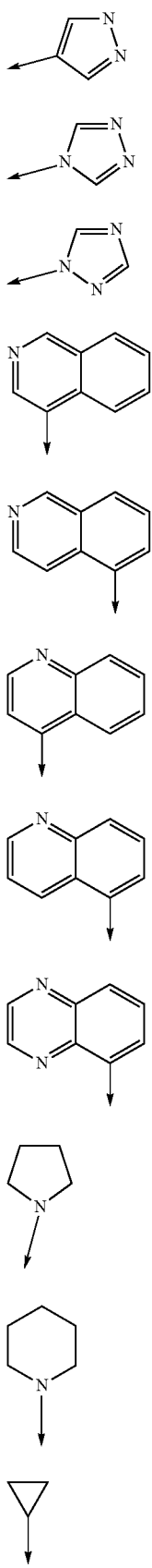
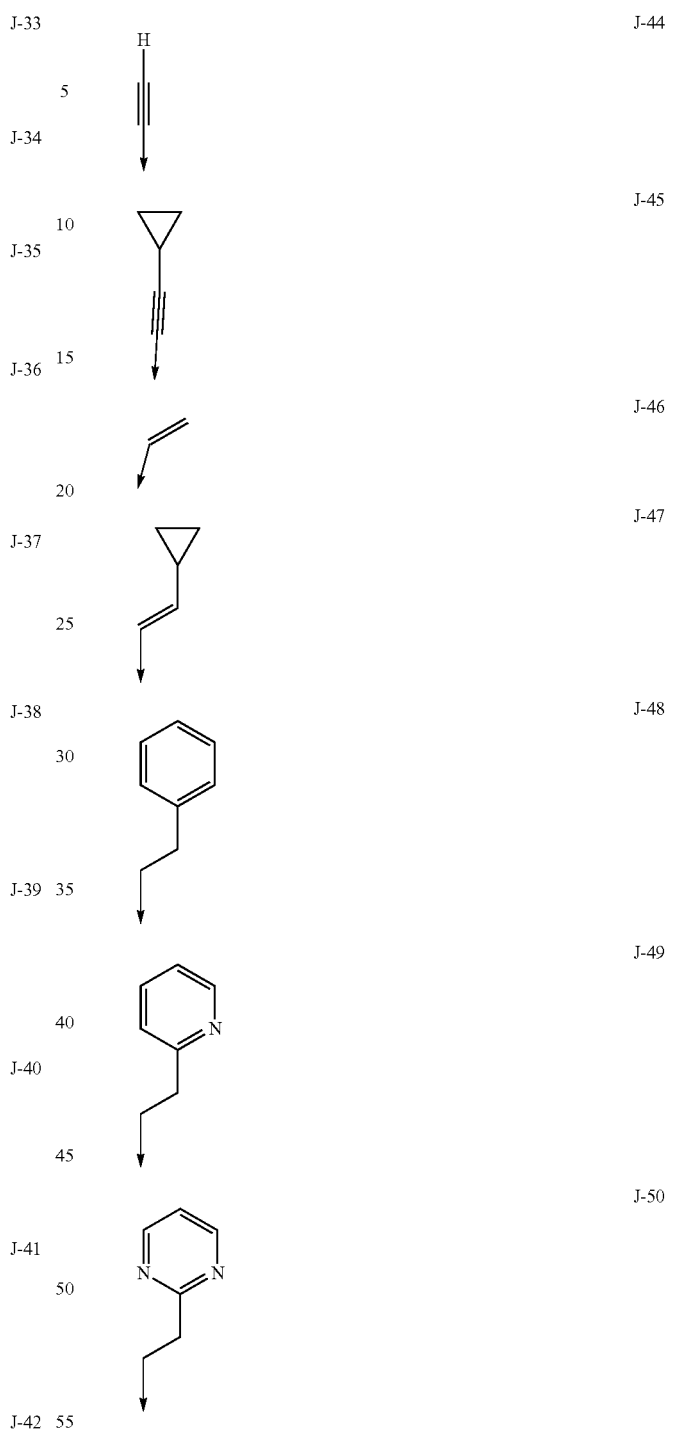

wherein each group J-0 to J-50 is mono- di- or trisubstituted with Rx, wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

In particular preferred compounds of formula I-1 are those of formula I-1a

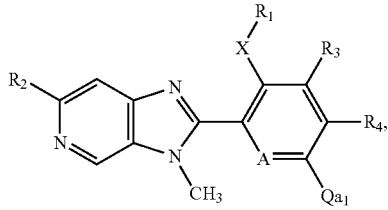
(I-1a)

wherein
A is N or CH;
X is S or $SO_2$;
$R_1$ is $C_1$-$C_4$alkyl;
$R_2$ is $C_1$-$C_4$haloalkyl, $C_1$-$C_4$haloalkylsulfanyl, $C_1$-$C_4$haloalkylsulfinyl or $C_1$-$C_4$haloalkylsulfonyl;
$R_4$ is hydrogen or $C_1$-$C_2$haloalkyl;
$Q_{a1}$ is selected from the group consisting of the substituents

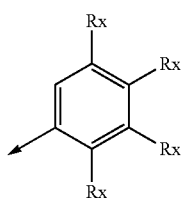
J-0

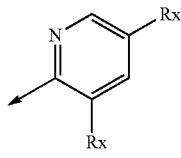
J-1

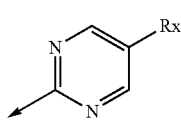
J-5

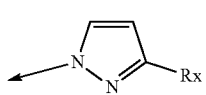
J-30

J-43

J-44

J-46

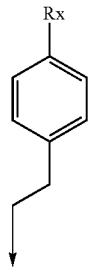
J-48

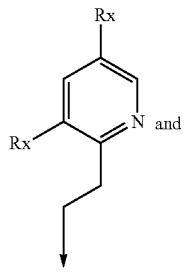
J-49

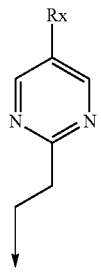
J-50 wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

More preferred compounds of formula I-1a are those, in which each Rx is, independently from each other, selected from hydrogen, halogen, $C_1$-$C_4$alkyl and $C_1$-$C_4$haloalkyl.

An especially preferred group of compounds of formula I-1a are represented by the compounds of formula I-1a2

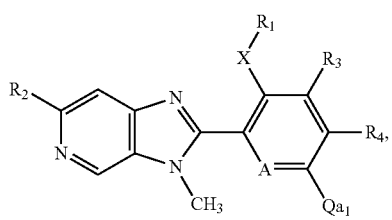
(I-1a2)

wherein
A is N or CH;
$R_2$ is $C_1$-$C_2$haloalkyl, $C_1$-$C_2$haloalkylsulfanyl, $C_1$-$C_2$haloalkylsulfinyl or $C_1$-$C_2$haloalkylsulfonyl;
$R_4$ is hydrogen or $C_1$-$C_2$haloalkyl;
and $Q_{a1}$ is selected from the group consisting of the substituents

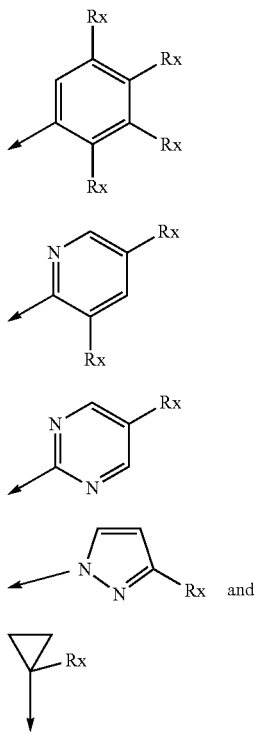

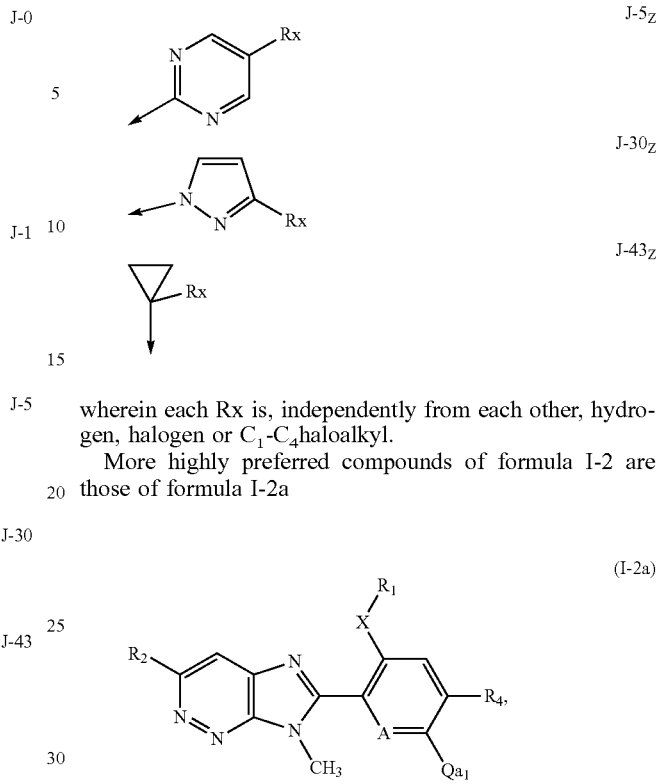

wherein each Rx is, independently from each other, hydrogen, halogen or $C_1$-$C_4$haloalkyl.

More highly preferred compounds of formula I-2 are those of formula I-2a (I-2a)

wherein
- A is N or CH;
- X is S or $SO_2$;
- $R_1$ is $C_1$-$C_4$alkyl;
- $R_2$ is $C_1$-$C_4$haloalkyl, $C_1$-$C_4$haloalkylsulfanyl, $C_1$-$C_4$haloalkylsulfinyl or $C_1$-$C_4$haloalkylsulfonyl;
- $R_4$ is hydrogen or $C_1$-$C_2$haloalkyl;
- $Q_{a1}$ is preferably selected from the group consisting of the substituents wherein each Rx, independently from each other, is hydrogen, halogen, $C_1$-$C_4$alkyl or $C_1$-$C_4$haloalkyl.

In said preferred compounds of formula I-1a2, Rx is, independently from each other, preferably halogen, hydrogen or $C_1$-$C_4$haloalkyl; $R_1$ is preferably ethyl; and $R_4$ is preferably hydrogen.

In particular preferred compounds of formula I-1a2 are those, in which $Q_{a1}$ is selected from J-0z1, J-0z2, J0z3, J-1z, J-5z, J-30z and J-43z;

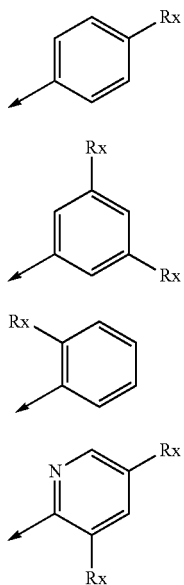

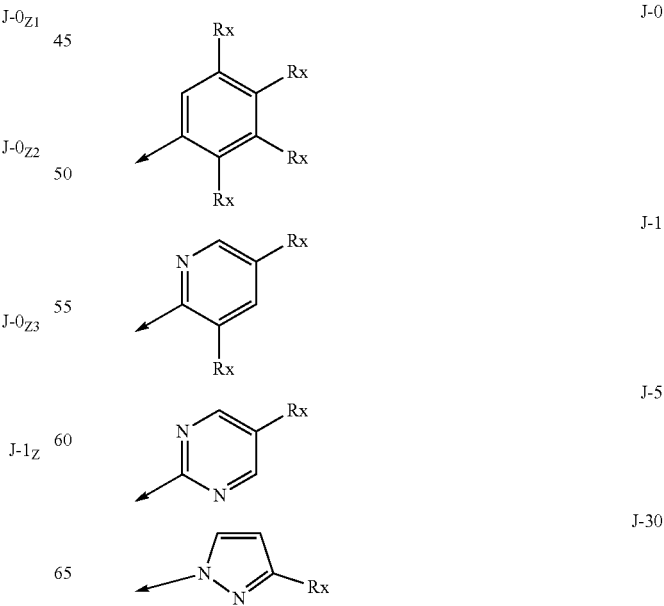

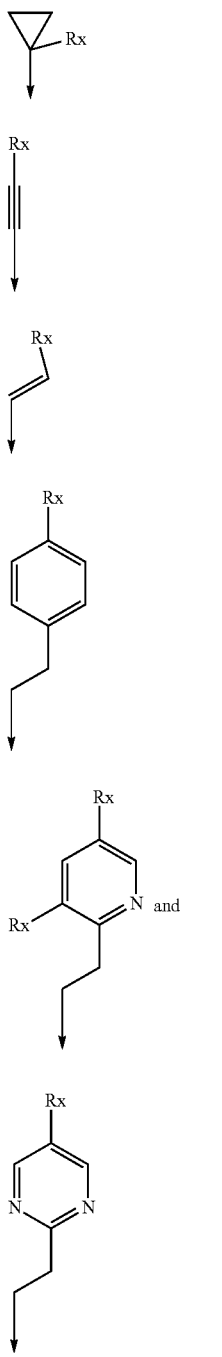

wherein each Rx is, independently from each other, selected from hydrogen, halogen, cyano, C$_1$-C$_4$alkyl, C$_1$-C$_4$haloalkyl, C$_1$-C$_4$haloalkoxy, C$_1$-C$_4$alkoxy, C$_1$-C$_4$alkylsulfanyl, C$_1$-C$_4$alkylsulfinyl, C$_1$-C$_4$alkylsulfonyl, —C(O)C$_1$-C$_4$alkyl, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl.

More preferred compounds of formula I-2a, are those in which each Rx is, independently from each other, selected from, hydrogen, halogen, C$_1$-C$_4$alkyl, and C$_1$-C$_4$haloalkyl;

An especially preferred group of compounds of formula I-2a is represented by the compounds of formula I-2a2

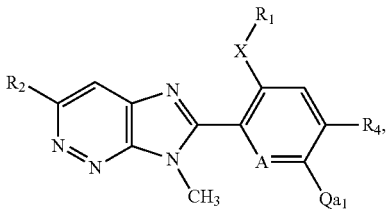

wherein
A is N or CH;
R$_2$ is C$_1$-C$_2$haloalkyl, C$_1$-C$_2$haloalkylsulfanyl, C$_1$-C$_2$haloalkylsulfinyl or C$_1$-C$_2$haloalkylsulfonyl;
R$_4$ is hydrogen or C$_1$-C$_2$haloalkyl;
and Q$_{a1}$ is selected from the group of the substituents;

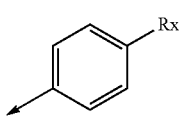

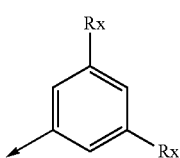

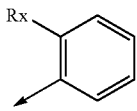

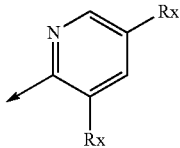

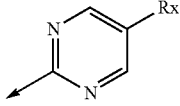

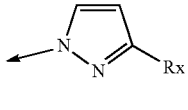

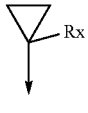

wherein each Rx is, independently from each other, hydrogen, halogen, C$_1$-C$_4$alkyl or C$_1$-C$_4$haloalkyl.

In said preferred compounds of formula I-2a2, each Rx is, independently from each other, preferably halogen, hydrogen, or C$_1$-C$_4$haloalkyl; R$_1$ is preferably ethyl; and R$_4$ is preferably hydrogen.

Most highly preferred compounds of formula I-2a2 are those in which $Q_{a1}$ is selected from J-0z1, J-0z2, J0z3, J-1z, J-5z, J-30z, and J-43z;

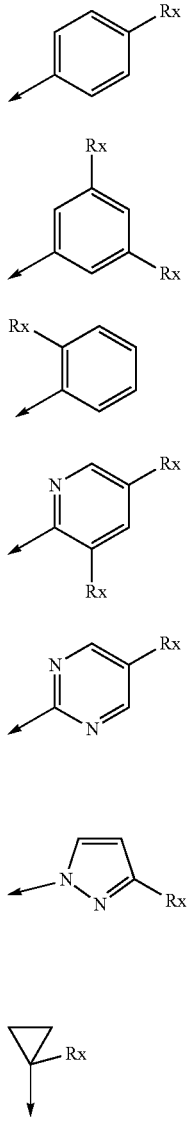

wherein each Rx is, independently from each other, hydrogen, halogen or $C_1$-$C_4$haloalkyl.

In all of the preferred embodiments of the compounds of formula I mentioned above, the substituents Q and $Qa_1$ are preferably selected from
a) phenyl, which can be substituted by halogen or $C_1$-$C_4$haloalkyl;
b) pyrazole, which can be substituted by $C_1$-$C_4$haloalkyl;
d) cyclopropyl, which can be substituted by cyano;
e) triazole, which can be substituted by halogen;
f) $C_2$-$C_6$alkinyl, which can be substituted by phenyl, wherein said phenyl can be substituted by halogen; and
g) $C_2$-$C_6$alkenyl, which can be substituted by phenyl, wherein said phenyl can be substituted by halogen.

A particular preferred embodiment of the compounds of formula I is represented by the compounds of formula I-2a3

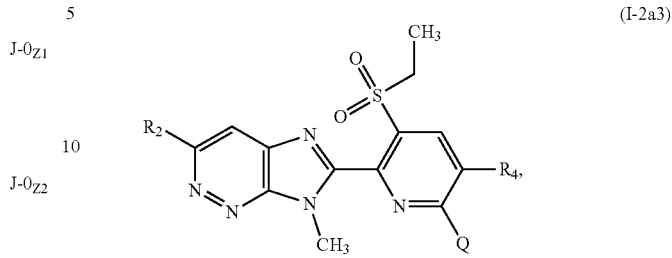

wherein
$R_2$ is $C_1$-$C_4$haloalkyl;
$R_4$ is hydrogen or $C_1$-$C_4$alkyl; and
Q is selected from
a) phenyl, which can be substituted by halogen or $C_1$-$C_4$haloalkyl;
b) pyrazole, which can be substituted by $C_1$-$C_4$haloalkyl;
d) cyclopropyl, which can be substituted by cyano;
e) triazole, which can be substituted by halogen;
f) $C_2$-$C_6$alkinyl, which can be substituted by phenyl, wherein said phenyl can be substituted by halogen; and
g) $C_2$-$C_6$alkenyl, which can be substituted by phenyl, wherein said phenyl can be substituted by halogen.

In a further embodiment of this invention, compounds of formula I are preferred, wherein
$R_1$ is $C_1$-$C_4$alkyl;
$R_2$ is $C_1$-$C_4$haloalkyl or $C_1$-$C_4$haloalkylsulfanyl;
$R_3$ is hydrogen;
$R_4$ is hydrogen or $C_1$-$C_4$haloalkyl;
Q is phenyl, which can be mono-, di- or trisubstituted by substituents selected from the group consisting of halogen and $C_1$-$C_4$haloalkyl; or
Q is $C_2$-$C_6$alkenyl which can be mono-substituted by phenyl, which phenyl itself can be mono-substituted by $C_1$-$C_4$haloalkyl; or
Q is pyrazolyl which can be mono-substituted by $C_1$-$C_4$haloalkyl or halogen; or
Q is pyrimidinyl or $C_3$-$C_6$cycloalkyl, said cycloalkyl can be substituted by cyano; or
Q is triazolyl which can be substituted by halogen; or
Q is $C_1$-$C_4$alkyl which can be substituted by cyano; or
Q is $C_2$-$C_6$alkynyl which can be mono-substituted by phenyl, which phenyl itself can be mono- or disubstituted by halogen;
X is S or $SO_2$;
$X_1$ is N—$C_1$-$C_4$alkyl; in particular N—$CH_3$;
A is CH or N; and
$A_1$ is CH or N.

The process according to the invention for preparing compounds of formula I is carried out in principle by methods known to those skilled in the art, and as described below:

Compounds of formula I, wherein A, $A_1$, $R_2$, $R_1$, $R_3$, $R_4$, X, $X_1$ and Q are as defined in formula I, can prepared (as shown in scheme 1) by a Suzuki reaction, which involves for example, reacting compounds of formula II, wherein $Xb_1$ is a leaving group, for example, chlorine, bromine or iodine, or an aryl- or alkylsulfonate such as trifluoromethanesulfonate with compounds of formula IIIa, wherein $Y_{b1}$ can be a boron-derived functional group, as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction can be catalyzed by a palladium based catalyst, for example tetrakis(triphenylphosphine)-palladium or (1,1'bis (diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water, or of dioxane and water, preferably under an inert atmosphere. The reaction temperature can preferentially range from room temperature to the boiling point of the reaction mixture. Such Suzuki reactions are well known to those skilled in the art and have been reviewed, for example *J. Orgmet. Chem.* 576, 1999, 147-168.

30-150° C. This reaction is particularly favored for compounds of formula I wherein A is methane. Alternatively such compounds can be prepared from compounds of formula II by reaction of the heterocycle Q (which contains a an appropriate NH functionality), in the presence of a base, for example an alkaline metal hydride such as sodium hydride, or an alkali metal carbonate, for example cesium or potassium carbonate, in an appropriate solvent such as N-methyl pyrollidione or DMF at temperatures between 30-150° C. The reaction is illustrated for the heterocycle J-30z in scheme 2, which gives compounds of formula Iaa, wherein A, $A_1$, $R_2$, $R_1$, $R_3$, $R_4$, X and $R_x$ are as previously defined.

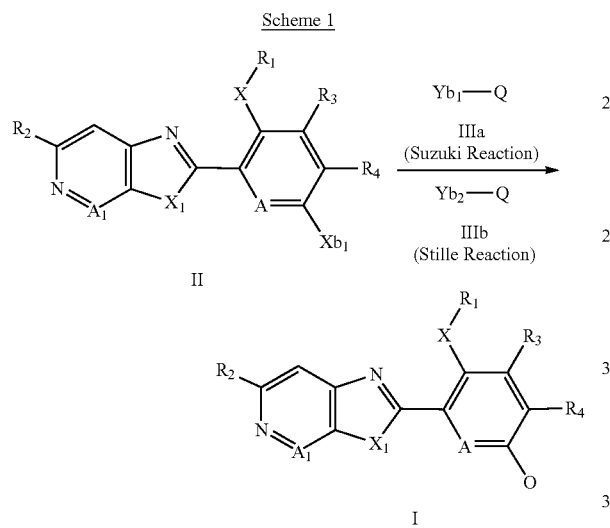

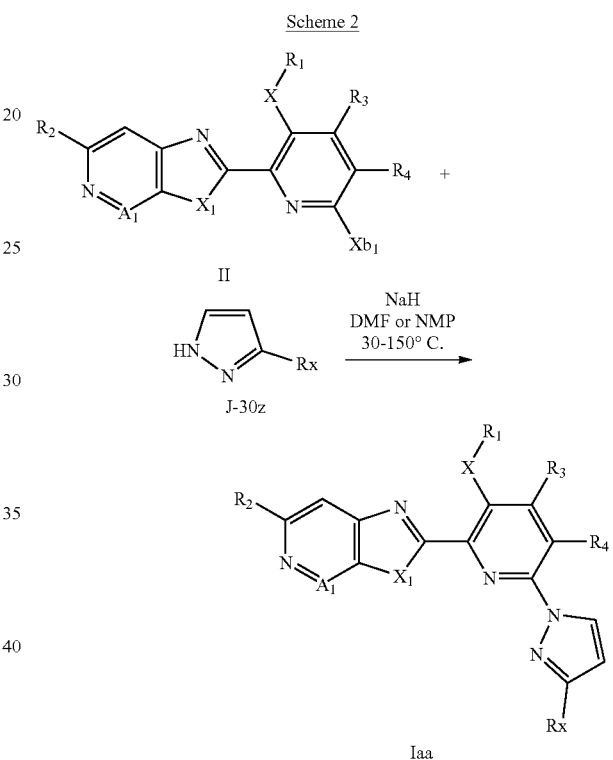

Alternatively compounds of formula I can be prepared by a Stille reaction of compounds of formula IIIb wherein $Y_{b2}$ is a trialkyl tin derivative, preferably tri-n-butyl tin, with compounds of formula II. Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136.

Compounds of formula I wherein Q is a nitrogen bearing heterocyclic system, and wherein A, $A_1$, $R_2$, $R_1$, $R_3$, $R_4$, X, $X_1$, and Q are as defined in formula I, can be prepared from compounds of formula II, wherein A, $A_1$, $R_2$, $R_1$, $R_3$, $R_4$, X, and $X_1$ are as defined in formula I, and $Xb_1$ is a leaving group such as chlorine, bromine or iodine, or an aryl- or alkylsulfonate such as trifluoromethanesulfonate by reacting the heterocycle Q (which contains a an appropriate NH functionality), in the presence of a base, for example an alkaline metal hydride such as sodium hydride, or an alkali metal carbonate, for example cesium or potassium carbonate, optionally in the presence of a copper catalyst, for example copper (I) iodide in an inert solvent such as N-methyl pyrollidione or DMF at temperatures between Compounds of formula I can also be prepared (as depicted in scheme 3) by a Suzuki reaction as described above, which involves reacting compounds of formula IV with compounds of formula V, wherein $X_{b2}$ can be a halogen, preferentially chlorine, bromine or iodine, or a sulfonate, like for example a trifluoromethanesulfonate and $Y_{b3}$ can be a boron-derived functional group, as for example $B(OH)_2$ or $B(OR_{b2})_2$ wherein $R_{b2}$ can be a $C_1$-$C_4$alkyl group or the two groups $OR_{b2}$ can form together with the boron atom a five membered ring, as for example a pinacol boronic ester. In formula IV, A, $A_1$, X, $X_1$, $R_1$, $R_2$, $R_3$, and $R_4$, are as described in formula I.

The reaction can be catalyzed by a palladium based catalyst, for example tetrakis(triphenylphosphine)-palladium, in presence of a base, like sodium carbonate, in a solvent or a solvent mixture, like, for example a mixture of 1,2-dimethoxyethane and water, preferably under inert atmosphere. The reaction temperature can preferentially range room temperature to the boiling point of the reaction mixture.

Scheme 3

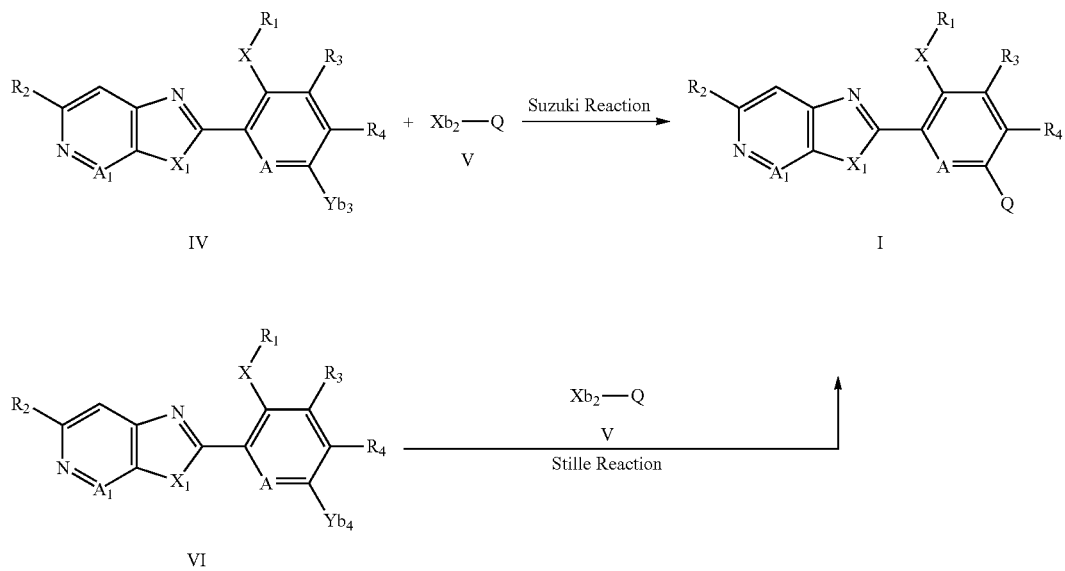

In a similar manner, compounds of formula I can be prepared by a Stille coupling (Scheme 3) of compounds of formula V with compounds of formula VI, wherein A, $A_1$, $A_2$, X, $X_1$, $R_1$, $R_2$, $R_3$, and $R_4$, are as described above, and $Y_{b4}$ is a trialkyl tin derivative, preferably tri-n-butyl tin, under conditions described as in scheme 1.

Compounds of formula IIa, wherein A is nitrogen and $A_1$, $X_1$, $R_1$, $R_2$, $R_3$ and $R_4$ are as described in formula I, and Xb1 is chlorine or bromine, can be prepared according to the methods shown in scheme 4:

Thus, compounds of formula IVa are oxidized by methods known to those skilled in the art and described in for example, in WO 2010/125985, to give compounds of formula VIIa, wherein $A_1$, $X_1$, $R_1$, $R_2$, $R_3$ and $R_4$ are as described in formula I and Xb1 is chloride or bromide. Compounds of formula VIIa upon treatment with phosphorus oxychloride or phosphorus oxychloride, optionally in the presence of a base, such as triethylamine, and optionally in a solvents, for example dichloromethane, DMF, or dioxane (see for example *Syn. Comm.*, 31(16), 2507-2511, 2001)

Scheme 4

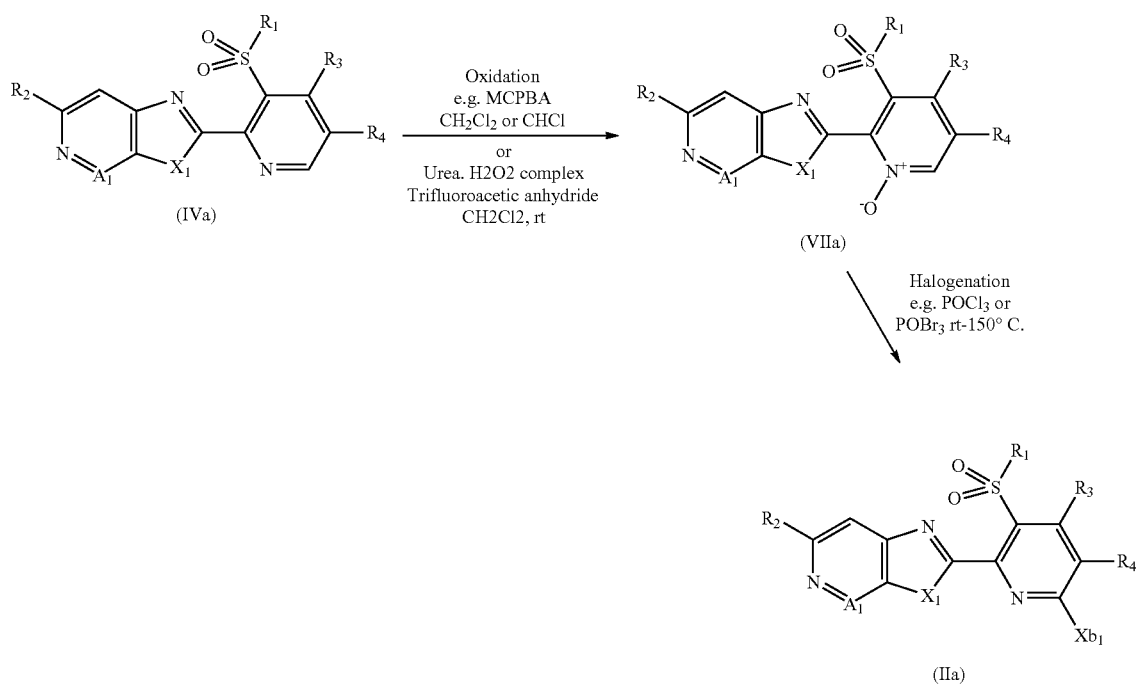

Compounds of formula II wherein A is CH, i.e. compounds of formula IIb, can be prepared as shown in scheme 5:

Scheme 5

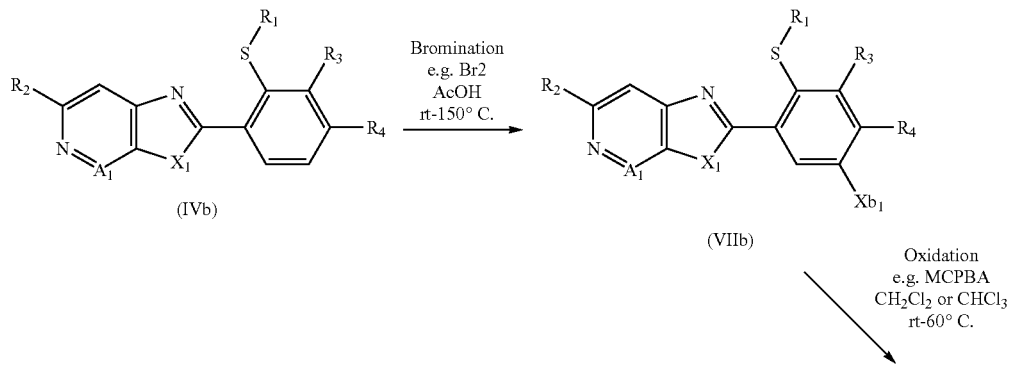

Thus, compounds of formula IVb can be halogenated to compounds of formula VIIb, wherein $A_1$, $X_1$, $R_1$, $R_2$, $R_3$ and $R_4$ are as described in formula I and Xb1 is chloride or bromide, for example with bromine or chlorine in an appropriate solvent, for example glacial acetic acid, at temperatures between 0° C. and 150° C., optionally in a microwave reactor. Alternatively the reaction may be carried out in the presence of a Lewis acid catalyst, for example iron, or Aluminum trichloride (Friedel-Craft halogenation). Similar reactions have been described I the literature (see for example Ger. Offen., 19840337, 2000, *Med. Chem. Lett.*, 3(6), 450-453; 2012 and *Macromolecules*, 47(14), 4607-4614; 2014). Oxidation of VIIb according methods known to those skilled in the art, and described for example in WO 2010/125985, leads to compounds of formula IIb, wherein $A_1$, $X_1$, $R_1$, $R_2$, $R_3$ and $R_4$ are as described in formula I and Xb1 is chloride or bromide.

Compounds of formula I can also be prepared by reaction of a compound of formula VIII,

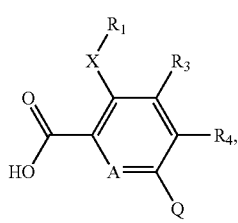

wherein X, $R_1$, $R_3$, $R_4$, Q and A are as described under formula I above, with a compound of formula IX,

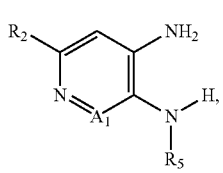

wherein $A_1$ and $R_2$ are as described under formula I above, and wherein $R_5$ is hydrogen or as described under formula I above, in the presence of a de-hydrating agent, such as for example polyphosphoric acid at temperature between 150° C. to 250° C., to yield compounds of formula I, wherein the substituents are as described above and under formula I. Such processes are well known and have been described for example in WO 2008/128968, WO 2012/086848, WO 2013/018928, WO 2014/142292 and WO 2006/003440. The process is summarized in scheme 6 for compounds of formula Ia:

Scheme 6

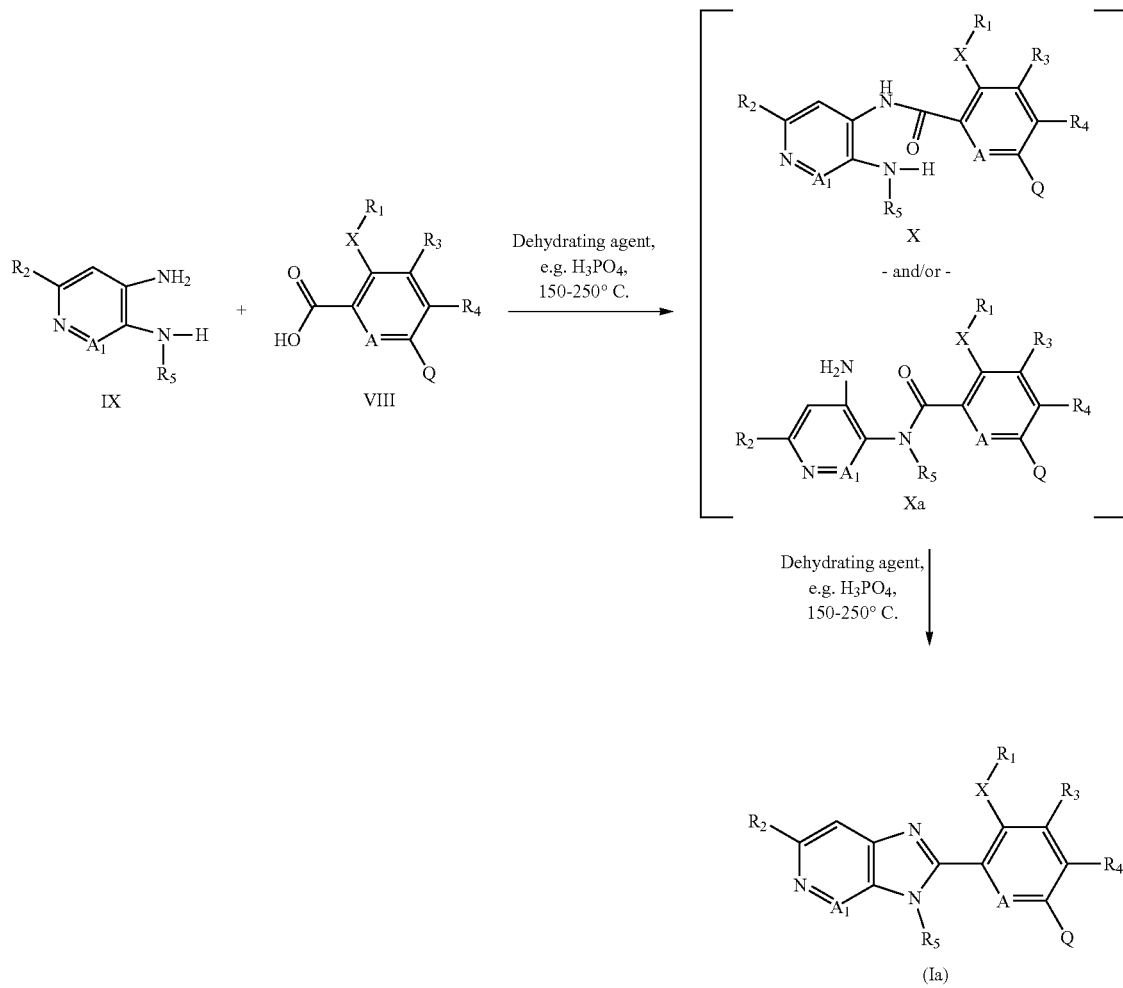

As can be seen in scheme 6, the formation of compounds of formula Ia occurs through the intermediacy of a compound of formula X (and/or its position isomer Xa). Intermediates X or intermediate Xa may form as a pure entity, or intermediates X and Xa may arise as a mixture of regioisomeric acylation products. It is in many cases advantageous to thus prepare compounds of formula (Ia) through such intermediates X/Xa, which may be isolated and optionally purified. This is illustrated for compounds of formula Ia in scheme 7:

Scheme 7.

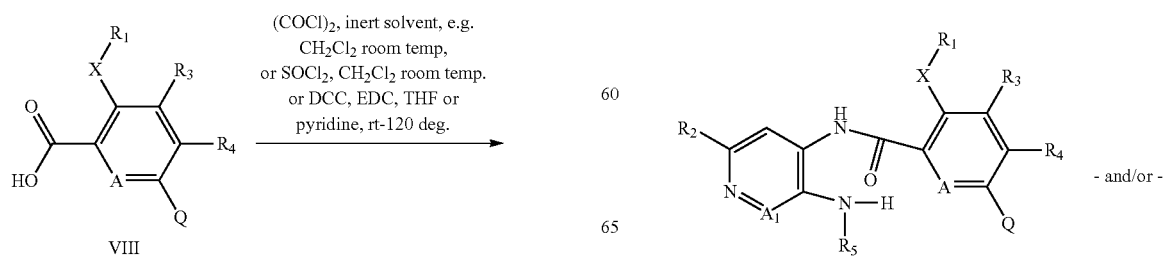

-continued

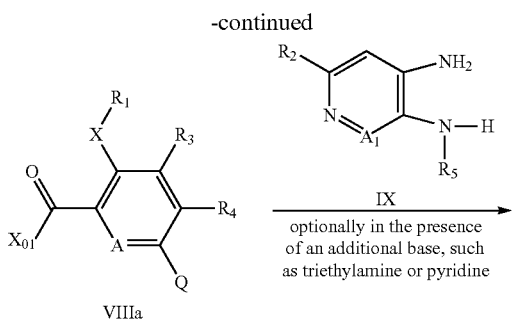

-continued

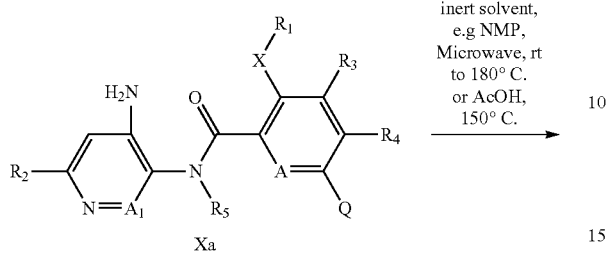

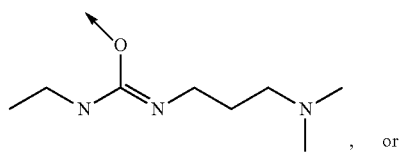

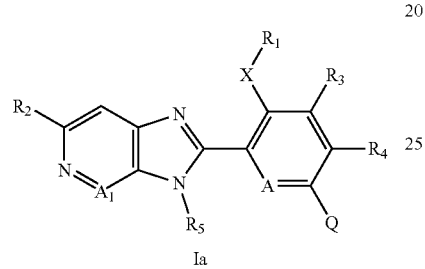

wherein:
$X_{01}$ = Halogen,

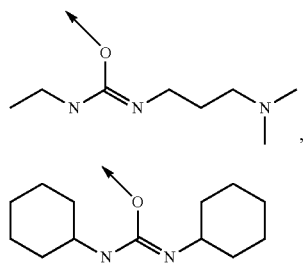

Compounds of the formula X and/or Xa (or a mixture thereof), or a salt thereof, wherein Q is as defined above, and wherein X, $R_1$, $R_2$, $R_3$, $R_4$, A and A1 are as described under formula I above, and wherein $R_5$ is hydrogen or as described under formula I above, may be prepared by
  i) activation of compound of formula VIII, wherein Q is as defined above, by methods known to those skilled in the art and described in, for example, *Tetrahedron*, 2005, 61 (46), 10827-10852, to form an activated species VIIIa, wherein Q is as defined above and wherein $X_{01}$ is halogen, preferably chlorine. For example, compounds VIIIa where $X_{01}$ is halogen, preferably chlorine, are formed by treatment of VIII with, for example, oxalyl chloride (COCl)$_2$ or thionyl chloride SOCl$_2$ in the presence of catalytic quantities of N,N-dimethylformamide (DMF) in inert solvents such as methylene chloride or tetrahydrofurane at temperatures between 20 to 100° C., preferably 25° C. Alternatively, treatment of compounds of formula VIII with, for example, 1-ethyl-3-(3-dimethylaminopropyl)carbodiimide (EDC) or dicyclohexyl carbodiimide (DCC) will generate an activated species VIIIa, wherein $X_{01}$ is respectively, in an inert solvent, such as pyridine or tetrahydrofurane, optionally in the presence of a base, such as triethylamine, at temperatures between 25-180° C.; followed by
  ii) treatment of the activated species VIIIa with a compound of formula IX (or a salt thereof), wherein wherein $A_1$ and $R_2$ are as described under formula I above, and $R_5$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl, optionally in the presence of a base, such as triethylamine or pyridine, in an inert solvents such as dichloromethane, tetrahydrofurane, dioxane or toluene, at temperatures between 0 and 80° C., to form the compounds of formula X and/or Xa (or a mixture thereof).

Compounds of formula X and/or Xa (or a mixture thereof) may further be converted into compounds of formula Ia, wherein Q is as defined above, and wherein A, $A_1$, $R_1$, $R_2$, $R_3$ and $R_4$ are as described are as described under formula I above, and wherein $R_5$ is hydrogen or as described under formula I above, by dehydration, e.g. by heating the compounds X and/or Xa (or a mixture thereof) in the presence of an acid catalyst, such as for example methane sulfonic acid, or para-toluene sulfonic acid (TsOH), in an inert solvent such as N-methyl pyrrolidine at temperatures between 25-180° C., preferably 100-170° C., optionally under microwave conditions, or by heating in acetic acid at temperatures between 100-180° C. Such processes have been described previously, for example, in WO 2010/125985 and WO2015/000715. Compounds of formula VIII are obtained by hydrolysis of compounds of formula VIIIb, VIIIc and VIIId (see below), using conditions known to those skilled in the art. An alternative synthesis of compounds of formula I is illustrated in scheme 8.

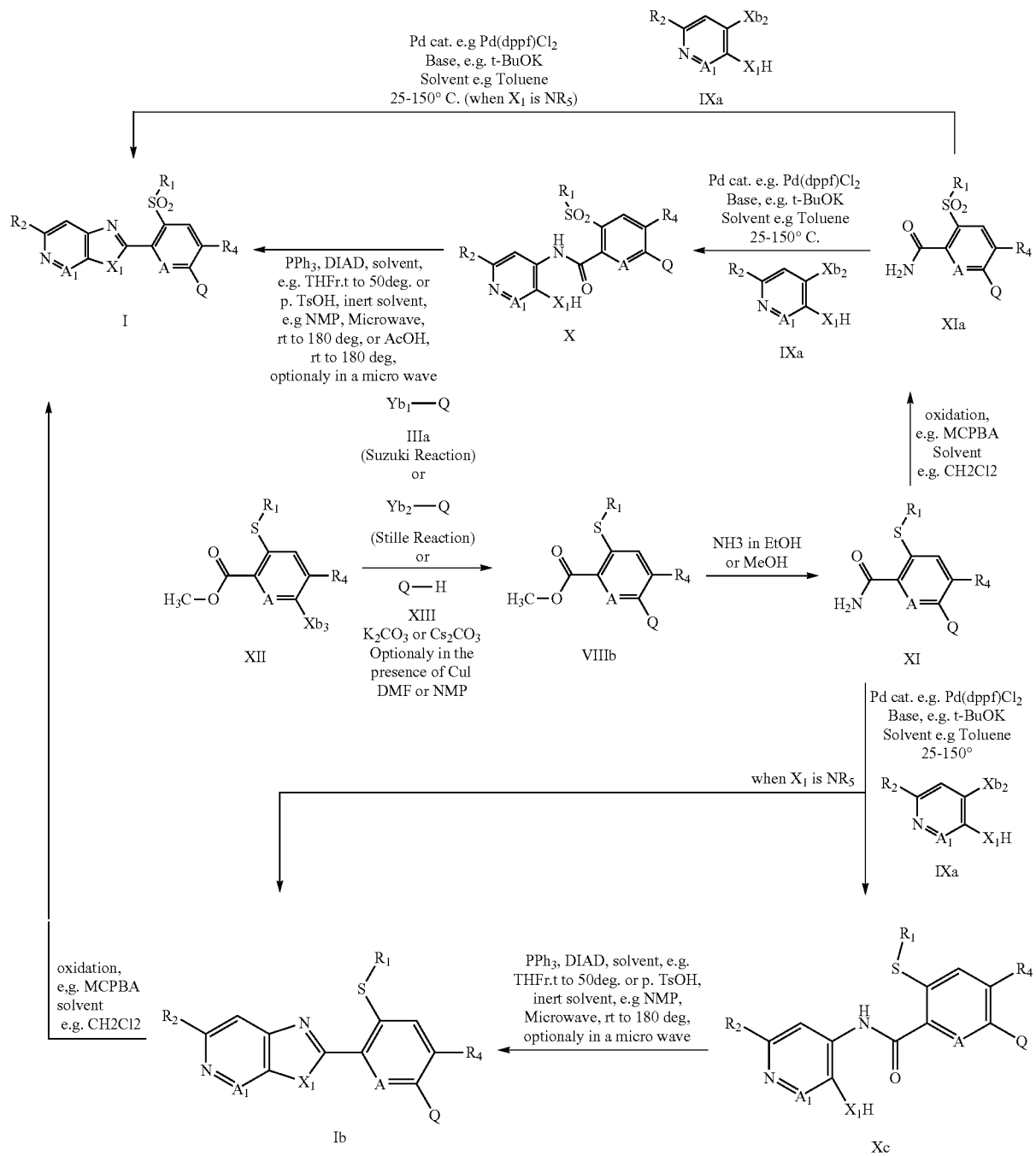

Scheme 8

As shown in scheme 8 compounds of formula XII, wherein $R_1$, $R_4$ are as described in formula I, and $Xb3$ is halogen, can be reacted with a compound of IIIa (Suzuki reaction) or IIIb, as described previously in Scheme 1 to give compounds of formula VIIIb. Alternatively compounds of formula XII can be reacted with compounds of formula XIII, wherein Q is a heterocycle and the hydrogen is attached to a nitrogen atom of that heterocycle, in the presence of a base, optionally in the presence of a copper catalyst. The chemistry is similar to that illustrated in scheme 2. Compounds of formula VIIIb are then treated with ammonia in a suitable solvent, for example methanol or ethanol to give the amides of formula XI, wherein $R_1$, $R_4$ and Q are as described in formula I. Reaction of the amides of formula XI with compounds of formula IXa, wherein $A_1$, $R_2$ and $X_1$ are as described in formula I, leads to compounds of formula Xc. Such an amide nitrogen heteroarylation reaction, typically runs under transition metal-catalysed C—N bond formation conditions involving a catalytic system (such as for example [1,1'-bis(diphenylphosphino) ferrocene] dichloropalladium (II)), usually composed of a metal, such as a palladium source (for example palladium(0) precursors like $Pd_2$(dibenzylideneacetone)$_3$, or palladium(II) precursors like Pd(OAc)$_2$) and a ligand (for example phosphine-based or N-heterocyclic carbene-based), a base, such as alkoxides (for example sodium or potassium tert-butoxide), carbonates, phosphates or silyl amides (for example potassium or cesium carbonate, potassium phosphate, or lithium hexamethyl disilazane) or hydroxides (for example sodium or potassium hydroxide), and solvents such as toluene, tetrahydrofurane, dioxane, dimethoxyethane, N,N-dimethyl formamide, N-methyl pyrrolidone and dimethylsulfoxide, as well as their aqueous solutions. These methods are known to those skilled in the art and described, for example, in WO 2014/142292. Under those above described amide cross-coupling reaction conditions, the compounds of formula Xc can be isolated, and converted to compounds of formula Ib as described in scheme 7) but may also spontaneously ring-close into the compounds of formula Ib, especially in cases where $X_1$ is $NR_5$. Oxidation of compounds of formula Ib to compounds of formula I can be achieved by methods those known to those skilled in the art, for example with meta-chloro perbenzoic acid in an inert solvent such as chloroform or methylene chloride. Alternatively the sequence of reactions can be modified so that compound of formula XI is first oxidised to a compound of formula XIa, and then converted to compounds of formula I using the same reactions previously described. Compounds of formula XIIa and XIIb can be obtained by the reactions shown in schemes 9 and 10.

Scheme 9

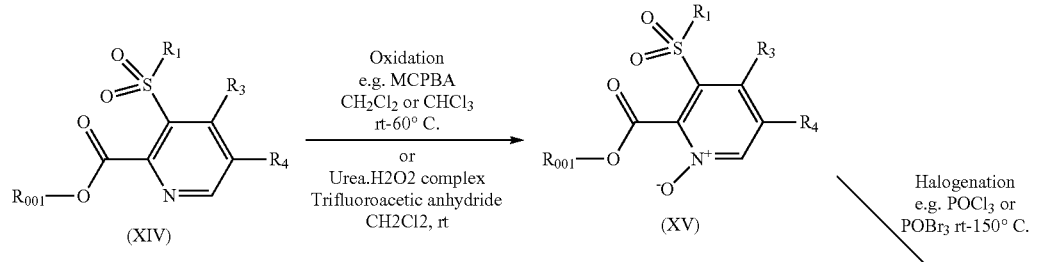

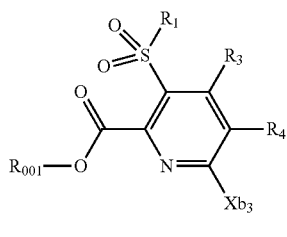

(XIIa)

Scheme 10

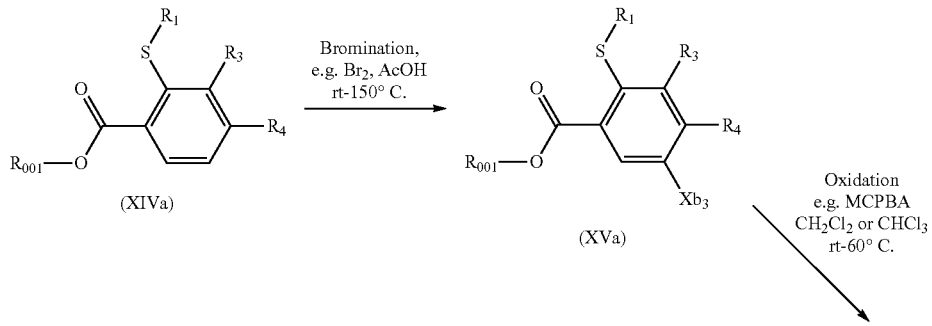

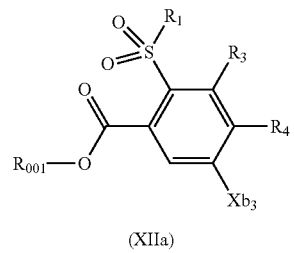

(XIIa)

In scheme 9, compounds of formula XIV, wherein $R_{001}$ is $C_1$-$C_4$alkyl, can be oxidized and the N-oxides of formula XV converted to compounds of formula XII using methodology described in scheme 4. Similarly, compounds of formula XIVa, wherein $R_{001}$ is $C_1$-$C_4$alkyl, can be halogenated to compounds of formula XVa, and then converted to compounds of formula XIIb using the chemistry described in scheme 5. Compounds of formula IV are known in the literature for example in WO2015/000715. Compounds of formula XIV and XIVa have been described for example in WO 2014132971, WO 2014123205, WO 2014119670, WO 2014119679, WO 2014119674, WO 2014119699, WO 2014119672, and WO 2014104407. Compounds of formula IXa are either described in the literature (see for example WO 2014/142292) or commercially available.

Compounds of formula I wherein Q is $C_3$-$C_6$cycloalkyl, or $C_3$-$C_6$cycloalkyl mono- or polysubstituted by substituents selected from the group consisting of halogen, cyano, $C_1$-$C_4$haloalkyl, and phenyl, may be prepared by methods described above (in particular, compounds of formula I wherein Q is cyclopropyl may be prepared by a Suzuki reaction involving cyclopropyl-boronic acid according to descriptions made in scheme 1). For the special case of compounds of formula I wherein Q is $C_3$-$C_6$cycloalkyl substituted by cyano (e.g. compounds Iaaa) and $C_1$-$C_4$haloalkyl (e.g. compounds Iaab), the compounds can be prepared by the methods shown in scheme 11.

Scheme 11

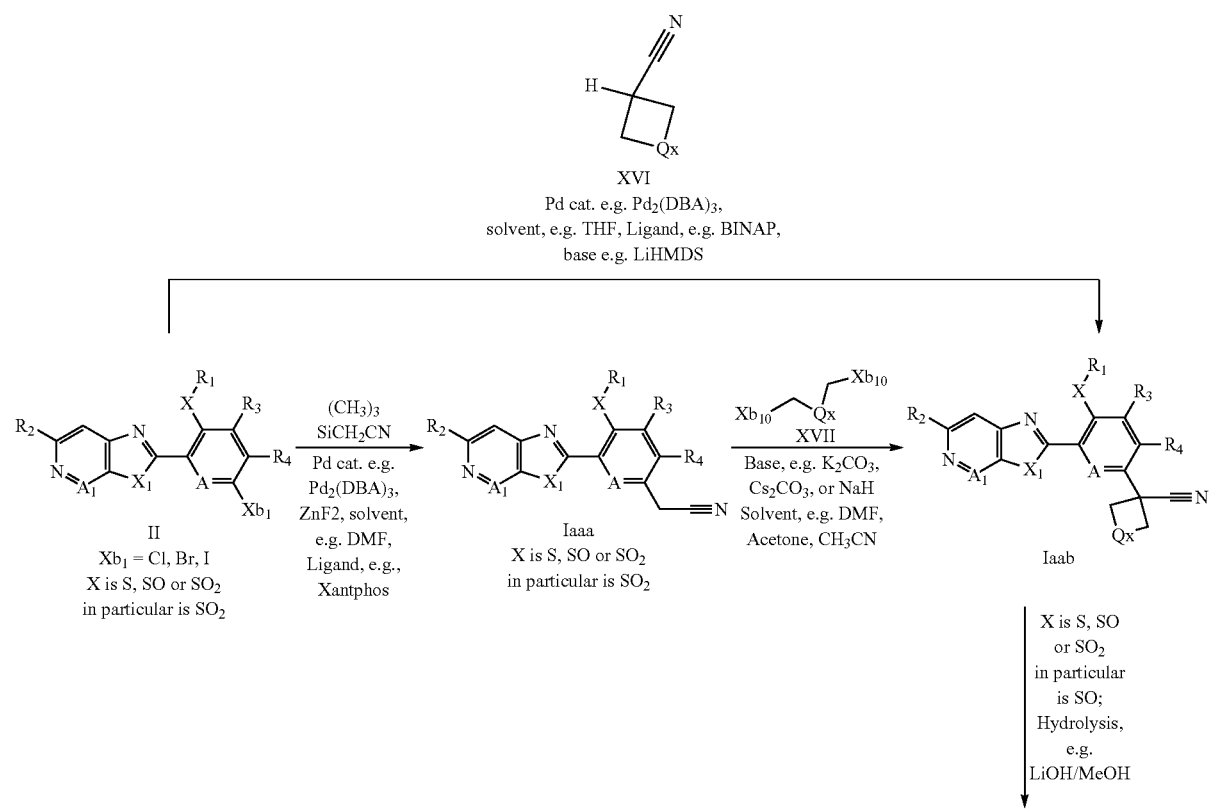

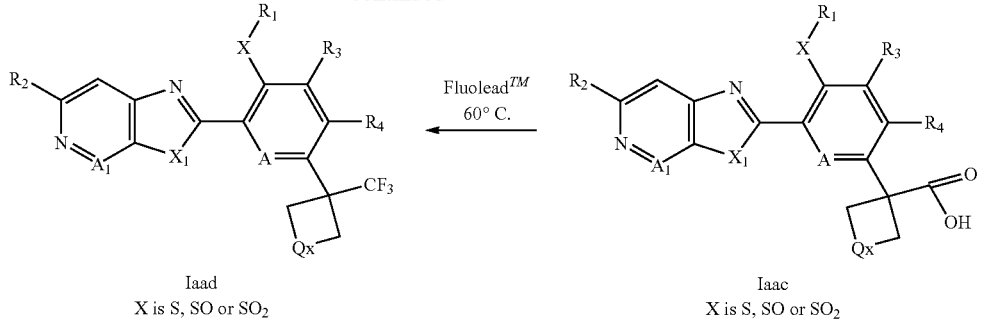

Iaad
X is S, SO or SO₂

Iaac
X is S, SO or SO₂

As shown in scheme 11, treatment of compounds of formula II, wherein X is S, SO or SO₂ (in particular SO₂), and wherein A1, A, $X_1$, $R_1$, $R_2$, $R_3$ and $R_4$ are as defined above, and in which $Xb_1$ is a leaving group like, for example, chlorine, bromine or iodine (preferably bromine), or an aryl- or alkylsulfonate such as trifluoromethanesulfonate, with trimethylsilyl-acetonitrile (TMSCN), in the presence of zinc(II)fluoride $ZnF_2$, and a palladium(0)catalyst such as tris(dibenzylideneacetone)dipalladium(0)-chloroform adduct ($Pd_2(dba)_3$), with a ligand, for example Xantphos, in an inert solvent, such as N,N-dimethylformamide DMF at temperatures between 100-180° C., optionally under microwave heating, leads to compounds of formula Iaaa, wherein X is S, SO or SO₂ (in particular SO₂). Such chemistry has been described in the literature, e.g. in *Org. Lett.* 16(24), 6314-6317, 2014. Compounds of formula Iaaa can be treated with compounds of formula XVII, wherein Qx is a direct bond or is $(CH_2)_n$ and n is 1, 2 or 3, and in which $Xb_{10}$ is a leaving group such as a halogen (preferably chlorine, bromine or iodine), in the presence of a base such as sodium hydride, potassium carbonate $K_2CO_3$, or cesium carbonate $Cs_2CO_3$, in an inert solvent such as N,N-dimethylformamide DMF, acetone, or acetonitrile, at temperatures between 0-120° C., to give compounds of formula Iaab, wherein X is S, SO or SO₂ (in particular SO₂), and wherein $A_1$, A, $X_1$, $R_1$, $R_2$, $R_3$ and $R_4$ are as defined above and in which Qx is a direct bond or is $(CH_2)_n$ and n is 1, 2 or 3. Alternatively, compounds of formula Iaa can be prepared directly from compounds of formula II by treatment with compounds of formula XVI, wherein Qx is is as described in XVII, in presence of a catalyst such as $Pd_2(dba)_3$, with a ligand, such as BINAP, a strong base such as lithium hexamethyldisilazane LiHMDS, in an inert solvent such as tetrahydrofuran THF, at temperatures between 30-80° C. Such chemistry has been described in, for example, *J. Am. Chem. Soc.* 127(45), 15824-15832, 2005.

Compounds of the formula Iaab may further be utilized for the preparation of compounds of formula Iaac and Iaad (scheme 15). Indeed, compounds of formula Iaab, wherein X is S, SO or SO₂, and wherein $A_1$, A, $X_1$, $R_1$, $R_2$, $R_3$ and $R_4$ are as defined above and in which Qx is a direct bond or is $(CH_2)_n$ and n is 1, 2 or 3, may be hydrolyzed, under conditions known to a person skilled in the art (aqueous basic or acidic conditions; for example, lithium or sodium hydroxide in an alcoholic solvent such as methanol, at temperatures between 20° C. to refluxing conditions), to compounds of formula Iaac, wherein X is S, SO or SO₂, and wherein $A_1$, A, $X_1$, $R_1$, $R_2$, $R_3$ and $R_4$ are as defined above and in which Qx is a direct bond or is $(CH_2)_n$ and n is 1, 2 or 3. Treatment of compounds of formula Iaac with reagents such as sulfur tetrafluoride $SF_4$ or Fluolead (4-tert-butyl-2,6-dimethyl phenylsulfur trifluoride), optionally in the presence of hydrogen fluoride HF, at temperatures between 20-100° C., leads to compounds of formula Iaad, wherein X is S, SO or SO₂, and wherein $A_1$, A, $X_1$, $R_1$, $R_2$, $R_3$ and $R_4$ are as defined above and in which Qx is a direct bond or is $(CH_2)_n$ and n is 1, 2 or 3.

Compounds of the formula Iaab may also be utilized for the preparation of compounds of formula Iaae (scheme 12).

Scheme 12

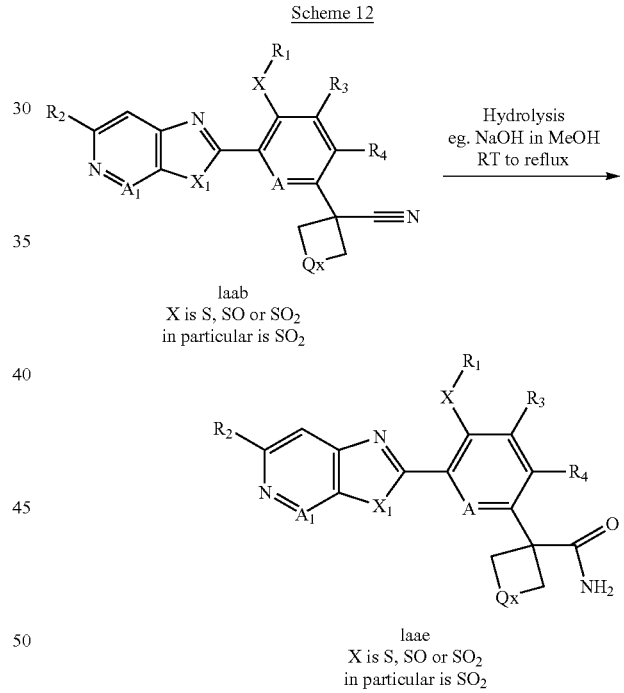

Iaab
X is S, SO or SO₂
in particular is SO₂

Iaae
X is S, SO or SO₂
in particular is SO₂

As shown in scheme 12, compounds of formula Iaab, wherein X is S, SO or SO₂, and wherein $A_1$, A, $X_1$, $R_1$, $R_2$, $R_3$ and $R_4$ are as defined above and in which Qx is a direct bond or is $(CH_2)_n$ and n is 1, 2 or 3, may be hydrolyzed, under conditions known to a person skilled in the art (aqueous basic or acidic conditions; for example, lithium or sodium hydroxide in an alcoholic solvent such as methanol, at temperatures between 20° C. to refluxing conditions; or aqueous sulphuric acid, optionally in presence of a co-solvent, at temperatures between 20° C. to refluxing conditions), to compounds of formula Iaae, wherein X is S, SO or SO₂, and wherein $A_1$, A, $X_1$, $R_1$, $R_2$, $R_3$ and $R_4$ are as defined above and in which Qx is a direct bond or is $(CH_2)_n$ and n is 1, 2 or 3.

Alternatively compounds of formula Iaab can be prepared as shown in schemes 13 and 14. As shown in scheme 13, the chemistry used is identical to that described in scheme 11, it is just that the substrates for the reactions are different. Thus, reaction of the previously described compounds XIIa or XIIb, wherein X is S or $SO_2$ (in particular $SO_2$), and wherein A, $R_1$, $R_3$ and $R_4$ are as defined above, and in which $Xb_3$ is a halogen like, for example, chlorine, bromine or iodine (preferably chlorine), or an aryl- or alkylsulfonate such as trifluoromethanesulfonate, and in which $R_{0001}$ is $C_1$-$C_4$alkyl, with trimethylsilyl-acetonitrile TMSCN as described in scheme 11, leads to compounds of formula XVIII, wherein X is S or $SO_2$ (in particular $SO_2$), and wherein A, $R_1$, $R_3$ and $R_4$ are as defined above, and in which $R_{001}$ is $C_1$-$C_4$alkyl. These are converted into compounds of formula VIIId, wherein X is S or $SO_2$ (in particular $SO_2$), and wherein Qx, wherein A, $R_1$, $R_3$ and $R_4$ are as defined above, and in which $R_{001}$ is $C_1$-$C_4$alkyl, by reacting with compounds of formula XVII as described in scheme 11. Compounds of formula VIIId are readily hydrolysed by methods known to those skilled in the art to give compounds of formula VIIIe, wherein X is S or $SO_2$ (in particular $SO_2$), and wherein Qx A, $R_1$, $R_3$ and $R_4$ are as defined above.

Scheme 13

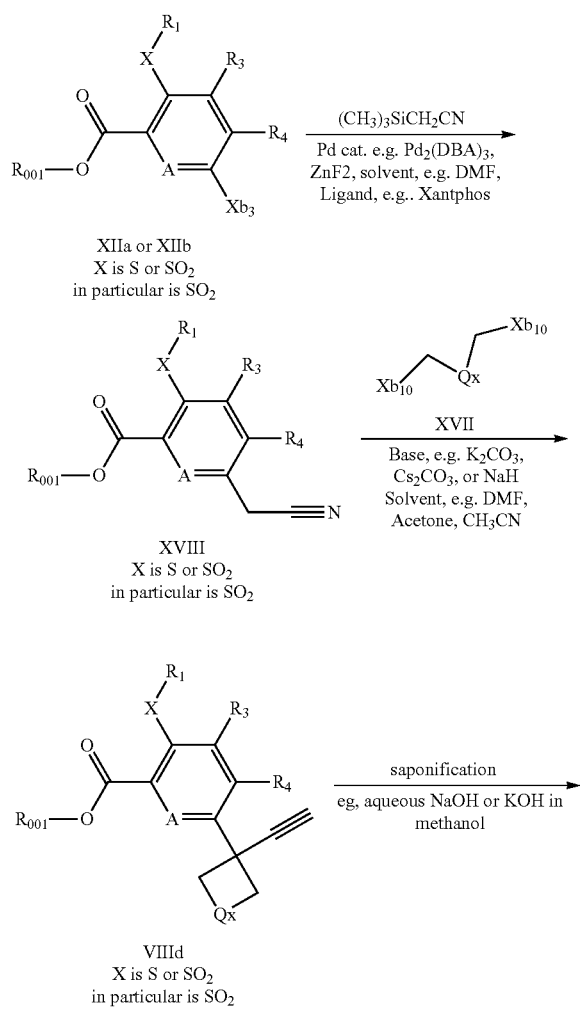

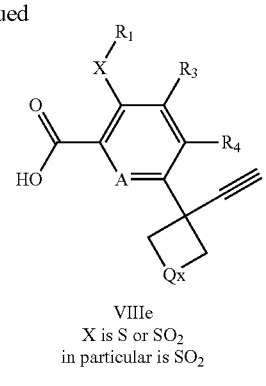

VIIIe
X is S or $SO_2$
in particular is $SO_2$

The chemistry shown in scheme 14 has previously been described in detail (see, for example, scheme 7). This chemistry involves forming an activated species VIIIf, wherein X is S, or $SO_2$ (in particular $SO_2$), and wherein Qx, A, $R_1$, $R_3$ and $R_4$ are as defined above, and in which $LG_1$ typically is chlorine, followed by amide coupling with a compound of formula IXb, wherein $X_1$, $A_1$ and $R_2$ are as previously defined, to give the compounds of formula Xd. Those compounds of formula Xd can in turn be converted to compounds of formula Iaab by a formal dehydration step, previously described in scheme 7. All substituent definitions in scheme 14 are as described previously.

Scheme 14

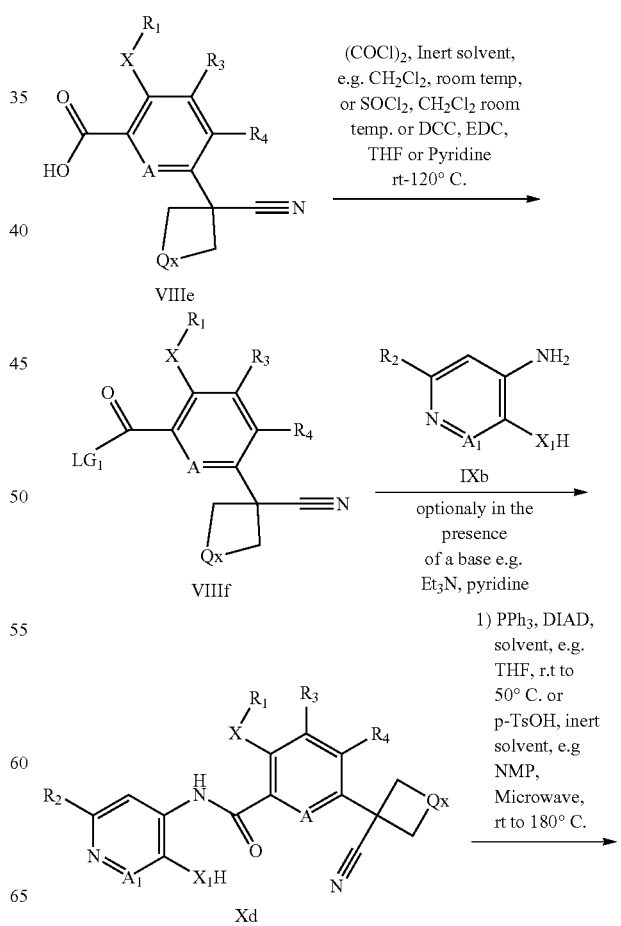

-continued

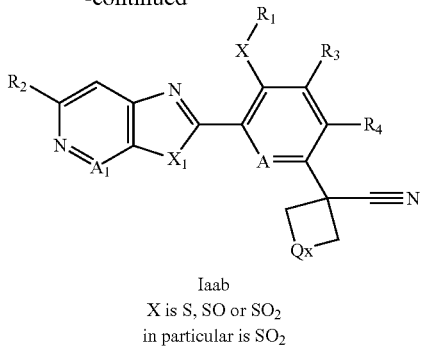

Iaab
X is S, SO or SO$_2$
in particular is SO$_2$

LG$_1$ = Cl,

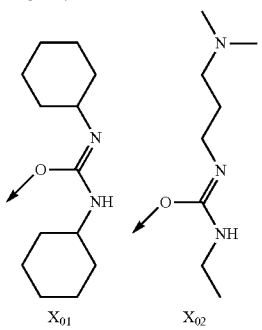

X$_{01}$  X$_{02}$

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an) other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and herein below, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.*, 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 6 below can be prepared according to the methods described above. The examples which follow are intended to illustrate the invention and show preferred compounds of formula I.

TABLE X

This table discloses the 33 substituent designations X.001 to X.033 for the formulae (Iaa), (Iab), (Iac), (Iad), (Iae) and (Iaf) which are disclosed after Table X.

| Comp. No | Q |
|---|---|
| X.001 | 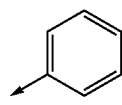 |
| X.002 | 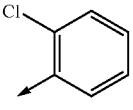 |
| X.003 | 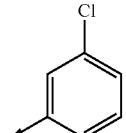 |
| X.004 | 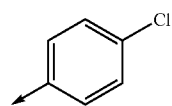 |
| X.005 | 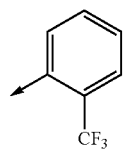 |
| X.006 | 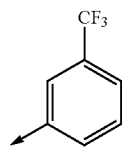 |
| X.007 | 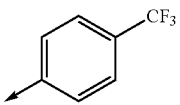 |
| X.008 | 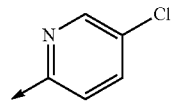 |

TABLE X-continued
This table discloses the 33 substituent designations X.001 to X.033 for the formulae (Iaa), (Iab), (Iac), (Iad), (Iae) and (Iaf) which are disclosed after Table X.
| Comp. No | Q |
|---|---|
| X.009 | 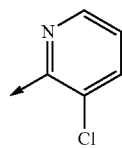 |
| X.010 | 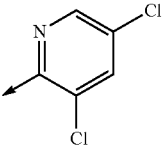 |
| X.011 | 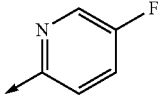 |
| X-012 | 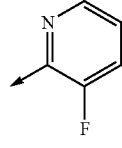 |
| X-013 |  |
| X.014 |  |
| X.015 | 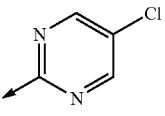 |
| X.016 | 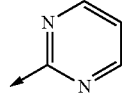 |
| X.017 | 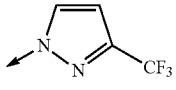 |
| X.018 | 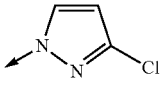 |
| X-019 | 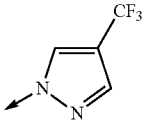 |

TABLE X-continued

This table discloses the 33 substituent designations X.001 to X.033 for the formulae (Iaa), (Iab), (Iac), (Iad), (Iae) and (Iaf) which are disclosed after Table X.

| Comp. No | Q |
| --- | --- |
| X-020 | 4-chloro-1H-pyrazol-1-yl |
| X-021 | cyclopropyl |
| X-022 | 1-cyanocyclopropyl |
| X-023 | 1-methylcyclopropyl |
| X-024 | 1-(trifluoromethyl)cyclopropyl |
| X-025 | (E)-2-(2-(trifluoromethyl)phenyl)ethenyl |
| X-026 | 2-(2-(trifluoromethyl)phenyl)ethyl |
| X-027 | (2-(trifluoromethyl)phenyl)ethynyl |
| X-028 | (3,5-difluorophenyl)ethynyl |
| X-029 | (3-fluorophenyl)ethynyl |

TABLE X-continued

This table discloses the 33 substituent designations X.001 to X.033 for the formulae (Iaa), (Iab), (Iac), (Iad), (Iae) and (Iaf) which are disclosed after Table X.

| Comp. No | Q |
|---|---|
| X-030 | 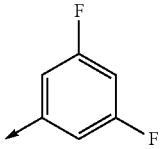 |
| X-031 | 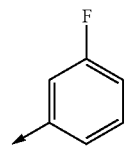 |
| X-032 | 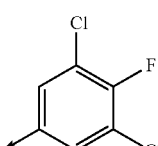 |
| X-033 | 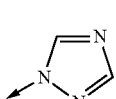 |

Table 1:

This table discloses the 33 compounds 1.001 to 1.033 of the formula (Iaa):

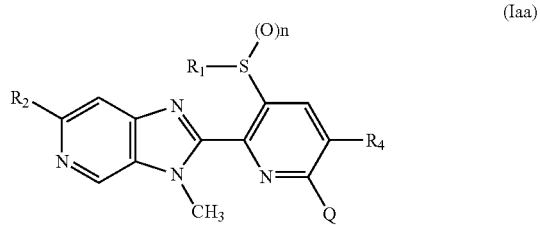
(Iaa)

wherein n is 0, and $R_2$ is $CF_3$, $R_1$ is ethyl, $R_4$ is hydrogen and Q is as defined in lines X.001-X.033 in table X. For example, compound 1.004 has the following structure:

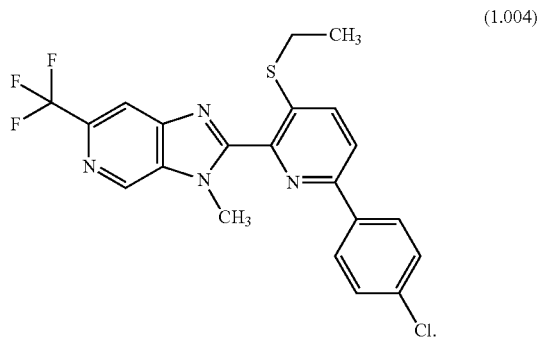 [SMILES: CCSc1ccc(-c2ccc(Cl)cc2)nc1-c1nc2cc(C(F)(F)F)ncc2n1C]
(1.004)

Table 2:

This table discloses the 33 compounds 2.001 to 2.033 of the formula (Iaa) wherein n is 2, and $R_2$ is $CF_3$, $R_1$ is ethyl, $R_4$ is hydrogen and Q is as defined in lines X.001-X.033 in table X.

Table 3:

This table discloses the 33 compounds 3.001 to 3.033 of the formula (Iaa) wherein n is 0, and $R_2$ is $CF_2CF_3$, $R_1$ is ethyl, $R_4$ is hydrogen and Q is as defined in lines X.001-X.033 in table X.

Table 4:

This table discloses the 33 compounds 4.001 to 4.033 of the formula (Iaa) wherein n is 2, and $R_2$ is $CF_2CF_3$, $R_1$ is ethyl, $R_4$ is hydrogen and Q is as defined in lines X.001-X.033 in table X.

Table 5:

This table discloses the 33 compounds 5.001 to 5.033 of the formula (Iaa) wherein n is 0, and $R_2$ is $CF(CF_3)_2$, $R_1$ is ethyl, $R_4$ is hydrogen and Q is as defined in lines X.001-X.033 in table X.

Table 6:

This table discloses the 33 compounds 6.001 to 6.033 of the formula (Iaa) wherein n is 2, and $R_2$ is $CF(CF_3)_2$, $R_1$ is ethyl, $R_4$ is hydrogen and Q is as defined in lines X.001-X.033 in table X.

Table 7:

This table discloses the 33 compounds 7.001 to 7.033 of the formula (Iaa) wherein n is 0, and $R_2$ is $OCF_3$, $R_1$ is ethyl, $R_4$ is hydrogen and Q is as defined in lines X.001-X.033 in table X.

Table 8:

This table discloses the 33 compounds 8.001 to 8.033 of the formula (Iaa) wherein n is 2, and $R_2$ is $OCF_3$, $R_1$ is ethyl, $R_4$ is hydrogen and Q is as defined in lines X.001-X.033 in table X.

Table 9:
This table discloses the 33 compounds 9.001 to 9.033 of the formula (Iaa) wherein n is 0, and $R_2$ is $SCF_3$, $R_1$ is ethyl, $R_4$ is hydrogen and Q is as defined in lines X.001-X.033 in table X.

Table 10:
This table discloses the 33 compounds 10.001 to 10.033 of the formula (Iaa) wherein n is 2, and $R_2$ is $SCF_3$, $R_1$ is ethyl, $R_4$ is hydrogen and Q is as defined in lines X.001-X.033 in table X.

Table 11:
This table discloses the 33 compounds 11.001 to 11.033 of the formula (Iaa) wherein n is 0, and $R_2$ is $SOCF_3$, $R_1$ is ethyl, $R_4$ is hydrogen and Q is as defined in lines X.001-X.033 in table X.

Table 12:
This table discloses the 33 compounds 12.001 to 12.033 of the formula (Iaa) wherein n is 2, and $R_2$ is $SOCF_3$, $R_1$ is ethyl, $R_4$ is hydrogen and Q is as defined in lines X.001-X.033 in table X.

Table 13:
This table discloses the 33 compounds 13.001 to 13.033 of the formula (Iaa) wherein n is 0, and $R_2$ is $SO_2CF_3$, $R_1$ is ethyl, $R_4$ is hydrogen and Q is as defined in lines X.001-X.033 in table X.

Table 14:
This table discloses the 33 compounds 14.001 to 14.033 of the formula (Iaa) wherein n is 2, and $R_2$ is $SO_2CF_3$, $R_1$ is ethyl, $R_4$ is hydrogen and Q is as defined in lines X.001-X.033 in table X.

Table 15:
This table discloses the 33 compounds 15.001 to 15.027 of the formula (Iaa) wherein n is 0, and $R_2$ is Br, $R_1$ is ethyl, $R_4$ is hydrogen and Q is as defined in lines X.001-X.033 in table X.

Table 16:
This table discloses the 33 compounds 16.001 to 16.033 of the formula (Iaa) wherein n is 2, and $R_2$ is Br, $R_1$ is ethyl, $R_4$ is hydrogen and Q is as defined in lines X.001-X.033 in table X.

Table 17:
This table discloses the 33 compounds 17.001 to 17.033 of the formula (Iaa) wherein n is 0, and $R_2$ is $CF_2CH_3$, $R_1$ is ethyl, $R_4$ is hydrogen and Q is as defined in lines X.001-X.033 in table X.

Table 18:
This table discloses the 33 compounds 18.001 to 18.033 of the formula (Iaa) wherein n is 2, and $R_2$ is $CF_2CH_3$, $R_1$ is ethyl, $R_4$ is hydrogen and Q is as defined in lines X.001-X.033 in table X.

Table 19:
This table discloses the 33 compounds 19.001 to 19.033 of the formula (Iaa) wherein n is 0, and $R_2$ is $OCF_2CHFCF_3$, $R_1$ is ethyl, $R_4$ is hydrogen and Q is as defined in lines X.001-X.033 in table X.

Table 20:
This table discloses the 33 compounds 20.001 to 20.033 of the formula (Iaa) wherein n is 2, and $R_2$ is $OCH_2CHFCF_3$, $R_1$ is ethyl, $R_4$ is hydrogen and Q is as defined in lines X.001-X.033 in table X.

Table 21:
This table discloses the 33 compounds 21.001 to 21.033 of the formula (Iaa) wherein n is 0, and $R_2$ is $OCH_2CHF_2$, $R_1$ is ethyl, $R_4$ is hydrogen and Q is as defined in lines X.001-X.033 in table X.

Table 22:
This table discloses the 33 compounds 22.001 to 22.033 of the formula (Iaa) wherein n is 2, and $R_2$ is $OCH_2CHF_2$, $R_1$ is ethyl, $R_4$ is hydrogen and Q is as defined in lines X.001-X.033 in table X.

Table 23:
This table discloses the 33 compounds 23.001 to 23.033 of the formula (Iaa) wherein n is 0, and $R_2$ is $C(CF_3)_2OCH_3$, $R_1$ is ethyl, $R_4$ is hydrogen and Q is as defined in lines X.001-X.033 in table X.

Table 24:
This table discloses the 33 compounds 24.001 to 24.033 of the formula (Iaa) wherein n is 2, and $R_2$ is $C(CF_3)_2OCH_3$, $R_1$ is ethyl, $R_4$ is hydrogen and Q is as defined in lines X.001-X.033 in table X.

Table 25:
This table discloses the 33 compounds 25.001 to 25.033 of the formula (Iaa):
wherein n is 0, and $R_2$ is $CF_3$, $R_1$ is ethyl, $R_4$ is $CF_3$ and Q is as defined in lines X.001-X.033 in table X.

Table 26:
This table discloses the 33 compounds 26.001 to 26.024 of the formula (Iaa) wherein n is 2, and $R_2$ is $CF_3$, $R_1$ is ethyl, $R_4$ is $CF_3$ and Q is as defined in lines X.001-X.033 in table X.

Table 27:
This table discloses the 33 compounds 27.001 to 27.033 of the formula (Iaa) wherein n is 0, and $R_2$ is $CF_2CF_3$, $R_1$ is ethyl, $R_4$ is $CF_3$ and Q is as defined in lines X.001-X.033 in table X.

Table 28:
This table discloses the 28 compounds 28.001 to 28.033 of the formula (Iaa) wherein n is 2, and $R_2$ is $CF_2CF_3$, $R_1$ is ethyl, $R_4$ is $CF_3$ and Q is as defined in lines X.001-X.033 in table X.

Table 29:
This table discloses the 27 compounds 29.001 to 29.033 of the formula (Iaa) wherein n is 0, and $R_2$ is $CF(CF_3)_2$, $R_1$ is ethyl, $R_4$ is $CF_3$ and Q is as defined in lines X.001-X.033 in table X.

Table 30:
This table discloses the 33 compounds 30.001 to 30.033 of the formula (Iaa) wherein n is 2, and $R_2$ is $CF(CF_3)_2$, $R_1$ is ethyl, $R_4$ is $CF_3$ and Q is as defined in lines X.001-X.033 in table X.

Table 31:
This table discloses the 33 compounds 31.001 to 31.033 of the formula (Iaa) wherein n is 0, and $R_2$ is $OCF_3$, $R_1$ is ethyl, $R_4$ is $CF_3$ and Q is as defined in lines X.001-X.033 in table X.

Table 32:
This table discloses the 33 compounds 32.001 to 32.033 of the formula (Iaa) wherein n is 2, and $R_2$ is $OCF_3$, $R_1$ is ethyl, $R_4$ is $CF_3$ and Q is as defined in lines X.001-X.033 in table X.

Table 33:
This table discloses the 33 compounds 33.001 to 33.033 of the formula (Iaa) wherein n is 0, and $R_2$ is $SCF_3$, $R_1$ is ethyl, $R_4$ is $CF_3$ and Q is as defined in lines X.001-X.033 in table X.

Table 34:
This table discloses the 33 compounds 34.001 to 34.033 of the formula (Iaa) wherein n is 2, and $R_2$ is $SCF_3$, $R_1$ is ethyl, $R_4$ is $CF_3$ and Q is as defined in lines X.001-X.033 in table X.

Table 35:
This table discloses the 33 compounds 35.001 to 35.033 of the formula (Iaa) wherein n is 0, and $R_2$ is $SOCF_3$, $R_1$ is ethyl, $R_4$ is $CF_3$ and Q is as defined in lines X.001-X.033 in table X.

Table 36:
This table discloses the 33 compounds 36.001 to 36.033 of the formula (Iaa) wherein n is 2, and $R_2$ is $SOCF_3$, $R_1$ is ethyl, $R_4$ is $CF_3$ and Q is as defined in lines X.001-X.033 in table X.

Table 37:
This table discloses the 33 compounds 37.001 to 37.033 of the formula (Iaa) wherein n is 0, and $R_2$ is $SO_2CF_3$, $R_1$ is ethyl, $R_4$ is $CF_3$ and Q is as defined in lines X.001-X.033 in table X.

Table 38:
This table discloses the 33 compounds 38.001 to 38.033 of the formula (Iaa) wherein n is 2, and $R_2$ is $SO_2CF_3$, $R_1$ is ethyl, $R_4$ is $CF_3$ and Q is as defined in lines X.001-X.033 in table X.

Table 39:
This table discloses the 33 compounds 39.001 to 39.033 of the formula (Iaa) wherein n is 0, and $R_2$ is Br, $R_1$ is ethyl, $R_4$ is $CF_3$ and Q is as defined in lines X.001-X.033 in table X.

Table 40:
This table discloses the 33 compounds 40.001 to 40.033 of the formula (Iaa) wherein n is 2, and $R_2$ is Br, $R_1$ is ethyl, $R_4$ is $CF_3$ and Q is as defined in lines X.001-X.033 in table X.

Table 41:
This table discloses the 33 compounds 41.001 to 41.033 of the formula (Iaa) wherein n is 0, and $R_2$ is $CF_2CH_3$, $R_1$ is ethyl, $R_4$ is $CF_3$ and Q is as defined in lines X.001-X.033 in table X.

Table 42:
This table discloses the 33 compounds 42.001 to 42.033 of the formula (Iaa) wherein n is 2, and $R_2$ is $CF_2CH_3$, $R_1$ is ethyl, $R_4$ is $CF_3$ and Q is as defined in lines X.001-X.033 in table X.

Table 43:
This table discloses the 33 compounds 43.001 to 43.033 of the formula (Iaa) wherein n is 0, and $R_2$ is $OCF_2CHFCF_3$, $R_1$ is ethyl, $R_4$ is $CF_3$ and Q is as defined in lines X.001-X.033 in table X.

Table 44:
This table discloses the 33 compounds 44.001 to 44.033 of the formula (Iaa) wherein n is 2, and $R_2$ is $OCF_2CHFCF_3$, $R_1$ is ethyl, $R_4$ is $CF_3$ and Q is as defined in lines X.001-X.033 in table X.

Table 45:
This table discloses the 33 compounds 45.001 to 45.033 of the formula (Iaa) wherein n is 0, and $R_2$ is $OCF_2CHFCF_3$, $R_1$ is ethyl, $R_4$ is $CF_3$ and Q is as defined in lines X.001-X.033 in table X.

Table 46:
This table discloses the 33 compounds 46.001 to 46.033 of the formula (Iaa) wherein n is 2, and $R_2$ is $OCF_2CHFCF_3$, $R_1$ is ethyl, $R_4$ is $CF_3$ and Q is as defined in lines X.001-X.033 in table X.

Table 47:
This table discloses the 33 compounds 47.001 to 47.033 of the formula (Iaa) wherein n is 0, and $R_2$ is $C(CF_3)_2OCH_3$, $R_1$ is ethyl, $R_4$ is $CF_3$ and Q is as defined in lines X.001-X.033 in table X.

Table 48:
This table discloses the 33 compounds 48.001 to 48.033 of the formula (Iaa) wherein n is 2, and $R_2$ is $C(CF_3)_2OCH_3$, $R_1$ is ethyl, $R_4$ is $CF_3$ and Q is as defined in lines X.001-X.033 in table X.

Table 49:
This table discloses the 33 compounds 49.001 to 49.033 of the formula (Iab):

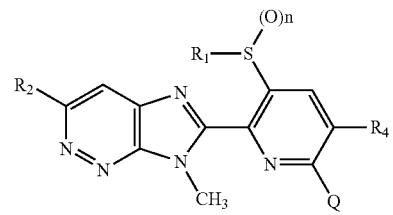

wherein n is 0, and $R_2$ is $CF_3$, $R_1$ is ethyl, $R_4$ is hydrogen and Q is as defined in lines X.001-X.033 in table X. For example, compound 49.017 has the following structure:

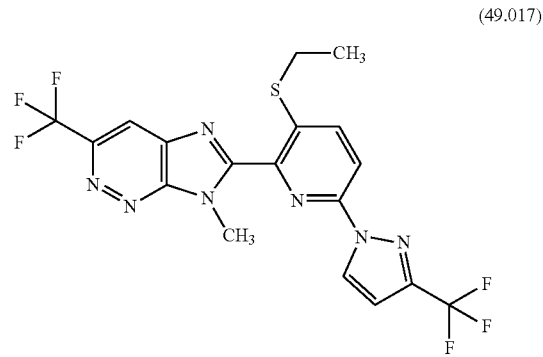 [SMILES: CCSc1ccc(-n2ccc(C(F)(F)F)n2)nc1-c1nc2cc(C(F)(F)F)nnc2n1C]

Table 50:
This table discloses the 33 compounds 50.001 to 50.024 of the formula (Iab) wherein n is 2, and $R_2$ is $CF_3$, $R_1$ is ethyl, $R_4$ is hydrogen and Q is as defined in lines X.001-X.033 in table X.

Table 51:
This table discloses the 33 compounds 51.001 to 51.033 of the formula (Iab) wherein n is 0, and $R_2$ is $CF_2CF_3$, $R_1$ is ethyl, $R_4$ is hydrogen and Q is as defined in lines X.001-X.033 in table X.

Table 52:
This table discloses the 33 compounds 52.001 to 52.033 of the formula (Iab) wherein n is 2, and $R_2$ is $CF_2CF_3$, $R_1$ is ethyl, $R_4$ is hydrogen and Q is as defined in lines X.001-X.033 in table X.

Table 53:
This table discloses the 33 compounds 53.001 to 53.033 of the formula (Iab) wherein n is 0, and $R_2$ is $CF(CF_3)_2$, $R_1$ is ethyl, $R_4$ is hydrogen and Q is as defined in lines X.001-X.033 in table X.

Table 54:
This table discloses the 33 compounds 53.001 to 53.033 of the formula (Iab) wherein n is 2, and $R_2$ is $CF(CF_3)_2$, $R_1$ is ethyl, $R_4$ is hydrogen and Q is as defined in lines X.001-X.033 in table X.

Table 55:
This table discloses the 33 compounds 55.001 to 55.033 of the formula (Iab) wherein n is 0, and $R_2$ is $SCF_3$, $R_1$ is ethyl, $R_4$ is hydrogen and Q is as defined in lines X.001-X.033 in table X.

Table 56:
This table discloses the 33 compounds 56.001 to 56.033 of the formula (Iab) wherein n is 2, and $R_2$ is $SCF_3$, $R_1$ is ethyl, $R_4$ is hydrogen and Q is as defined in lines X.001-X.033 in table X.

Table 57:
This table discloses the 33 compounds 57.001 to 57.033 of the formula (Iac):

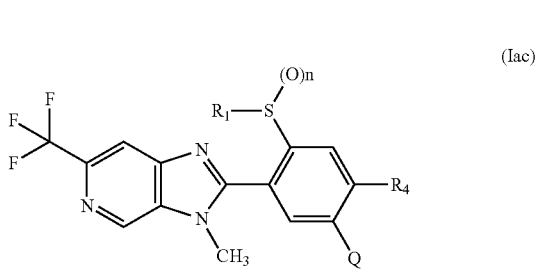
(Iac)

wherein n is 0, and $R_2$ is $CF_3$, $R_1$ is ethyl, $R_4$ is hydrogen and Q is as defined in lines X.001-X.033 in table X. For example, compound 57.021 has the following structure:

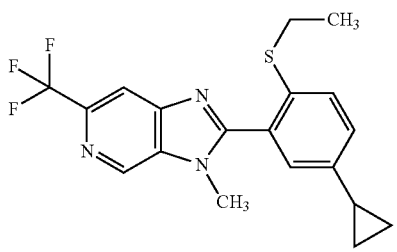
(57.021)

Table 58:
This table discloses the 33 compounds 58.001 to 58.024 of the formula (Iac) wherein n is 2, and $R_2$ is $CF_3$, $R_1$ is ethyl, $R_4$ is hydrogen and Q is as defined in lines X.001-X.033 in table X.

Table 59:
This table discloses the 33 compounds 59.001 to 59.033 of the formula (Iac) wherein n is 0, and $R_2$ is $CF_2CF_3$, $R_1$ is ethyl, $R_4$ is hydrogen and Q is as defined in lines X.001-X.033 in table X.

Table 60:
This table discloses the 33 compounds 60.001 to 60.033 of the formula (Iac) wherein n is 2, and $R_2$ is $CF_2CF_3$, $R_1$ is ethyl, $R_4$ is hydrogen and Q is as defined in lines X.001-X.033 in table X.

Table 61:
This table discloses the 33 compounds 61.001 to 61.033 of the formula (Iac) wherein n is 0, and $R_2$ is $CF(CF_3)_2$, $R_1$ is ethyl, $R_4$ is hydrogen and Q is as defined in lines X.001-X.033 in table X.

Table 62:
This table discloses the 33 compounds 62.001 to 62.033 of the formula (Iac) wherein n is 2, and $R_2$ is $CF(CF_3)_2$, $R_1$ is ethyl, $R_4$ is hydrogen and Q is as defined in lines X.001-X.033 in table X.

Table 63:
This table discloses the 33 compounds 63.001 to 63.033 of the formula (Iac) wherein n is 0, and $R_2$ is $SCF_3$, $R_1$ is ethyl, $R_4$ is hydrogen and Q is as defined in lines X.001-X.033 in table X.

Table 64:
This table discloses the 33 compounds 64.001 to 64.033 of the formula (Iac) wherein n is 2, and $R_2$ is $SCF_3$, $R_1$ is ethyl, $R_4$ is hydrogen and Q is as defined in lines X.001-X.033 in table X.

Table 65:
This table discloses the 33 compounds 65.001 to 65.033 of the formula (Iad):

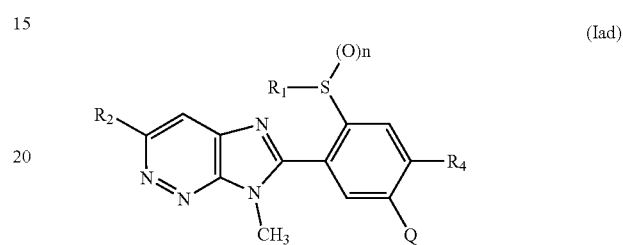
(Iad)

wherein n is 0, and $R_2$ is $CF_3$, $R_1$ is ethyl, $R_4$ is hydrogen and Q is as defined in lines X.001-X.033 in table X. For example, compound 65.016 has the following structure:

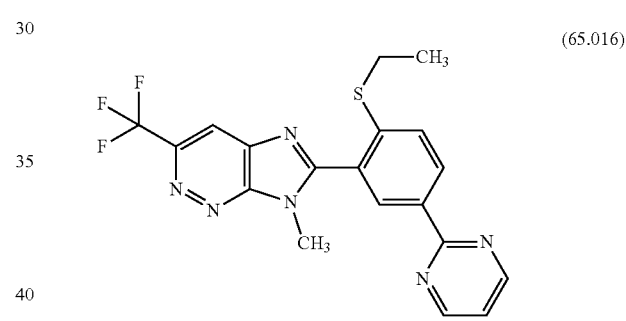
(65.016)

Table 66:
This table discloses the 33 compounds 66.001 to 66.024 of the formula (Iad) wherein n is 2, and $R_2$ is $CF_3$, $R_1$ is ethyl, $R_4$ is hydrogen and Q is as defined in lines X.001-X.033 in table X.

Table 67:
This table discloses the 33 compounds 67.001 to 67.033 of the formula (Iad) wherein n is 0, and $R_2$ is $CF_2CF_3$, $R_1$ is ethyl, $R_4$ is hydrogen and Q is as defined in lines X.001-X.033 in table X.

Table 68:
This table discloses the 33 compounds 68.001 to 68.033 of the formula (Iad) wherein n is 2, and $R_2$ is $CF_2CF_3$, $R_1$ is ethyl, $R_4$ is hydrogen and Q is as defined in lines X.001-X.033 in table X.

Table 69:
This table discloses the 33 compounds 69.001 to 69.033 of the formula (Iad) wherein n is 0, and $R_2$ is $CF(CF_3)_2$, $R_1$ is ethyl, $R_4$ is hydrogen and Q is as defined in lines X.001-X.033 in table X.

Table 70:
This table discloses the 33 compounds 70.001 to 70.033 of the formula (Iad) wherein n is 2, and $R_2$ is $CF(CF_3)_2$, $R_1$ is ethyl, $R_4$ is hydrogen and Q is as defined in lines X.001-X.033 in table X.

Table 71:

This table discloses the 33 compounds 71.001 to 71.033 of the formula (Iad) wherein n is 0, and $R_2$ is $SCF_3$, $R_1$ is ethyl, $R_4$ is hydrogen and Q is as defined in lines X.001-X.033 in table X.

Table 72:

This table discloses the 33 compounds 72.001 to 72.033 of the formula (Iad) wherein n is 2, and $R_2$ is $SCF_3$, $R_1$ is ethyl, $R_4$ is hydrogen and Q is as defined in lines X.001-X.033 in table X.

Table 73:

This table discloses the 33 compounds 73.001 to 73.033 of the formula (Iae):

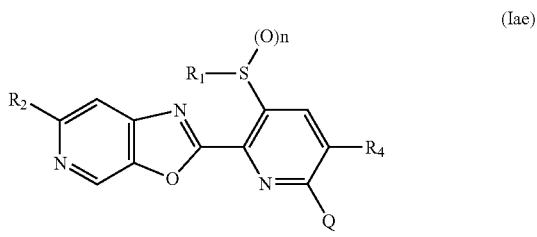

wherein n is 0, and $R_2$ is $CF_3$, $R_1$ is ethyl, $R_4$ is hydrogen and Q is as defined in lines X.001-X.033 in table X. For example, compound 73.024 has the following structure:

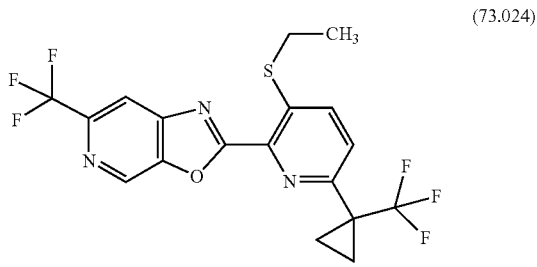 [SMILES: CCSc1ccc(C2(C(F)(F)F)CC2)nc1-c1nc2cc(C(F)(F)F)ncc2o1]

Table 74:

This table discloses the 33 compounds 74.001 to 74.024 of the formula (Iae) wherein n is 2, and $R_2$ is $CF_3$, $R_1$ is ethyl, $R_4$ is hydrogen and Q is as defined in lines X.001-X.033 in table X.

Table 75:

This table discloses the 33 compounds 75.001 to 75.033 of the formula (Iae) wherein n is 0, and $R_2$ is $CF_2CF_3$, $R_1$ is ethyl, $R_4$ is hydrogen and Q is as defined in lines X.001-X.033 in table X.

Table 76:

This table discloses the 33 compounds 76.001 to 76.033 of the formula (Iae) wherein n is 2, and $R_2$ is $CF_2CF_3$, $R_1$ is ethyl, $R_4$ is hydrogen and Q is as defined in lines X.001-X.033 in table X.

Table 77:

This table discloses the 33 compounds 77.001 to 77.033 of the formula (Iae) wherein n is 0, and $R_2$ is $CF(CF_3)_2$, $R_1$ is ethyl, $R_4$ is hydrogen and Q is as defined in lines X.001-X.033 in table X.

Table 78:

This table discloses the 33 compounds 78.001 to 78.033 of the formula (Iae) wherein n is 2, and $R_2$ is $CF(CF_3)_2$, $R_1$ is ethyl, $R_4$ is hydrogen and Q is as defined in lines X.001-X.033 in table X.

Table 79:

This table discloses the 33 compounds 79.001 to 79.033 of the formula (Iae) wherein n is 0, and $R_2$ is $SCF_3$, $R_1$ is ethyl, $R_4$ is hydrogen and Q is as defined in lines X.001-X.033 in table X.

Table 80:

This table discloses the 33 compounds 80.001 to 80.033 of the formula (Iae) wherein n is 2, and $R_2$ is $SCF_3$, $R_1$ is ethyl, $R_4$ is hydrogen and Q is as defined in lines X.001-X.033 in table X.

Table 81:

This table discloses the 33 compounds 81.001 to 81.033 of the formula (Iaf):

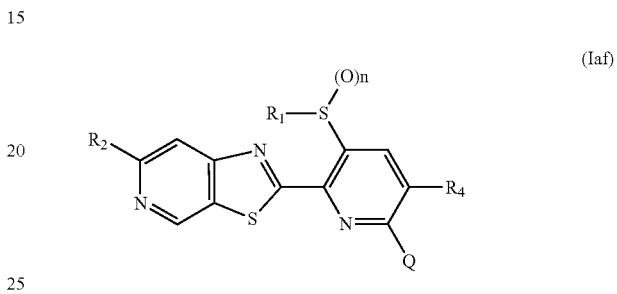

wherein n is 0, and $R_2$ is $CF_3$, $R_1$ is ethyl, $R_4$ is hydrogen and Q is as defined in lines X.001-X.033 in table X. For example, compound 81.007 has the following structure:

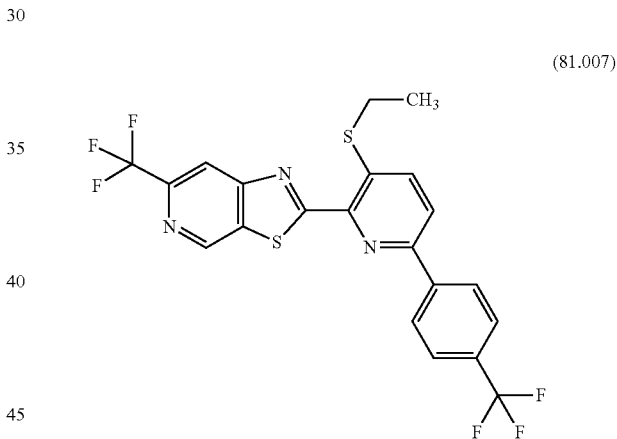

Table 82:

This table discloses the 33 compounds 82.001 to 82.024 of the formula (Iaf) wherein n is 2, and $R_2$ is $CF_3$, $R_1$ is ethyl, $R_4$ is hydrogen and Q is as defined in lines X.001-X.033 in table X.

Table 83:

This table discloses the 33 compounds 83.001 to 83.033 of the formula (Iaf) wherein n is 0, and $R_2$ is $CF_2CF_3$, $R_1$ is ethyl, $R_4$ is hydrogen and Q is as defined in lines X.001-X.033 in table X.

Table 84:

This table discloses the 33 compounds 84.001 to 84.033 of the formula (Iaf) wherein n is 2, and $R_2$ is $CF_2CF_3$, $R_1$ is ethyl, $R_4$ is hydrogen and Q is as defined in lines X.001-X.033 in table X.

Table 85:

This table discloses the 33 compounds 85.001 to 85.033 of the formula (Iaf) wherein n is 0, and $R_2$ is $CF(CF_3)_2$, $R_1$ is ethyl, $R_4$ is hydrogen and Q is as defined in lines X.001-X.033 in table X.

Table 86:

This table discloses the 33 compounds 86.001 to 86.033 of the formula (Iaf) wherein n is 2, and $R_2$ is $CF(CF_3)_2$, $R_1$ is ethyl, $R_4$ is hydrogen and Q is as defined in lines X.001-X.033 in table X.

Table 87:

This table discloses the 33 compounds 87.001 to 87.033 of the formula (Iaf) wherein n is 0, and $R_2$ is $SCF_3$, $R_1$ is ethyl, $R_4$ is hydrogen and Q is as defined in lines X.001-X.033 in table X.

Table 88:

This table discloses the 33 compounds 88.001 to 88.033 of the formula (Iaf) wherein n is 2, and $R_2$ is $SCF_3$, $R_1$ is ethyl, $R_4$ is hydrogen and Q is as defined in lines X.001-X.033 in table X.

The compounds of formula I according to the invention are preventively and/or curatively valuable active ingredients in the field of pest control, even at low rates of application, which have a very favourable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. porrum, A. ascalonicum, A. fistulosum*), *Anthriscus cerefolium, Apium graveolus, Asparagus officinalis, Beta vulgarus, Brassica* spp. (*B. oleracea, B. pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Del-*

*phinium, Monarda, Phlox, Rudbeckia, Sedum, Petunia, Viola, Impatiens, Geranium, Chrysanthemum, Ranunculus, Fuchsia, Salvia, Hortensia,* rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. nemoralis*); *ochlodina; Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides.*

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins.

Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
| --- | --- | --- |
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
| --- | --- | --- |
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |

TABLE B-continued

Examples of native woodborers of economic importance.

| Family | Species | Host or Crop Infested |
|---|---|---|
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Garyllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:
Of the order Anoplurida: *Haematopinus* spp., *Linognathus* spp., *Pediculus* spp. and *Phtirus* spp., *Solenopotes* spp.
Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus,*

*Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
   active ingredient: 1 to 95%, preferably 60 to 90%
   surface-active agent: 1 to 30%, preferably 5 to 20%
   liquid carrier: 1 to 80%, preferably 1 to 35%

Dusts:
   active ingredient: 0.1 to 10%, preferably 0.1 to 5%
   solid carrier: 99.9 to 90%, preferably 99.9 to 99%

Suspension Concentrates:
   active ingredient: 5 to 75%, preferably 10 to 50%
   water: 94 to 24%, preferably 88 to 30%
   surface-active agent: 1 to 40%, preferably 2 to 30%

Wettable Powders:
   active ingredient: 0.5 to 90%, preferably 1 to 80%
   surface-active agent: 0.5 to 20%, preferably 1 to 15%
   solid carrier: 5 to 95%, preferably 15 to 90%

Granules:
   active ingredient: 0.1 to 30%, preferably 0.1 to 15%
   solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mpt." means melting point in ° C. Free radicals represent methyl groups. $^{1}$H NMR measurements were recorded on a Brucker 400 MHz spectrometer, chemical shifts are given in ppm relevant to a TMS standard. Spectra measured in deuterated solvents as indicated.

LCMS Methods:

Method 1:

Spectra were recorded on a Mass Spectrometer from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+ 0.05% HCOOH, B=Acetonitrile+0.05% HCOOH, gradient: 10-100% B in 1.2 min; Flow (mL/min) 0.85

Example H1: 2-[3-ethylsulfonyl-6-[3-(trifluoromethyl)pyrazol-1-yl]-2-pyridyl]-3-methyl-6-(trifluoromethyl)imidazo[4,5-c]pyridine (Compound P3, Table P)

(Compound P3, table P)

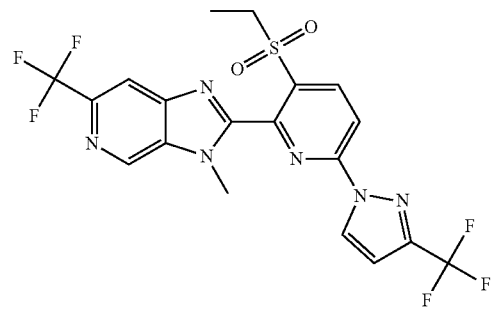

Step A: tert-butyl N-[4-amino-6-(trifluoromethyl)-3-pyridyl]carbamate

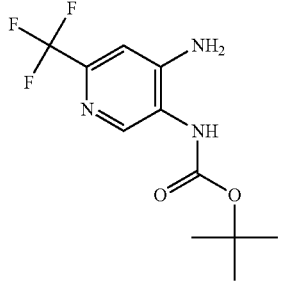 [SMILES: CC(C)(C)OC(=O)Nc1cnc(C(F)(F)F)cc1N]

To a solution of 6-(trifluoromethyl)pyridine-3,4-diamine (3.14 g, 17.73 mmol, prepared as described in U.S. Pat. No. 7,767,687) in tetrahydrofurane (50 ml) was added tert-butoxycarbonyl tert-butyl carbonate (4.64 g, 21.27 mmol) and the mixture was stirred at 50° C. After 8 hours, a further 1.1 g (5.0 mmol) of tert-butoxycarbonyl tert-butyl carbonate was added, and stirring at 50° C. continued for a further 4 hours. The reaction mixture was then concentrated in vacuo, and the brown residue was suspended in dichloromethane, filtered and dried in vacuo to give the title compound as white crystals. LCMS (method A): retention time: 0.79 min; 278 (M+H).

Step B: tert-butyl N-[4-amino-6-(trifluoromethyl)-3-pyridyl]-N-methyl-carbamate

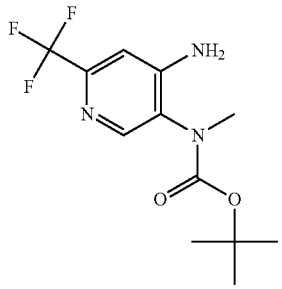 [SMILES: CN(C(=O)OC(C)(C)C)c1cnc(C(F)(F)F)cc1N]

To a stirred suspension of sodium hydride (0.648 g, 14.85 mmol) in 30 ml N,N-dimethylformamide, tert-butyl N-[4-amino-6-(trifluoromethyl)-3-pyridyl]carbamate (3.92 g, 14.14 mmol) dissolved in 20 ml N,N-dimethylformamide was added dropwise over a period of 20 min at 20-25° C. After 15 min stirring at ambient temperature, iodomethane (2.21 g, 15.55 mmol) was added. After 30 min at ambient temperature the mixture was poured onto 200 ml water, extracted twice with ethyl acetate, and the combined organic fractions washed successively with water and brine, dried over Na$_2$SO$_4$ and concentrated in vacuo. The crude product was recrystallized from ethyl acetate/heptane to give the title compound (3.18 g) as white crystals. LCMS (method A): retention time: 0.85 min; 292 (M+H).

Step C: N3-methyl-6-(trifluoromethyl)pyridine-3,4-diamine

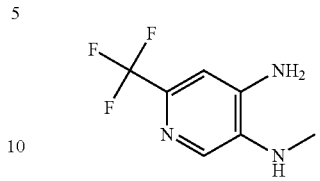

To a clear, colorless solution of tert-butyl N-[4-amino-6-(trifluoromethyl)-3-pyridyl]-N-methyl-carbamate (3.53 g, 12.119 mmol) in dioxane, hydrogen chloride (18 mL of a 2M solution in water, 36.36 mmol) was added and the mixture was heated to reflux. After gas evolution had ceased, the reaction mixture was cooled to room temperature, and treated with solid sodium hydrogen carbonate (3.1 g, 36.9 mmol). The slurry was diluted with water and extracted twice with ethyl acetate. The combined organic layers were washed successively with water and brine, dried over Na$_2$SO$_4$ and concentrated in vacuo to give 2.25 g of the title compound as colorless crystals, Mpt 138-140° C. LCMS (method A): retention time 0.24 min, 192 (M+H).

Alternatively, N3-methyl-6-(trifluoromethyl)pyridine-3,4-diamine can be obtained by the following procedure:

To a solution of 6-(trifluoromethyl)pyridine-3,4-diamine (2.0 g, 12.2 mmol) and potassium carbonate (3.2 g, 23.1 mmol) in acetonitrile (10 mL) was added iodomethane (0.8 mL). The reaction mixture was stirred at 30° C. for 18 hours. Potassium carbonate was filtered off, the filtrate was dried in vacuo and purified with chromatography column on silica gel eluting with (petroleum:ethyl acetate=4:3) to afford the title compound as a light yellow solid (0.32 g). $^1$H NMR (400 MHz, DMSO-d$_6$): δ (ppm) 7.57 (s, 1H), 6.83 (s, 1H), 5.82 (s, 2H), 5.23 (d, J=4.8 Hz, 1H), 2.80 (d, J=4.8 Hz, 3H). $^{19}$F NMR (300 MHz, DMSO-d6): δ (ppm) −60.12 (s, 3F).

Step D: N-[4-amino-6-(trifluoromethyl)-3-pyridyl]-3-ethylsulfonyl-N-methyl-pyridine-2-carboxamide and 3-ethylsulfonyl-N-[5-(methylamino)-2-(trifluoromethyl)-4-pyridyl]pyridine-2-carboxamide

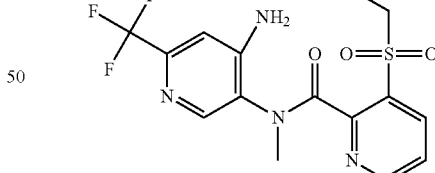

and

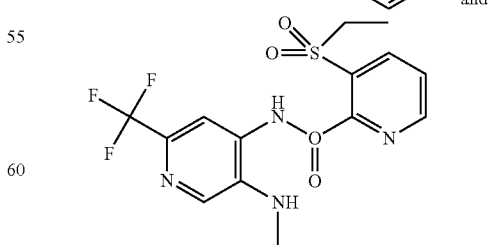

To a solution of N3-methyl-6-(trifluoromethyl)pyridine-3,4-diamine (16.70 g, 87.37 mmol) in THF (167.0 mL) was added Et$_3$N (22.32 g, 218.4 mmol). The reaction mixture cooled to 0° C. and 3-ethylsulfonylpyridine-2-carbonyl chloride (18.37 g, 78.63 mmol, prepared as described in WO 2013 018928) dissolved in dichloromethane (170 mL) was added dropwise at 0-10° C. to the mixture over 1 hour. After 1.5 hours LC/MS detected desired product at Rt=0.74. The ice-bath was removed and the reaction mixture was allowed to warm up to ambient temperature and stirred for 12 hours. The reaction mixture was then diluted with saturated NH$_4$Cl, the organic phase separated, and the aqueous phase back extracted with dichloromethane. The combined organic phases were washed with water, brine, dried over Na$_2$SO$_4$, filtered and concentrated in vacuo to give the crude product. The crude product was dissolved in dichloromethane and adsorbed on teflon bulk sorbents, and purified over a silica gel cartridge (Rf200) eluting with cyclohexane/ethyl acetate. This gave the crude title product as a mixture of amide region isomers that was used in the next step without further purification.

LCMS (method 1); Rt=0.73 min, [M+H] 389 and 0.8 min [M+H] 389.

Step E: 2-(3-ethylsulfonyl-2-pyridyl)-3-methyl-6-(trifluoromethyl)imidazo[4,5-c]pyridine

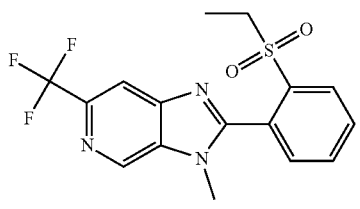 [SMILES: CCS(=O)(=O)c1ccccc1-c1nc2cc(C(F)(F)F)ncc2n1C]

A yellow solution of the crude product mixture from step D (26.72 g, 68.80 mmol) in acetic 270 mL, was stirred at 120° C. over night. After cooling, the mixture was diluted with toluene and concentrated in vacuo. The crude product was dissolved in dichloromethane and adsorbed on teflon bulk sorbents, and purified over a silica gel cartridge (TORENT) eluting with heptane:EtOAc to give the title product as beige solid.

LCMS (method 1): retention time 0.78 minutes, (M+H)=371. $^1$H NMR (400 MHz, CHLOROFORM-d) δ ppm: 1.36 (t, J=7.3 Hz, 3H); 3.77 (q, J=7.3 Hz, 2H); 3.90 (s, 3H); 7.77 (dd, J=8.1, 4.8 Hz, 1H); 8.12 (s, 1H); 8.55 (dd, J=8.1, 1.8 Hz, 1H); 9.00 (s, 1H); 9.02 (dd, J=4.8, 1.8 Hz, 1H).

Step F: 2-(3-ethylsulfonyl-1-oxido-pyridin-1-ium-2-yl)-3-methyl-6-(trifluoromethyl)imidazo[4,5-c]pyridine (A)

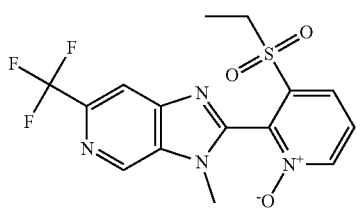

(A)

Method A:

To a solution of 2-(3-ethylsulfonyl-2-pyridyl)-3-methyl-6-(trifluoromethyl)imidazo[4,5-c]pyridine (18.70 g, 50.49 mmol) in dichloromethane (187.0 mL) was added meta-chloroperbenzoic acid (13.69 g, 55.53 mmol). The yellow solution was stirred at ambient temperature for 18 hours. After this time, the reaction mixture was cooled to ambient temperature, and diluted with aqueous sodium thiosulfate solution. The reaction mixture was extracted with dichloromethane, the combined organic fractions washed with Na$_2$CO$_3$, dried over MgSO$_4$, and concentrated in vacuo. The crude product was dissolved in dichloromethane and adsorbed on teflon bulk sorbents, and purified over a silica gel cartridge (TORENT) eluting with heptane/ethyl acetate and then dichloromethane:methanol. This gave the title product as the first eluting product.

LCMS (method 1): retention time 0.72 min, (M+H)=387. $^1$H NMR (400 MHz, CHLOROFORM-d) δ ppm; 1.35 (t, J=7.5 Hz, 3H); 3.39-3.52 (m, 1H); 3.66-3.82 (m, 1H); 3.87 (s, 3H); 7.71 (dd, J=8.1, 6.6 Hz, 1H); 8.00 (dd, J=8.1, 0.7 Hz, 1H); 8.13 (d, J=0.7 Hz, 1H); 8.55 (dd, J=6.6, 0.7 Hz, 1H) 9.03 (s, 1H).

As second eluting product was 2-(3-ethylsulfonyl-2-pyridyl)-3-methyl-5-oxido-6-(trifluoromethyl)imidazo[4,5-c]pyridin-5-ium (B)

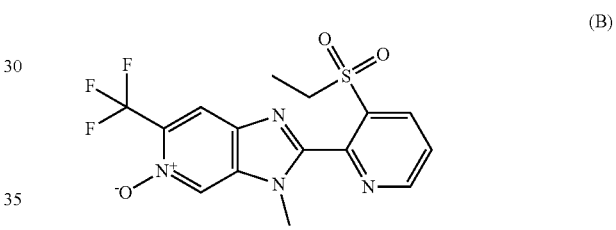

(B)

LCMS (method 1): retention time 0.64 min, (M+H)=387. $^1$H NMR (400 MHz, CHLOROFORM-d) δ ppm: 1.37 (t, J=7.5 Hz, 3H); 3.76 (q, J=7.5 Hz, 2H); 3.77 (s, 3H); 7.77 (dd, J=8.1, 4.8 Hz, 1H); 8.09 (s, 1H); 8.55 (dd, J=8.1, 1.5 Hz, 1H); 8.71 (s, 1H); 9.01 (dd, J=4.8, 1.5 Hz, 1H).

As third eluting product was isolated 2-(3-ethylsulfonyl-1-oxido-pyridin-1-ium-2-yl)-3-methyl-5-oxido-6-(trifluoromethyl)imidazo[4,5-c]pyridin-5-ium (C)

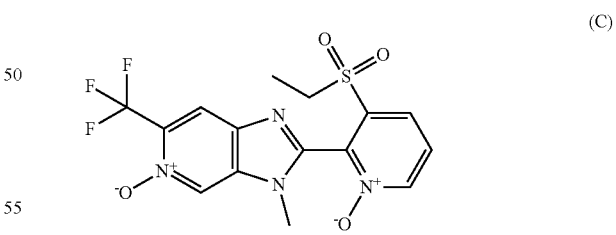

(C)

LCMS (method 1): retention time 0.55 min, (M+H)=403. $^1$H NMR (400 MHz, CHLOROFORM-d) δ ppm: 1.36 (t, J=7.3 Hz, 3H); 3.33-3.54 (m, 1H); 3.60-3.80 (m, 1H); 7.72 (dd, J=8.1, 6.6 Hz, 1H); 7.99 (dd, J=8.1, 0.7 Hz, 1H); 8.10 (s, 1H); 8.54 (dd, J=6.6, 0.7 Hz, 1H); 8.68 (s, 1H).

The ratio of the products was (A):(B):(C) 9:15:1.

Method B:

To a solution of 2-(3-ethylsulfonyl-2-pyridyl)-3-methyl-6-(trifluoromethyl)imidazo[4,5-c]pyridine (1.00 g, 2.70 mmol) and urea hydrogen peroxide (0.288 g, 1.10 eq, 2.97 mmol) in dichloromethane (10.0 mL) was slowly added trifluoroacetic acid anhydride (1.15 g, 0.759 mL, 5.40 mmol) at 0° C. After 30 min the ice-bath was removed and the reaction mixture was allowed to warm to ambient temperature.

LC/MS after 3 hours detected desired product at Rt=0.72, product B at Rt=0.64, and product D at Rt=0.55 It was stirred over the weekend at ambient temperature. Work-up and purification according to method A gave the same three products (A):(B):(C) in a ratio of 9:3:1.

Step G: 2-(6-chloro-3-ethylsulfonyl-2-pyridyl)-3-methyl-6-(trifluoromethyl)imidazo[4,5-c]pyridine

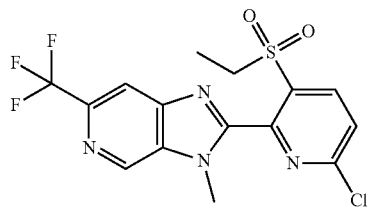 [SMILES: CCS(=O)(=O)c1ccc(Cl)nc1-c1nc2cc(C(F)(F)F)ncc2n1C]

2-(3-ethylsulfonyl-1-oxido-pyridin-1-ium-2-yl)-3-methyl-6-(trifluoromethyl)imidazo[4,5-c]pyridine (1.38 g, 1.00 eq, 3.57 mmol) and phosphoryl chloride (29.61 g, 18 mL, 53.5 eq, 191.2 mmol) were mixed in micro wave vial and heated at 130° C. for 6 hours in the microwave. LC/MS after this time showed reaction completion. The reaction mixture was concentrated in vacuo and purified over silica gel cartridge (Rf200), eluting with cyclohexane:ethyl acetate to give the title compound as a white solid:

LCMS (method 1): retention time 0.95 minutes, (M+H)=405/407. $^1$H NMR (400 MHz, CHLOROFORM-d) δ ppm: 1.41 (t, J=7.5 Hz, 3H); 3.64 (q, J=7.5 Hz, 2H); 4.11 (s, 3H); 7.89 (d, J=8.4 Hz, 1H); 8.49 (d, J=8.4 Hz, 1H); 9.65 (s, 1H).

Step H: 2-[3-ethylsulfonyl-6-[3-(trifluoromethyl)pyrazol-1-yl]-2-pyridyl]-3-methyl-6-(trifluoromethyl)imidazo[4,5-c]pyridine (Compound P3, Table P)

(Compound P3, table P)

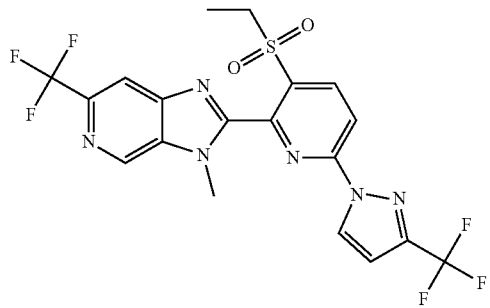

A solution of 3-(trifluoromethyl)-1H-pyrazole (0.034 g, 0.25 mmol) in DMF (2.0 mL, 26 mmol) was cooled to 0° C. and treated with sodium hydride (60% in oil, 0.013 g, 0.32 mmol). The reaction was stirred 20 min at 0° C. and then treated with 2-(6-chloro-3-ethylsulfonyl-2-pyridyl)-3-methyl-6-(trifluoromethyl)imidazo[4,5-c]pyridine (0.10 g, 0.25 mmol) and the reaction allowed to warm and stirred at ambient temperature. LCMS showed reaction completion after 30 min. The reaction was diluted with tert-butyl dimethyl ether, and then quenched with sat. NaHCO₃ sol. The organic layer was separated, washed 2× with water and brine, dried over Na₂SO₄, filtered and concentrated in vacuo. The crude product was dissolved in dichloromethane, adsorbed onto teflon bulk sorbents, and then purified over a silica gel cartridge (Rf200), eluting with cyclohexane/ethyl acetate, to give the title compound as a white solid. Mpt 261-263° C.

LCMS (method 1): retention time 1.07 min, (M+H)=505. $^1$H NMR (400 MHz, CHLOROFORM-d) δ ppm: 1.38 (t, J=7.5 Hz, 3H); 3.73 (q, J=7.5 Hz, 2H); 3.93 (s, 3H); 6.80 (d, J=2.6 Hz, 1H); 8.15 (d, J=0.7 Hz, 1H); 8.45 (d, J=8.8 Hz, 1H); 8.59 (dd, J=2.6, 0.92 Hz, 1H) 8.68 (d, J=8.8 Hz, 1H) 9.04 (s, 1H).

Example H2: 2-[6-(4-chlorophenyl)-3-ethylsulfonyl-2-pyridyl]-3-methyl-6-(trifluoromethyl)imidazo[4,5-c]pyridine (Compound P1, Table P)

(Compound P1, table P)

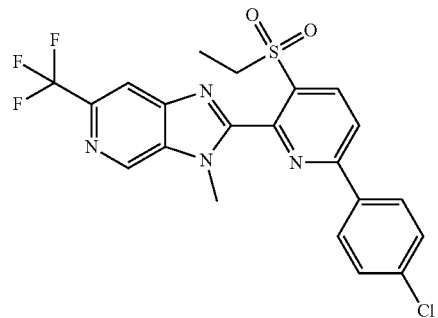

In a supelco vial, 2-(6-chloro-3-ethylsulfonyl-2-pyridyl)-3-methyl-6-(trifluoromethyl)imidazo[4,5-c]pyridine (Step G, example P1, 0.04 g, 0.1 mmol) dissolved in 1,4-dioxane (1 mL) was treated with (4-chlorophenyl)boronic acid (0.02 g, 0.1 mmol) and anhydrous K₂CO₃ (0.04 g, 0.3 mmol) and the mixture purged with argon for 10 min. Then, palladium-tris-triphenylphosphine (0.01 g, 0.01 mmol) was added and the solution heated at 100° C. LCMS analysis after 4 hours showed reaction completion. The reaction mixture was diluted with water and ethyl acetate, the organic layer was separated, washed with brine, dried over Na₂SO₄, filtered and evaporated and concentrated in vacuo. The crude product was dissolved in dichloromethane, adsorbed onto teflon bulk sorbents, and then purified over a silica gel cartridge (Rf200), eluting with cyclohexane/ethyl acetate, to give the title compound as a yellow solid. Mpt 255-256° C.

LCMS (method 1): retention time 1.11 min, (M+H)=481/483. ¹H NMR (400 MHz, CHLOROFORM-d) δ ppm: 1.39 (t, J=7.5 Hz, 3H); 3.79 (q, J=7.5 Hz, 2H); 3.95 (s, 3H); 7.51 (d, J=8.8 Hz, 2H); 8.06 (d, J=8.8 Hz, 2H); 8.11 (d, J=8.4 Hz, 1H); 8.15 (s, 1H); 8.57 (d, J=8.4 Hz, 1H); 9.02 (s, 1H).

Example H3: 2-[3-ethylsulfonyl-6-[(E)-2-[2-(trifluoromethyl)phenyl]vinyl]-2-pyridyl]-3-methyl-6-(trifluoromethyl)imidazo[4,5-c]pyridine (Compound P2, Table P)

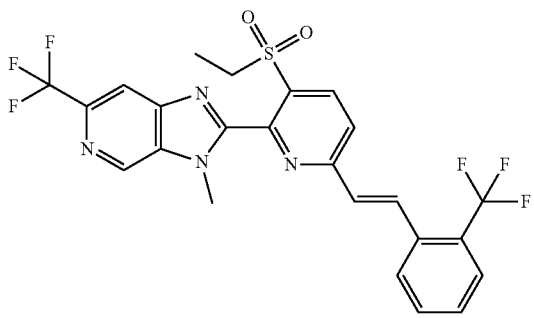

(compound P2, table P)

In a microwave vial, 2-(6-chloro-3-ethylsulfonyl-2-pyridyl)-3-methyl-6-(trifluoromethyl)imidazo[4,5-c]pyridine (Step G, example P1, 0.10 g, 0.25 mmol), anhydrous K₂CO₃ (0.068 g, 0.49 mmol), 2-(trifluoromethyl)styrene (0.043 g, 0.037 mL, 0.25 mmol) dissolved in acetonitrile were degassed with argon. To this mixture was added palladium(II)acetate (0.0051 g, 0.022 mmol) and the mixture then heated for 45 min at 140° C. after this time, a further portion of 2-(trifluoromethyl)styrene (0.074 mL) and palladium (II)acetate (0.0028 g, 0.050 eq, 0.012 mmol) were added and the mixture heated in the microwave 1 hour at 140° C. After this time, the reaction mixture was filtered over hyflo, and the filtrate diluted with ethyl acetate and washed successively with 1N HCl, water and brine, dried over Na₂SO₄, filtered and concentrated in vacuo. The crude product was dissolved in dichloromethane, adsorbed onto teflon bulk sorbents, and then purified over a silica gel cartridge (Rf200), eluting with cyclohexane/ethyl acetate. Further purification by reversed phase HPLC gave the title compound as white foam.

LCMS (method 1): retention time 1.14 min, (M+H)=541. ¹H NMR (400 MHz, CHLOROFORM-d) δ ppm: 1.40 (t, J=7.3 Hz, 3H); 3.86 (q, J=7.34 Hz, 2H); 4.00 (s, 3H); 7.24 (d, J=15.7 Hz, 1H); 7.46-7.52 (m, 1H); 7.62 (t, J=7.5 Hz, 1H); 7.71-7.77 (m, 2H) 7.85 (d, J=7.75 Hz, 1H) 8.14 (s, 1H) 8.25 (dd, J=15.7, 2.20 Hz, 1H) 8.51 (d, J=8.4 Hz, 1H) 9.03 (s, 1H).

Example H4: 2-[3-ethylsulfonyl-5-(trifluoromethyl)-6-[4-(trifluoromethyl)phenyl]-2-pyridyl]-3-methyl-6-(trifluoromethyl)imidazo[4,5-c]pyridine (Compound P4, Table P))

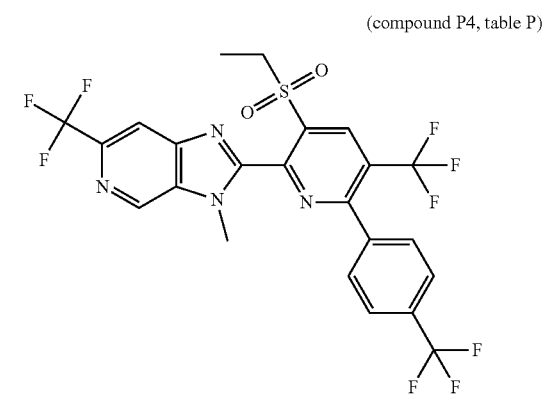 [SMILES: CCS(=O)(=O)c1cc(C(F)(F)F)c(-c2ccc(C(F)(F)F)cc2)nc1-c1nc2cc(C(F)(F)F)ncc2n1C]

(compound P4, table P)

Step A: Methyl 3-ethylsulfanyl-5-(trifluoromethyl)pyridine-2-carboxylate

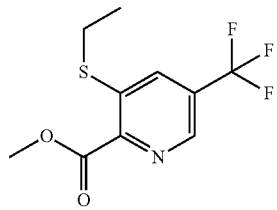 [SMILES: CCSc1cc(C(F)(F)F)cnc1C(=O)OC]

A solution of methyl 3-chloro-5-(trifluoromethyl)pyridine-2-carboxylate (30 g, 125 mmol, CAS Registry Number [655235-65-7]) was dissolved in DMF (630 mL), Sodium ethanethiolate (12.87 g, 138 mmol) was added in portions keeping the temperature below 20° C. The reaction mixture was allowed to stir overnight after which LCMS analysis showed reaction completion. The mixture was diluted with water, extracted with AcOEt (3 times), and the combined organic phases washed successively with saturated aqueous NH₄Cl and brine, dried over MgSO₄ and concentrated in vacuo. The crude title compound was used for the next step without further purification.

LCMS (method 1); Rt=0.96 min, [M+H] 266. ¹H NMR (400 MHz, CHLOROFORM-d) δ ppm: 1.43 (t, J=7.5 Hz, 3H); 3.00 (q, J=7.5 Hz, 2H); 4.04 (s, 3H); 7.87 (d, J=1.1 Hz, 1H); 8.66 (d, J=1.1 Hz, 1H).

Step B: methyl 3-ethylsulfonyl-5-(trifluoromethyl)pyridine-2-carboxylate

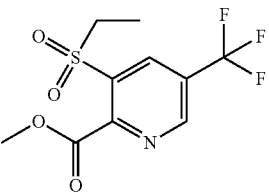 [SMILES: CCS(=O)(=O)c1cc(C(F)(F)F)cnc1C(=O)OC]

A solution of methyl 3-ethylsulfanyl-5-(trifluoromethyl)pyridine-2-carboxylate (5.94 g, 22.4 mmol) in dichloromethane (200 mL) was cooled to 0° C. To this solution was added m-CPBA (11.0 g, 44.8 mmol) in small portions at 0°. After 2 hours, the solution is allowed to warm to ambient and stirred for 3 hours at ambient temperature after which time LCMS showed reaction completion. The reaction mixture was poured onto NaHCO₃ aq. and saturated sodium thiosulfate aqueous solution. The mixture was then extracted with dichloromethane (3×), washed with brine, dried over MgSO₄ and concentrated in vacuo.

The crude product was purified by Combi flash chromatography eluting with a gradient of cyclohexane+0-30% ethyl acetate. This gave the title compound as a white solid.

LCMS (method 1); Rt=0.76 min, [M+H] 298. ¹H NMR (400 MHz, CHLOROFORM-d) δ ppm: 1.39 (t, J=7.5 Hz, 3H); 3.57 (q, J=7.5 Hz, 2H); 4.08 (s, 3H); 8.61 (d, J=1.8 Hz, 1H); 9.11 (d, J=1.8 Hz, 1H).

Step C: Methyl 3-ethylsulfonyl-1-oxido-5-(trifluoromethyl)pyridin-1-ium-2-carboxylate

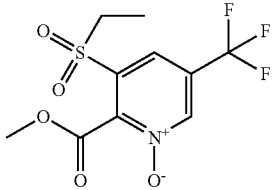 [SMILES: CCS(=O)(=O)c1cc(C(F)(F)F)c[n+]([O-])c1C(=O)OC]

A solution of methyl 3-ethylsulfonyl-5-(trifluoromethyl)pyridine-2-carboxylate (7.5 g, 25 mmol, prepared as described in) in dichloromethane (80 mL) was cooled to 0° C. and urea hydrogen peroxide complex (5.1 g, 53 mmol) added in small portions. To this mixture was added trifluoroacetic anhydride (11 g, 7.2 mL, 50.0 mmol) keeping the reaction temperature at 0° C. The reaction mixture was allowed to warm to rt and stirred overnight. After this time, the reaction was quenched with aqueous sodium hydrogen sulfite solution, and stirred for 15 min. The resulting mixture was poured onto 0.5 M HCl and extracted 3 times with dichloromethane. The combined organic extracts were washed with NaHCO₃ aqueous solution, dried over Na₂SO₄, filtered and concentrated in vacuo. The crude product was purified by Combi flash chromatography, eluting with a gradient of cyclohexane+0-100% ethyl acetate, to give the title compound as a white solid.

LCMS (method 1); Rt=0.70 min, [M+H] 314. ¹H NMR (400 MHz, CHLOROFORM-d) δ ppm: 1.39 (t, J=7.5 Hz, 3H); 3.38 (q, J=7.5 Hz, 2H); 4.08 (s, 3H); 7.93 (d, J=0.7 Hz, 1H); 8.62 (d, J=0.7 Hz, 1H).

Step D: Methyl 6-chloro-3-ethylsulfonyl-5-(trifluoromethyl)pyridine-2-carboxylate

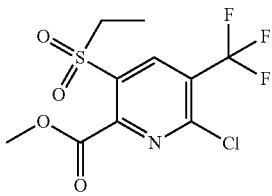 [SMILES: CCS(=O)(=O)c1cc(C(F)(F)F)c(Cl)nc1C(=O)OC]

A sample of methyl 3-ethylsulfonyl-1-oxido-5-(trifluoromethyl)pyridin-1-ium-2-carboxylate (1.43 g, 4.57 mmol) and phosphoryl chloride (24.3 mL) were placed in two microwave vials and the vials stirred at 130° C. for 6 hours in the microwave. After this time, the contents of the vials were combined and concentrated in vacuo. The crude product was purified over silica gel cartridge (Rf200) eluting with cyclohexane/ethyl acetate to give the title product as white crystals.

¹H NMR (400 MHz, CHLOROFORM-d) δ ppm: 1.39 (t, J=7.5 Hz, 3H); 3.55 (q, J=7.5 Hz, 2H); 4.07 (s, 3H); 8.61 (s, 1H).

Step E: Methyl 3-ethylsulfonyl-5-(trifluoromethyl)-6-[4-(trifluoromethyl)phenyl]pyridine-2-carboxylate

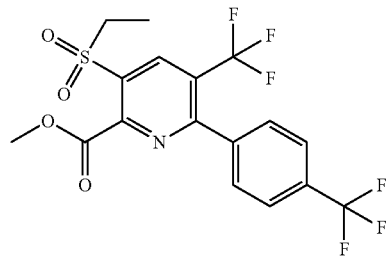 [SMILES: CCS(=O)(=O)c1cc(C(F)(F)F)c(-c2ccc(C(F)(F)F)cc2)nc1C(=O)OC]

A solution of methyl 6-chloro-3-ethylsulfonyl-5-(trifluoromethyl)pyridine-2-carboxylate (0.285 g, 0.86 mmol) in 1,4-dioxane (7 mL) was treated with [4-(trifluoromethyl)phenyl]boronic acid (0.212 g, 1.12 mmol) and anhydrous K₂CO₃ (0.356 g, 3.00 eq, 2.58 mmol) and the mixture purged with argon for 10 min. To this mixture was added tetrakis(triphenylphosphine)palladium(0) (0.0993 g, 0.100 eq, 0.0859 mmol) and the solution heated at 100° C. for 3 hr after which time LCMS showed good reaction conversion. The reaction mixture was diluted with NH₄Cl sat sol, water and ethyl acetate. The organic phase was separated, washed with brine, dried over Na₂SO₄, filtered and concentrated in vacuo. The crude product was dissolved in dichloromethane and adsorbed on teflon bulk sorbents. Purification over a silica gel cartridge (Rf200), eluting with cyclohexane/ethyl acetate gave the title compound as a white solid.

LCMS (method 1); Rt=1.09 min, [M+H] 442. ¹H NMR (400 MHz, CHLOROFORM-d) δ ppm: 1.44 (t, J=7.5 Hz, 3H); 3.59 (q, J=7.5 Hz, 2H); 4.06 (s, 3H); 7.70 (d, J=8.0 Hz, 2H); 7.78 (d, J=8.0 Hz, 2H); 8.73 (s, 1H).

Step F: 3-ethylsulfonyl-5-(trifluoromethyl)-6-[4-(trifluoromethyl)phenyl]pyridine-2-carboxylic acid

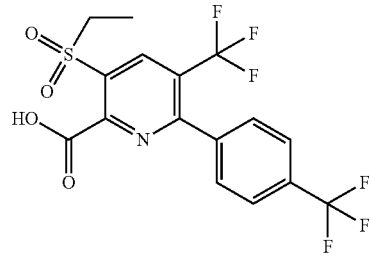 [SMILES: CCS(=O)(=O)c1cc(C(F)(F)F)c(-c2ccc(C(F)(F)F)cc2)nc1C(=O)O]

Methyl 3-ethylsulfonyl-5-(trifluoromethyl)-6-[4-(trifluoromethyl)phenyl]pyridine-2-carboxylate (0.28 g, 0.63 mmol) was dissolved in tetrahydrofuran/H₂O 3:1 (10 mL) and treated with lithium hydroxide hydrate (0.028 g, 0.67 mmol) at ambient temperature. LCMS analysis after stirring for 3 hours showed reaction. The reaction mixture was concentrated in vacuo and taken up in ethyl acetate and 10% aqueous HCl. The organic layer was separated and washed with brine, dried over Na₂SO₄, filtered and concentrated in vacuo to give the title compound as beige solid that was used in the next step without further purification.

LCMS (method 1); Rt=0.88 min, [M+H] 428. ¹H NMR (400 MHz, CHLOROFORM-d) δ ppm 1.42 (t, J=7.3 Hz, 3H): 3.75 (q, J=7.3 Hz, 2H): 4.98 (br. s., 1H); 7.70 (d, J=7.8 Hz, 2H); 7.79 (d, J=7.8 Hz, 2H): 8.86 (s, 1H).

Step G: 3-ethylsulfonyl-N-[5-(methylamino)-2-(trifluoromethyl)-4-pyridyl]-5-(trifluoromethyl)-6-[4-(trifluoromethyl)phenyl]pyridine-2-carboxamide and N-[4-amino-6-(trifluoromethyl)-3-pyridyl]-3-ethylsulfonyl-N-methyl-5-(trifluoromethyl)-6-[4-(trifluoromethyl)phenyl]pyridine-2-carboxamide

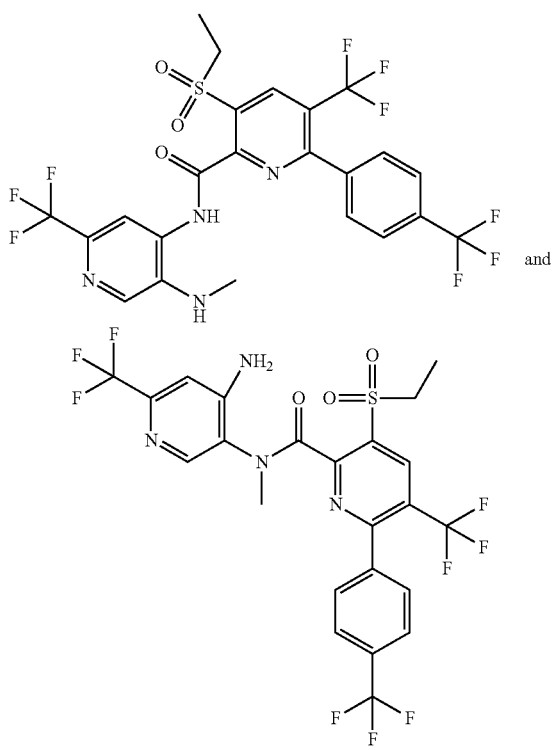

and

A solution of 3-ethylsulfonyl-5-(trifluoromethyl)-6-[4-(trifluoromethyl)phenyl]pyridine-2-carboxylic acid (0.10 g, 0.23 mmol), EDCl (0.049 g, 0.26 mmol) and N3-methyl-6-(trifluoromethyl)pyridine-3,4-diamine (0.049 g, 0.26 mmol, step C, example P1) in pyridine (3.0 mL) was stirred at 120° C. After 2 hours LC/MS showed sufficient reaction progress for work-up. The reaction mixture was poured onto water, and extracted with ethyl acetate (×3). The combined organic layers were washed with brine, dried over Na₂SO₄ and concentrated in vacuo. The crude product was dissolved in dichloromethane and adsorbed on teflon bulk sorbents. Purification over a silica gel cartridge (Rf200), eluting with cyclohexane/ethyl acetate Gradient gave a mixture of the title compounds as a yellow solid.

LCMS (method 1); Rt=1.10 min, [M+H] 601; Rt=1.14 min, [M+H] 601.

Step H: 2-[3-ethylsulfonyl-5-(trifluoromethyl)-6-[4-(trifluoromethyl)phenyl]-2-pyridyl]-3-methyl-6-(trifluoromethyl)imidazo[4,5-c]pyridine (Compound P4, Table P)

(compound P4, table P)

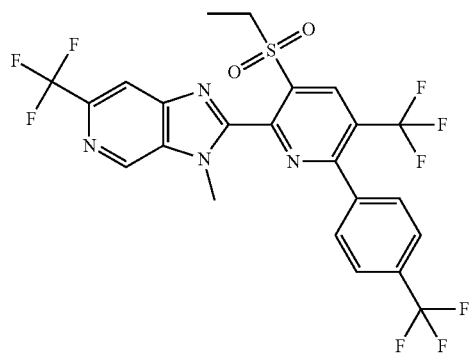

A yellow solution of 3-ethylsulfonyl-N-[5-(methylamino)-2-(trifluoromethyl)-4-pyridyl]-5-(trifluoromethyl)-6-[4-(trifluoromethyl)phenyl]pyridine-2-carboxamide and N-[4-amino-6-(trifluoromethyl)-3-pyridyl]-3-ethylsulfonyl-N-methyl-5-(trifluoromethyl)-6-[4-(trifluoromethyl)phenyl]pyridine-2-carboxamide: (0.055 g, 0.092 mmol) in acetic acid (1 mL) was stirred at 120° C. for 18 hours. LCMS analysis after this time showed reaction completion. The reaction mixture was cooled to ambient temperature, diluted with toluene and concentrated in vacuo. The crude product was dissolved in dichloromethane and adsorbed on teflon bulk sorbents. Purification over a silica gel cartridge (Rf200), eluting with a cyclohexane/ethyl acetate gradient gave a mixture of the title compounds as a white solid. Mpt. 140-142° C.

LCMS (method 1); Rt=1.17 min, [M+H] 583. ¹H NMR (400 MHz, CHLOROFORM-d) δ ppm 1.47 (t, J=7.5 Hz, 3H); 3.94 (q, J=7.5 Hz, 2H); 7.72-7.76 (m, 2H); 7.78-7.82 (m, 2H); 3.94 (q, J=7.34 Hz, 2H); 3.96 (s, 3H); 8.92 (s, 1H); 9.01 (s, 1H).

Example H5: 2-(6-cyclopropyl-3-ethylsulfonyl-2-pyridyl)-3-methyl-6-(trifluoromethyl)imidazo[4,5-c]pyridine (Compound P15, Table P)

(Compound P15, table P)

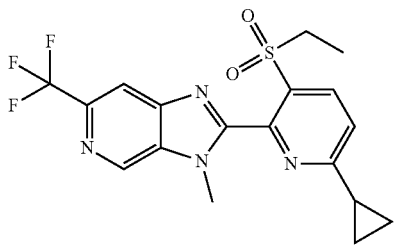

Step A: 3,6-dichloropyridine-2-carbonyl chloride

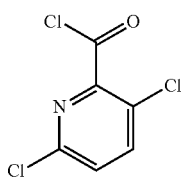 [SMILES: O=C(Cl)c1nc(Cl)ccc1Cl]

A sample of 3,6-dichloropyridine-2-carboxylic acid (5.00 g, 24.7 mmol) was diluted in dichloromethane (200 mL) and dimethylformamide (0.124 mL, 1.6 mmol) was added. To this solution was added oxalyl chloride (3.15 mL, 34.6 mmol) dropwise at room temperature over 10 min (gas evolution). The reaction mixture was stirred at room temperature, and after 2.5 h, a further 1 ml oxalyl chloride was added and stirring continued for 1 hr. After this time, the reaction mixture was concentrated in vacuo and used in the next step without further purification.

Step B: 3,6-dichloro-N-[5-(methylamino)-2-(trifluoromethyl)-4-pyridyl]pyridine-2-carboxamide

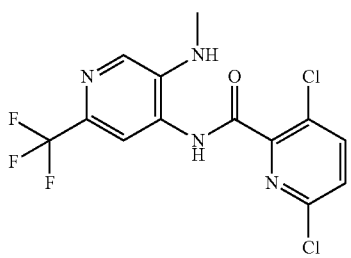 [SMILES: CNc1cnc(C(F)(F)F)cc1NC(=O)c1nc(Cl)ccc1Cl]

To a solution of N3-methyl-6-(trifluoromethyl)pyridine-3,4-diamine (52.0 g, 272 mmol) in tetrahydrofurane (260 mL) was added triethylamine (95.8 mL, 680 mmol). The red solution was cooled to 0° C. and 3,6-dichloropyridine-2-carbonyl chloride (51.5 g, 245 mmol) in dichloromethane (156 mL) was added dropwise at 0-10° C. over 90 min. The ice-bath was removed after 1 h and the mixture was stirred at room temperature. LC-MS analysis showed mainly desired mass after 2 hours. The reaction mixture was stirred overnight and then washed with NH$_4$Cl sat sol and the mixture was concentrated in vacuo to remove tetrahydrofurane. The residue was then extracted with 1.2 L dichloromethane (800 ml) ethylacetate and again 1 dichloromethane. The combined organic layers were dried over Na$_2$SO$_4$, filtered and concentrated in vacuo to give the title compound as a brown solid.

LCMS (method 1): 366 (M+H$^+$); retention time: 0.83 min.

Step C: 2-(3,6-dichloro-2-pyridyl)-3-methyl-6-(trifluoromethyl)imidazo[4,5-c]pyridine

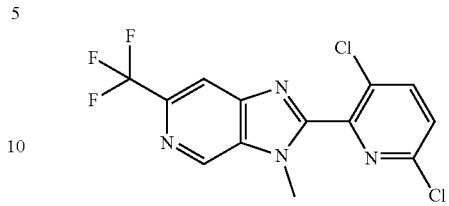

A yellow solution of 3,6-dichloro-N-[5-(methylamino)-2-(trifluoromethyl)-4-pyridyl]pyridine-2-carboxamide (99.3 g, 272 mmol) in acetic acid (298 mL) was stirred at 110° C. bath temperature for 16 hours. The reaction mixture was allowed to room temperature after which time LC-MS analysis showed desired mass. Toluene was added and the mixture was concentrated in vacuo. To the residue was added cyclohexane and dichloromethane and the mixture obtained was stirred under vacuum at 50° C. at 800 mbar. The slurry was further diluted with cyclohexane and the solid filtered at the pump. The cake was washed with cyclohexane (mixed with small amounts of DCM) and dried under vacuum. Toluene was added the mixture was evaporated and dried under vacuum at 60° C. and 20 mbar to remove traces of acetic acid, giving the title compound as a brown solid.

LCMS (method 1): 348 (M+H$^+$); retention time: 0.95 min.

$^1$H NMR (400 MHz, CHLOROFORM-d) δ ppm 4.04 (s, 3H) 7.51 (d, J=8.44 Hz, 1H) 7.93 (d, J=8.44 Hz, 1H) 8.19 (s, 1H) 8.99 (s, 1H)

Step D: 2-(6-chloro-3-ethylsulfanyl-2-pyridyl)-3-methyl-6-(trifluoromethyl)imidazo[4,5-c]pyridine

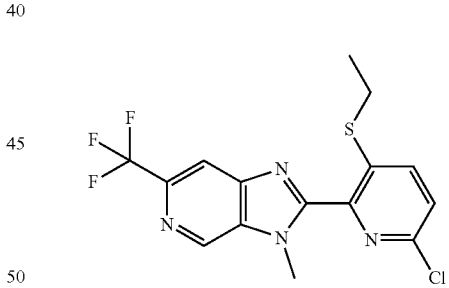

A sample of 2-(3,6-dichloro-2-pyridyl)-3-methyl-6-(trifluoromethyl)imidazo[4,5-c]pyridine (1.14 g, 3.28 mmol) was dissolved in tetrahydrofurane under argon. Sodium ethanethiol (0.311 g, 3.28 mmol) was added portionwise at room temperature. The brown reaction mixture was stirred at room temperature for 2 hours by which time LC-MS analysis showed reaction completion with formation of the desired product. The reaction mixture was treated with NH$_4$Cl followed by water and ethyl acetate. The organic layer was separated, washed with water and brine, dried over Na$_2$SO$_4$, filtered and concentrated in vacuo. The crude was purified by flash chromatography over silica gel to give the title compound as a beige solid.

LCMS (method 1): 373 (M+H+); retention time: 1.02 min.

1H NMR (400 MHz, CHLOROFORM-d) δ ppm 1.35 (t, J=7.34 Hz, 3H) 2.97 (q, J=7.34 Hz, 2H) 4.11 (s, 3H) 7.44 (d, J=8.44 Hz, 1H) 7.76 (d, J=8.44 Hz, 1H) 8.20 (d, J=0.73 Hz, 1H) 8.97 (s, 1H)

Step E: 2-(6-chloro-3-ethylsulfonyl-2-pyridyl)-3-methyl-6-(trifluoromethyl)imidazo[4,5-c]pyridine

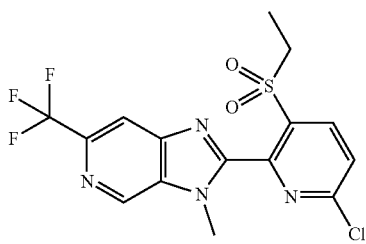 [SMILES: CCS(=O)(=O)c1ccc(Cl)nc1-c1nc2cc(C(F)(F)F)ncc2n1C]

At 0° C. m-CPBA (2.35 g, 10.5 mmol) was added to a solution of 2-(6-chloro-3-ethylsulfanyl-2-pyridyl)-3-methyl-6-(trifluoromethyl)imidazo[4,5-c]pyridine (1.86 g, 4.99 mmol) in chloroform (46.5 mL). After the addition the ice-bath was kept for 10 min and then the milky solution was allowed to warm to rt. The reaction mixture was stirred one night at room temperature. After this time a further portion of M-CPBA (1.12 g, 4.99 mmol) was added the mixture was stirred 2 hours at room temperature. LC-MS analysis showed the complexion of the reaction. Saturated sodium thiosulfate aqueous solution and sat NaHCO$_3$aq were added and the mixture stirred 1 hour. The organic layer was separated, extracted with NaHCO$_3$, dried over Na$_2$SO$_4$ and evaporated. The crude product was purified by flash chromatography over silica gel to give the title compound as a white solid.

LCMS (method 1): 406 (M+H+); retention time: 0.95 min.

$^1$H NMR (400 MHz, CHLOROFORM-d) δ ppm 1.37 (t, J=7.34 Hz, 3H) 3.79 (q, J=7.46 Hz, 2H) 3.94 (s, 3H) 7.75 (d, J=8.44 Hz, 1H) 8.11 (s, 1H) 8.47 (d, J=8.44 Hz, 1H) 9.00 (s, 1H)

Step F: 2-(6-cyclopropyl-3-ethylsulfonyl-2-pyridyl)-3-methyl-6-(trifluoromethyl)imidazo[4,5-c]pyridine (Compound P15, Table P)

(Compound P15, table P)

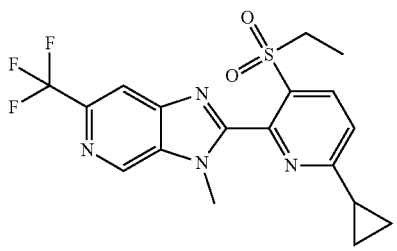

In a supelco vial 2-(6-chloro-3-ethylsulfonyl-2-pyridyl)-3-methyl-6-(trifluoromethyl)imidazo[4,5-c]pyridine (0.40 g, 0.99 mmol) was dissolved in 1,4-dioxane (10 mL, 120 mmol). Cyclopropylboronic acid (0.18 g, 2.0 mmol) and potassium carbonate (0.41 g, 3.0 mmol) were added and the mixture was purged with argon. Then tetrakis(triphenylphosphine) palladium (0.11 g, 0.099 mmol) was added, the vial was capped and the brown solution was heated at 100° C. for 19 hours. LC-MS analysis showed the formation of desired product. Water and ethyl acetate were added, the organic layer was separated, washed with brine, dried over Na$_2$SO$_4$, filtered and concentrated in vacuo. The crude obtained was purified by flash chromatography on silica gel. The mixture obtained was dissolved in ethylacetate and washed again with NaHCO$_3$. The organic layer was washed with brine, dried over Na$_2$SO$_4$, filtered and evaporated. The solid obtained was purified again by reverse phase to give the title compound as a white solid.

LCMS (method 1): 411 (M+H$^+$); retention time: 1.01 min.

1H NMR (400 MHz, CHLOROFORM-d) δ ppm 1.11-1.13 (m, 1H) 1.11-1.23 (m, 4H) 1.33 (t, J=7.34 Hz, 3H) 2.22 (ddd, J=7.70, 4.77, 2.93 Hz, 1H) 3.70 (q, J=7.34 Hz, 2H) 3.84 (s, 3H) 7.54 (d, J=8.44 Hz, 1H) 8.09 (s, 1H) 8.30 (d, J=8.44 Hz, 1H) 8.97 (s, 1H)

Example H6: 2-[6-(3,5-difluorophenyl)-3-ethylsulfonyl-2-pyridyl]-3-methyl-6-(trifluoromethyl)imidazo[4,5-c]pyridine (Compound P8, Table P)

(Compound P8, table P)

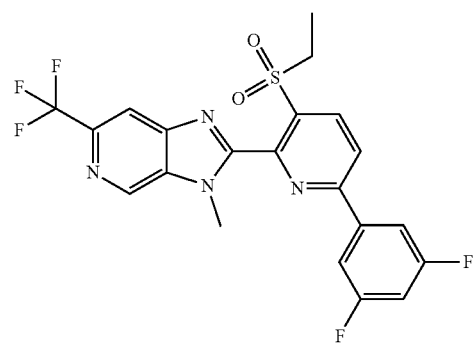

In a supelco vial, 2-(6-chloro-3-ethylsulfonyl-2-pyridyl)-3-methyl-6-(trifluoromethyl)imidazo[4,5-c]pyridine (100 mg, 0.2470 mmol), (3,5-difluorophenyl)boronic acid (46 mg, 0.2964 mmol) and potassium carbonate (102 mg, 0.7411 mmol) were dissolved in 1,4-dioxane (2.5 mL). The resulting mixture was flushed with argon over 5 minutes. After this time, tetrakis(triphenylphosphine) palladium (28 mg, 0.02470 mmol) was added and the vial was closed and heated at 95° C. for 16 hours. LC-MS analysis showed completion of the reaction. The reaction mixture was cooled to room temperature and quenched with water. The aqueous layer was extracted with ethyl acetate. The combined organic layers were washed with saturated solution of NaHCO$_3$ and saturated NaCl solution, dried over Na$_2$SO$_4$, filtered and concentrated in vacuo. The crude was purified by flash chromatography on silica gel to give the title compound as a yellow solid.

LCMS (method 1): 483 (M+H$^+$); retention time: 1.09 min.

$^1$H NMR (400 MHz, CHLOROFORM-d) δ ppm 1.42 (t, J=7.34 Hz, 3H) 3.84 (q, J=7.34 Hz, 2H) 3.99 (s, 3H) 7.00-7.05 (m, 1H) 7.68 (d, J=5.87 Hz, 2H) 8.12 (d, J=8.44 Hz, 1H) 8.17 (s, 1H) 8.64 (d, J=8.44 Hz, 1H) 9.06 (s, 1H)

Example H7: 2-[3-ethylsulfonyl-6-[3-(trifluoromethyl)pyrazol-1-yl]-2-pyridyl]-3-methyl-6-(trifluoromethylsulfanyl)imidazo[4,5-c]pyridine (Compound P9, Table P)

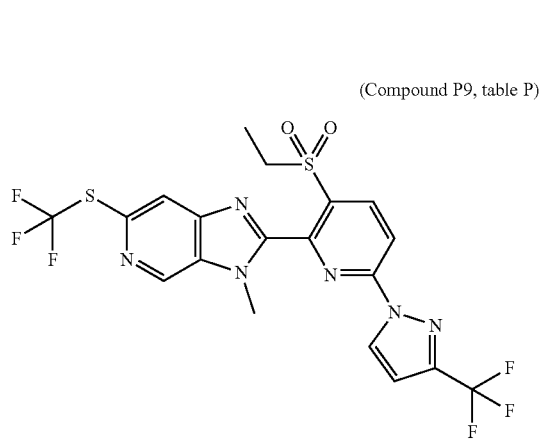 [SMILES: CCS(=O)(=O)c1ccc(-n2ccc(C(F)(F)F)n2)nc1-c1nc2cc(SC(F)(F)F)ncc2n1C]

(Compound P9, table P)

Step A: Methyl 3-ethylsulfonyl-6-[3-(trifluoromethyl)pyrazol-1-yl]pyridine-2-carboxylate

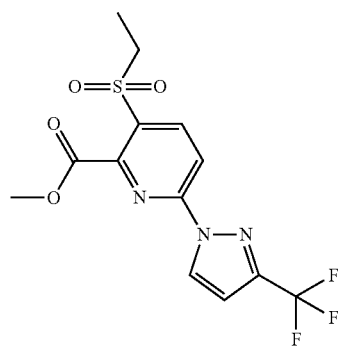 [SMILES: CCS(=O)(=O)c1ccc(-n2ccc(C(F)(F)F)n2)nc1C(=O)OC]

To a stirred solution of methyl 6-chloro-3-ethylsulfonyl-pyridine-2-carboxylate (526 mg, 2 mmol), 3-(trifluoromethyl)-1H-pyrazole (1.361 g, 10 mmol) in dioxane (25 mL) was added CuI (38 mg, 0.2 mmol), N,N'-Dimethylethanediamine (880 mg, 1 mmol) and potassium carbonate (1.38 g, 10 mmol). The reaction system was refluxed under a nitrogen atmosphere at 120° C. for 4 h. After cooling to room temperature, the reaction mixture was filtered and concentrated in vacuo. The crude product was purified by column chromatography on silica gel to give the title compound.

1HNMR (400 MHz, CDCl$_3$): δ ppm 1.36 (t, 3H), 3.49 (q, 2H), 4.06 (s, 3H), 6.69 (s, 1H), 8.26 (d, J=8.4 Hz, 1H), 8.44 (d, J=8.4 Hz, 1H), 8.68 (s, 1H); ESI-MS(+): 386 (M+Na)+

Step B: 3-ethylsulfonyl-6-[3-(trifluoromethyl)pyrazol-1-yl]pyridine-2-carboxylic acid To a stirred solution of methyl 3-ethylsulfonyl-6-[3-(trifluoromethyl)pyrazol-1-yl]pyridine-2-carboxylate (218 mg, 0.6 mmol) in THF (10 mL) was added NaOH (120 mg, 3 mmol), and H$_2$O (30 ml). The reaction system was stirred at room temperature for 2 h. After this time, the pH value was adjusted to 2 with HCl and the reaction mixture extracted with ethyl acetate three times. The combined organic layers were dried over anhydrous sodium sulfate, filtered and concentrated in vacuo to give the title compound.

1HNMR (400 MHz, DMSO-d6): δ ppm 1.18 (t, 3H), 3.54 (q, 2H), 7.12 (s, 1H), 8.21 (d, J=8.8 Hz, 1H), 8.53 (d, J=8.4 Hz, 1H), 8.86 (s, 1H); ESI-MS(+): 348 (M–H)–

Step C: 2-[3-ethylsulfonyl-6-[3-(trifluoromethyl)pyrazol-1-yl]-2-pyridyl]-3-methyl-6-(trifluoromethylsulfanyl)imidazo[4,5-c]pyridine (Compound P9, Table P)

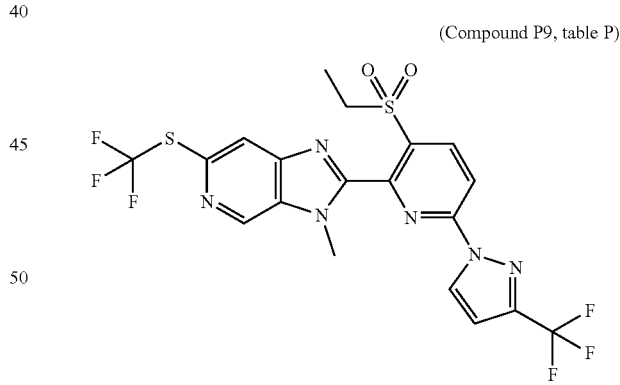

(Compound P9, table P)

To a stirred solution of 3-ethylsulfonyl-6-[3-(trifluoromethyl)pyrazol-1-yl]pyridine-2-carboxylic acid (180 mg, 0.52 mmol), N3-methyl-6-(trifluoromethylsulfanyl)pyridine-3,4-diamine (250 mg, 1.11 mmol) and HATU (0.78 g, 2 mmol) in DMF (30 mL) was added DIPEA (2 ml, 10 mmol). The reaction mixture was stirred at room temperature overnight. The reaction mixture was then diluted with ethyl acetate and H$_2$O, the organic layer was washed with brine, dried over anhydrous sodium sulfate, filtered and concentrated in vacuo. The crude product was used for the next step without further purification. The solution of the crude product in acetic acid (20 mL) was refluxed at 120° C. for 24 h. The reaction mixture was then evaporated to dryness. The residue was purified by chromatography on silica gel (petroleum:EtOAc=4:1) to afford the title compound as white solid.

LCMS (method 1): 537 (M+H+); retention time: 1.17 min.
1HNMR (400 MHz, CDCl3): δ (ppm) 1.37 (t, 3H), 3.73 (q, 2H), 3.90 (s, 3H), 6.79 (s, 1H), 8.14 (s, 1H), 8.45 (d, J=4.8 Hz, 1H), 8.65 (s, 1H), 8.67 (d, J=4.8 Hz, 1H), 8.98 (s, 1H); 19FNMR (376 MHz, CDCl3): δ (ppm) −46.40 (s, 3F), −68.19 (s, 3F)

Example 2 (3-ethylsulfonyl-6-pyrimidin-2-yl-2-pyridyl)-3-methyl-6-(trifluoromethylsulfanyl)imidazo[4,5-c]pyridine (Compound P10, Table P)

(Compound P10, table P)

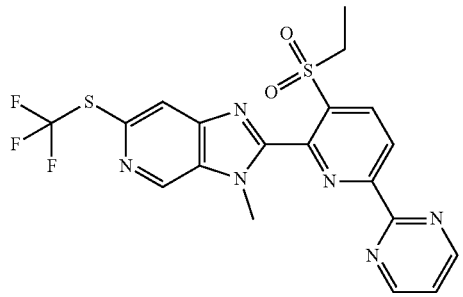

Step A: N-methyl-4-nitro-6-(trifluoromethylsulfanyl)pyridin-3-amine

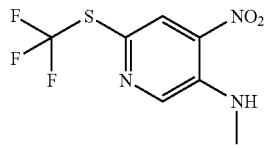

A sample of (bpy)CuSCF3 (14.4 g, 45 mmol) and 6-bromo-N-methyl-4-nitro-pyridin-3-amine (6.96 g, 30 mmol) in 120 ml of CH3CN was refluxed for 48 h under nitrogen. The reaction mixture was removed from the oil bath and allowed to cool to room temperature, and then filtered through SiO2. The silica gel was eluted with diethyl ether, and concentrated in vacuo. The residue was purified by silica gel column chromatography to give the title compound.

1HNMR (400 MHz, DMSO-d6): δ (ppm) 3.10 (d, J=5.2 Hz, 3H), 8.21 (s, 1H) 8.49 (q, 1H), 8.67 (s, 1H); 19FNMR (376 MHz, DMSO-d6): δ (ppm) −36.79 (s, 3F); ESI-MS: 252 (M−H)−.

Step B: N3-methyl-6-(trifluoromethylsulfanyl)pyridine-3,4-diamine

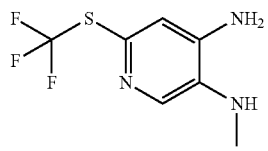

To a solution of N-methyl-4-nitro-6-(trifluoromethylsulfanyl)pyridin-3-amine (3.42 g, 13.5 mmol) in methanol (50 mL) was added Raney Ni (20% wt). To this mixtures was added hydrazine hydrate (10 mL) dropwise at room temperature. The reaction mixture was stirred at room temperature for 30 minutes. Raney Ni was filtered off through celite; the filtrate was dried in vacuo and purified with chromatography column on silica gel to afford the title compound as white solid.

1HNMR (400 MHz, DMSO-d6): δ ppm 2.78 (d, J=5.2 Hz, 3H), 5.20 (q, 1H), 5.77 (s, 2H), 6.82 (s, 1H), 7.53 (s, 1H); 19FNMR (376 MHz, DMSO-d6): δ ppm −45.49 (s, 3F); ESI-MS(+): 224 (M+H)+.

Step C: Methyl 3,6-dichloropyridine-2-carboxylate

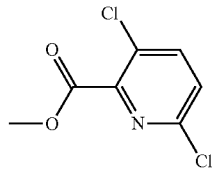

To a solution of 3,6-dichloropyridine-2-carboxylic acid (76.8 g, 0.4 mol) in methanol (500 mL) was added SOCl2 (150 ml) dropwise at room temperature. The reaction mixture was stirred at room temperature for 3 hours. After this time, the reaction mixture was poured into water and extracted with ethyl acetate three times. The combined organic layers were dried over sodium sulfate, filtered and concentrated in vacuo to give the title compound.

1HNMR (400 MHz, DMSO-d6): δ ppm 3.90 (s, 3H), 7.80 (d, J=8.8 Hz, 1H), 8.20 (d, J=8.8 Hz, 1H); ESI-MS(+): 228 (M+Na)+.

Step D: Methyl 6-chloro-3-ethylsulfanyl-pyridine-2-carboxylate

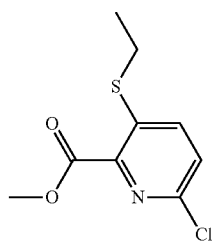

To a solution of methyl 3,6-dichloropyridine-2-carboxylate (16 g, 77.6 mmol) in DMF (150 mL) was added sodium ethanethiolate (7.2 g, 85.8 mmol) at 0° C. After the addition, the reaction mixture was stirred at room temperature for 30 min. LCMS analysis after this time showed reaction completion. The reaction mixture was poured into water, and precipitate formed filtered and dried under an infrared oven to afford the title compound as white solid.

1HNMR (400 MHz, CDCl3): δ ppm 1.38 (t, 3H), 2.92 (q, 2H), 3.98 (s, 3H), 7.40 (d, J=8.8 Hz, 1H), 7.66 (d, J=8.8 Hz, 1H); ESI-MS(+): 254 (M+Na)+.

Step E: Methyl 6-chloro-3-ethylsulfonyl-pyridine-2-carboxylate

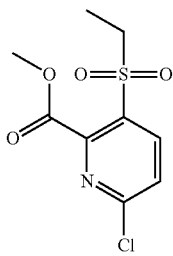 [SMILES: CCS(=O)(=O)c1ccc(Cl)nc1C(=O)OC]

A solution of methyl 6-chloro-3-ethylsulfanyl-pyridine-2-carboxylate (11.55 g, 50 mmol) and m-CPBA (25.8 g, 150 mmol) in 200 ml of dichloromethane was stirred at room temperature for 2 hours. After this time, the mixture was poured into a saturated solution of NaHCO$_3$ and Na$_2$SO$_3$, and extracted with DCM three times. The combined organic layers were dried over sodium sulfate, filtered and concentrated in vacuo The crude product was purified by column chromatography on silica gel to give the title compound.

1HNMR (400 MHz, CDCl3): δ ppm 1.33 (t, 3H), 3.51 (q, 2H), 4.02 (s, 3H), 7.63 (d, J=8 Hz, 1H), 8.29 (d, J=8 Hz, 1H); ESI-MS(+): 286 (M+Na)+.

Step F: Methyl 3-ethylsulfonyl-6-pyrimidin-2-yl-pyridine-2-carboxylate

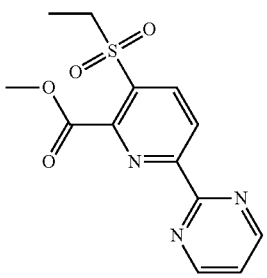 [SMILES: CCS(=O)(=O)c1ccc(-c2ncccn2)nc1C(=O)OC]

To a stirred solution of methyl 6-chloro-3-ethylsulfonyl-pyridine-2-carboxylate (526 mg, 2 mmol) and tributyl(pyrimidin-2-yl)stannane (1.107 g, 3 mmol) in dioxane (25 mL) were added CuI (76 mg, 0.4 mmol) and PdCl2(PPh3)2 (140 mg, 0.2 mmol). The reaction mixture was refluxed under an nitrogen atmosphere at 120° C. for 4 hours. After cooling to room temperature, the reaction mixture was filtered and concentrated in vacuo. The crude product was purified by column chromatography on silica gel to give the title compound.

1HNMR (400 MHz, CDCl3): δ ppm 1.36 (t, 3H), 3.58 (q, 2H), 4.05 (s, 3H), 7.42 (t, 1H), 8.53 (d, J=8.4 Hz, 1H), 8.81 (d, J=8.4 Hz, 1H), 9.00 (d, J=4.8 Hz, 2H); ESI-MS(+): 330 (M+Na)+

Step G: 3-ethylsulfonyl-6-pyrimidin-2-yl-pyridine-2-carboxylic acid

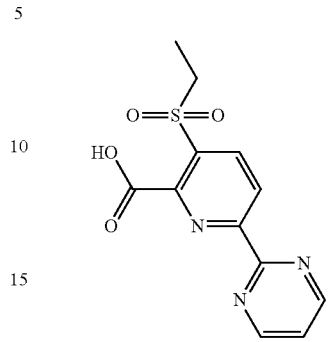

To a stirred solution of methyl 3-ethylsulfonyl-6-pyrimidin-2-yl-pyridine-2-carboxylate (522 mg, 1.7 mmol) in tetrahydrofurane (10 mL) was added NaOH (340 mg, 8.5 mmol) and water (30 ml). The reaction system was stirred at room temperature for 2 hours, by which time LCMS analysis showed reaction completion. The pH value was adjusted to 2 with HCl, and the reaction mixture was extracted with ethyl acetate three times. The organic layers were dried over anhydrous sodium sulfate, filtered and concentrated in vacuo to give the title compound.

1HNMR (400 MHz, DMSO-d6): δ ppm 1.22 (t, 3H), 3.57 (q, 2H), 7.66 (m, 1H), 7.68 (d J=4.8 Hz, 1H), 8.55 (d, J=8.4 Hz, 1H), 8.70 (d, J=8.4 Hz, 1H), 9.07 (d, J=4.8 Hz, 2H).

Step H: 2-(3-ethylsulfonyl-6-pyrimidin-2-yl-2-pyridyl)-3-methyl-6-(trifluoromethylsulfanyl)imidazo[4,5-c]pyridine (Compound P10, Table P)

(Compound P 10, table P)

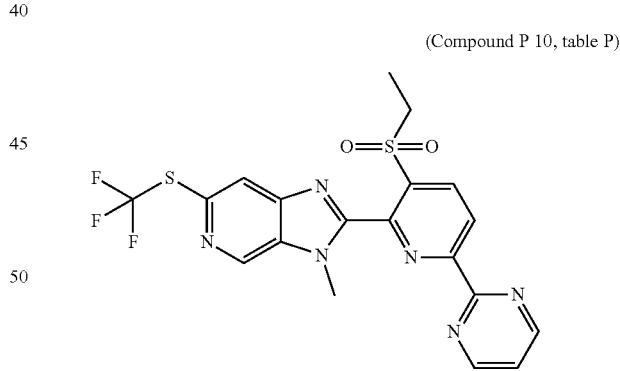

To a stirred solution of 3-ethylsulfonyl-6-pyrimidin-2-yl-pyridine-2-carboxylic acid (470 mg, 1.6 mmol), N3-methyl-6-(trifluoromethylsulfanyl)pyridine-3,4-diamine (430 mg, 1.92 mmol) and HATU (1.216 g, 3.2 mmol) in DMF (30 mL) was added DIPEA (2.8 ml, 16 mmol). The reaction system was stirred at room temperature overnight. After this time the reaction mixture was diluted with ethyl acetate and H$_2$O, and the organic layer washed with brine, dried over anhydrous sodium sulfate, and concentrated in vacuo. The crude product was used for the next step without further purification.

A solution of the crude product in acetic acid (20 mL) was refluxed at 120° C. for 24 h. The reaction mixture was evaporated to dryness and the residue purified by chromatography on silica gel to afford the title compound as white solid.

LCMS (method 1): 481 (M+H+); retention time: 0.93 min

1HNMR (400 MHz, CDCl3): δ (ppm) 1.38 (t, 3H), 3.80 (q, 2H), 3.93 (s, 3H), 7.44 (t, 1H), 8.10 (s, 1H), 8.70 (d, J=8.4 Hz, 1H), 8.96 (m, 2H), 9.0 (d, J=4.8 Hz, 2H); 19FNMR (376 MHz, CDCl3): δ (ppm) −45.77 (s, 3F);

Example H8: 2-(6-cyclopropyl-3-ethylsulfonyl-2-pyridyl)-3-methyl-6-(trifluoromethylsulfanyl)imidazo[4,5-c]pyridine (Compound P13, Table P)

(Compound P13, table P)

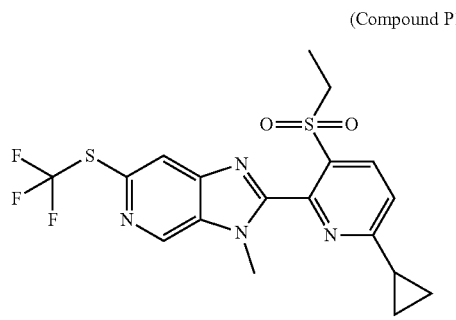

Step A: Methyl 6-cyclopropyl-3-ethylsulfanyl-pyridine-2-carboxylate

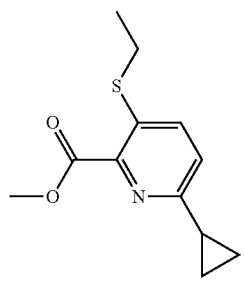 [SMILES: CCSc1ccc(C2CC2)nc1C(=O)OC]

To a stirred solution of methyl 6-chloro-3-ethylsulfanyl-pyridine-2-carboxylate (462 mg, 2 mmol), cyclopropylboronic acid (344 mg, 4 mmol) in dioxane (25 mL) was added potassium carbonate (552 mg, 4 mmol) and Pd(PPh3)4 (230 mg, 0.2 mmol). The reaction system was refluxed under an nitrogen atmosphere at 120° C. for 24 hours. After cooling to room temperature, the reaction mixture was filtered and concentrated in vacuo. The crude product was purified by column chromatography on silica gel to give the title compound.

1HNMR (400 MHz, CDCl3): δ (ppm) 0.98 (m, 4H), 1.32 (t, 3H), 2.08 (m, 1H), 2.88 (q, 2H), 3.95 (s, 3H), 7.08 (d, J=8.4 Hz, 1H), 7.57 (d, J=8 Hz, 1H); ESI-MS(+): 260 (M+Na)+.

Step B: 6-cyclopropyl-3-ethylsulfanyl-pyridine-2-carboxylic acid

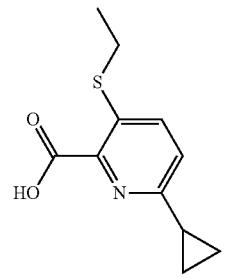

To a stirred solution of methyl 6-cyclopropyl-3-ethylsulfanyl-pyridine-2-carboxylate (320 mg, 1.35 mmol) in THF (10 mL) was added NaOH (280 mg, 7 mmol) and H2O (30 ml). The reaction system was stirred at room temperature for 4 hours. The pH value was adjusted to 2 with HCl, and the reaction mixture extracted with ethyl acetate three times. The combined organic layers dried over anhydrous sodium sulfate, filtered and concentrated in vacuo to give the title compound.

1HNMR (400 MHz, DMSO-d6): δ ppm 0.93 (m, 4H), 1.18 (t, 3H), 2.07 (m, 1H), 2.91 (q, 2H), 7.36 (d, J=8.0 Hz, 1H), 7.73 (d, J=8.4 Hz, 1H), 12.93 (bs, 1H); ESI-MS(−): 222 (M−H)−.

Step C: 6-bromo-2-(6-cyclopropyl-3-ethylsulfanyl-2-pyridyl)-3-methyl-imidazo[4,5-c]pyridine

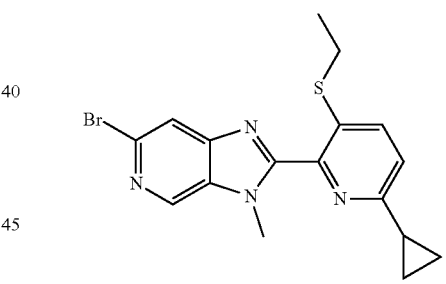

To a stirred solution of 6-cyclopropyl-3-ethylsulfanyl-pyridine-2-carboxylic acid (280 mg, 1.25 mmol), 6-bromo-N3-methyl-pyridine-3,4-diamine (303 mg, 1.5 mmol) and HATU (0.78 g, 2 mmol) in DMF (30 mL) was added DIPEA (2 ml, 10 mmol). The reaction mixture was stirred at room temperature overnight. The reaction mixture was then diluted with ethyl acetate and H2O, and the organic layer washed with brine, dried over anhydrous sodium sulfate, filtered and concentration in vacuo. The crude product was used for the next step without further purification. A solution of the crude product in acetic acid (20 mL) was refluxed at 120° C. for 24 h. The reaction mixture was concentrated, and purified by column chromatography on silica gel and purified to afford the title compound as white solid.

1HNMR (400 MHz, CDCl3): δ (ppm) 1.04 (m, 4H), 1.31 (t, 3H), 2.1 (m, 1H), 2.91 (q, 2H), 3.92 (s, 3H), 7.25 (d, J=8.4 Hz, 1H), 7.66 (d, J=8 Hz, 1H), 7.94 (s, 1H), 8.62 (s, 1H); ESI-MS(+): 413 (M+Na)+.

Step D: 6-bromo-2-(6-cyclopropyl-3-ethylsulfonyl-2-pyridyl)-3-methyl-imidazo[4,5-c]pyridine (Compound P12, Table P)

(Compound P12, table P)

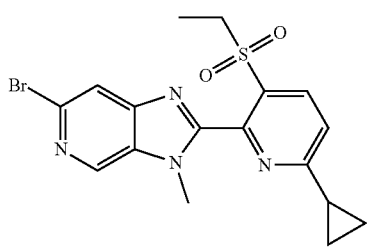

A sample of 6-bromo-2-(6-cyclopropyl-3-ethylsulfanyl-2-pyridyl)-3-methyl-imidazo[4,5-c]pyridine (285 mg, 0.73 mmol) and m-CPBA (630 mg, 3.66 mmol) in 40 ml of DCM was stirred at room temperature for 2 hours. Then the mixture was poured into a saturated solution of NaHCO$_3$ and Na$_2$SO$_3$ in water, and extracted with dichloromethane three times. The combined organic layers were dried over sodium sulfate, filtered and concentrated in vacuo. The crude product was purified by column chromatography on silica gel to give the title compound.

LCMS (method 1): 421/423 (M+H$^+$); retention time: 0.97 min

1HNMR (400 MHz, CDCl3): δ (ppm) 1.16 (m, 4H), 1.34 (t, 3H), 2.05 (m, 1H), 3.69 (q, 2H), 3.76 (s, 3H), 7.53 (d, J=8.0 Hz, 1H), 7.86 (s, 1H), 8.30 (d, J=8.4 Hz, 1H), 8.66 (s, 1H);

Step E: 2-(6-cyclopropyl-3-ethylsulfonyl-2-pyridyl)-3-methyl-6-(trifluoromethylsulfanyl)imidazo[4,5-c]pyridine (Compound P13, Table P)

(Compound P13, table P)

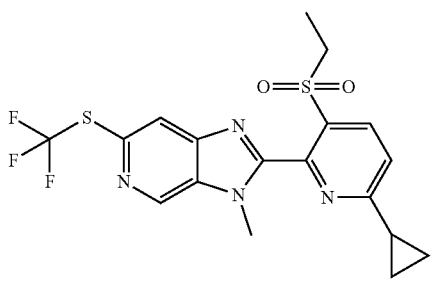

A sample of (bpy)CuSCF3 (410 mg, 1.28 mmol) and 6-bromo-2-(6-cyclopropyl-3-ethylsulfonyl-2-pyridyl)-3-methyl-imidazo[4,5-c]pyridine (270 mg, 0.64 mmol) in 20 ml of CH3CN was refluxed for 48 hours under nitrogen. The reaction mixture was removed from the oil bath and allowed to cool, and filtered through SiO2, eluting with diethyl ether. The filtrate was washed with brine, and concentrated in vacuo. The residue was purified by silica gel column chromatography to give the title compound.

LCMS (method 1): 444 (M+H$^+$); retention time: 1.07 min

1HNMR (400 MHz, CDCl3): δ (ppm) 1.19 (m, 4H), 1.34 (t, 3H), 2.12 (m, 1H), 3.71 (q, 2H), 3.81 (s, 3H), 7.54 (d, J=8.4 Hz, 1H), 8.10 (s, 1H), 8.31 (d, J=8.8 Hz, 1H), 8.92 (s, 1H)

Example H9: 6-(6-cyclopropyl-3-ethylsulfanyl-2-pyridyl)-7-methyl-3-(trifluoromethyl)imidazo[4,5-c]pyridazine (Compound P22, Table P)

(Compound P22, table P)

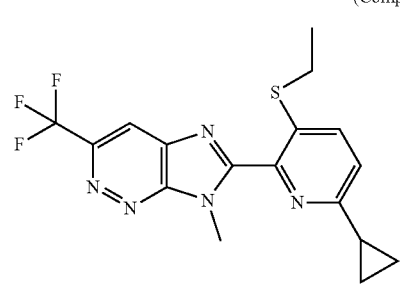

Step A: 3-chloro-6-iodopyridazine

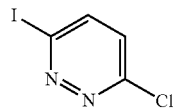

Hydriodic acid (250 mL) was added to a mixture of 3,6-dichloropyridazine (149 g, 1 mol) and NaI (180 g, 1.2 mol) in 500 mL of CHCl$_3$. After the addition, the mixture was stirred at ambient temperature for 24 h, and poured into water and extracted with dichloromethane three times. The combined organic layers were dried over sodium sulfate, filtered and concentrated in vacuo to give the title compound.

$^1$H-NMR (400 Mz, DMSO-d$_6$) δ: 7.63 (d, 1H), 8.16 (d, 1H).

Step B: 3-chloro-6-(trifluoromethyl)pyridazine

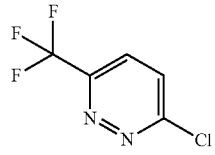 [SMILES: FC(F)(F)c1ccc(Cl)nn1]

TMSCF$_3$ (198.8 g, 1.4 mol) was added to a mixture of 3-chloro-6-iodopyridazine (240 g, 1 mol), KF (81 g, 1.4 mol) and CuI (228 g, 1.2 mol) in 1 L of DMF under nitrogen. After the addition, the mixture was stirred at 50° C. for 2 h. The mixture was then poured into water and extracted with ether (three times). The combined organic layers were dried over sodium sulfate, filtered and concentrated in vacuo. The residue was purified by flash column chromatography on silica gel to give the title compound.

$^1$H-NMR (400 Mz, DMSO-d$_6$) δ: 8.30 (d, 1H), 8.38 (d, 1H); $^{19}$F-NMR (400 Mz, DMSO-d$_6$) δ: −64.93 (s, 3F).

Step C:
N-methyl-6-(trifluoromethyl)pyridazin-3-amine

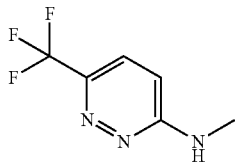

A solution of MeNH₂ (100 g, 30% in EtOH) was added to a mixture of 3-chloro-6-(trifluoromethyl) pyridazine (91 g, 0.5 mol) in 100 ml of EtOH. After the addition, the mixture was stirred at 50° C. for 2 hours and then poured into water. The precipitated solid was filtered and dried in vacuum to give the title compound $^1$H-NMR (400 Mz, DMSO-d$_6$) δ: 2.93 (d, 3H), 6.95 (d, 1H), 7.58 (q, 1H), 7.63 (d, 1H); $^{19}$F-NMR (400 Mz, DMSO-d$_6$) δ: −59.88 (s, 3F); ESI-MS(+): 178 (M+H)⁺.

Step D: 4-bromo-N-methyl-6-(trifluoromethyl) pyridazin-3-amine

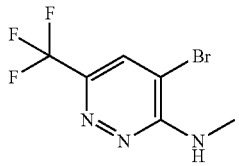

Bromine (32 g, 0.2 mol) was added to a mixture of N-methyl-6-(trifluoromethyl) pyridazin-3-amine (17.7 g, 0.1 mol) in 100 mL of MeCN. After the addition, the mixture was stirred at ambient temperature for 48 hours. After this time, the mixture was poured into ammonium hydroxide (10% solution) and extracted with ethyl acetate (three times). The combined organic layers were dried over sodium sulfate, filtered and concentrated in vacuo. The residue was purified by flash column chromatography on silica gel to give the title compound.

$^1$H-NMR (400 Mz, DMSO-d$_6$) δ: 3.03 (d, 3H), 7.45 (q, 1H), 8.23 (s, 1H); $^{19}$F-NMR (400 Mz, DMSO-d$_6$) δ: −59.47 (s, 3F); ESI-MS(+): 256/258 (M+H)⁺.

Step E: N³-methyl-6-(trifluoromethyl)pyridazine-3,4-diamine

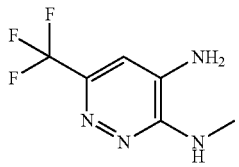

4-Bromo-N-methyl-6-(trifluoromethyl)pyridazin-3-amine (3 g, 11.8 mmol) and 120 mL of ammonium hydroxide was placed in a 250 mL autoclave. Then, nitrogen gas was introduced to the autoclave and pressure was increased to 2 MPa. The mixture was stirred at 130° C. for 48 h, poured into water and extracted with ethyl acetate (three times). The combined organic layers were dried over sodium sulfate, filtered and concentrated in vacuo. The residue was purified by column chromatography on silica gel to give the title compound $^1$H-NMR (400 Mz, DMSO-d$_6$) δ: 297 (d, 3H), 6.27 (s, 2H), 6.50 (q, 1H), 6.67 (s, 1H); $^{19}$F-NMR (400 Mz, DMSO-d$_6$) δ: −61.96 (s, 3F); ESI-MS(+): 193 (M+H)⁺.

Step F:
6-cyclopropyl-3-ethylsulfanyl-pyridine-2-carbonyl chloride

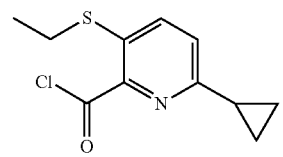

Oxalyl chloride (380 mg, 3 mmol) was added to a mixture of 6-cyclopropyl-3-ethylsulfanyl-pyridine-2-carboxylic acid (223 mg, 1 mmol) in 10 mL of dichloromethane and stirred at room temperature for 30 min. The excess oxalyl chloride and dichloromethane was removed under reduced pressure to give the title compound in almost quantitative yield (241 mg). The crude title compound was directly used for the next step without further purification.

Step G: 6-(6-cyclopropyl-3-ethylsulfanyl-2-pyridyl)-7-methyl-3-(trifluoromethyl)imidazo[4,5-c]pyridazine (Compound P22, Table P)

(Compound P22, table P)

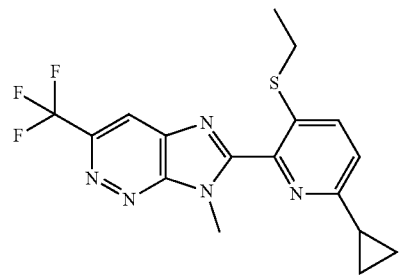

A sample of 6-cyclopropyl-3-ethylsulfanyl-pyridine-2-carbonyl chloride (241 mg, 1 mmol) was added to a mixture of N3-methyl-6-(trifluoromethyl) pyridazine-3,4-diamine (211 mg, 1.1 mmol) in 20 mL of THF and the mixture was reflux for 48 hours. After this time, the mixture was poured into water and extracted with ethyl acetate three times. The combined organic layers were dried over sodium sulfate, filtered and concentrated in vacuo. The crude product was purified by column chromatography on silica gel to give the title compound.

1H NMR (400 MHz, DMSO) δ 0.97-1.00 (m, 2H), 1.02-1.07 (m, 2H), 1.19 (t, 3H), 2.22-2.28 (m, 1H), 2.98 (q, 2H), 4.08 (s, 3H), 7.58 (d, 1H), 7.98 (d, 1H), 8.71 (s, 1H); 19F NMR (400 MHz, DMSO) δ −62.23 (s, 3F); ESI-MS(+): 380 (M+H)+, 434 (M+Na+MeOH)+.

Example H10: 6-(6-cyclopropyl-3-ethylsulfonyl-2-pyridyl)-7-methyl-3-(trifluoromethyl)imidazo[4,5-c]pyridazine (Compound P14, Table P)

(Compound P14, table P)

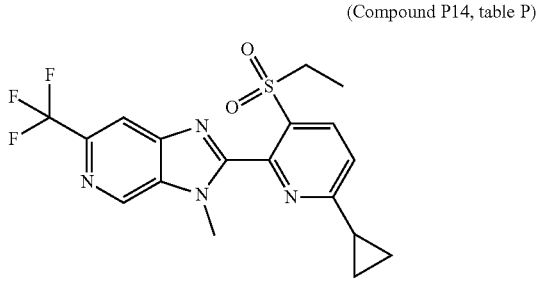 [SMILES: CCS(=O)(=O)c1ccc(C2CC2)nc1-c1nc2cc(C(F)(F)F)ncc2n1C]

A solution of 6-(6-cyclopropyl-3-ethylsulfanyl-2-pyridyl)-7-methyl-3-(trifluoromethyl)imidazo[4,5-c]pyridazine (70 mg, 0.18 mmol) and m-CPBA (93 mg, 0.54 mmol) in 10 ml of dichloromethane was stirred at room temperature for 2 hours. The mixture was then poured into a saturated solution of NaHCO$_3$ and Na$_2$SO$_3$ in water, and extracted with ethyl acetate three times. The combined organic layers were dried over sodium sulfate, filtered and concentrated in vacuo. The crude product was purified by column chromatography on silica gel to give the title compound.

LCMS (method 1): 413 (M+H$^+$); retention time: 1.01 min.

1H NMR (400 MHz, DMSO-d6) δ 1.05-1.07 (m, 2H), 1.13-1.18 (m, 2H), 1.15 (t, 3H), 2.38-2.42 (m, 1H), 3.63 (q, 2H), 3.88 (s, 3H), 7.88 (d, 1H), 8.34 (d, 1H), 8.72 (s, 1H); 19F-NMR (400 Mz, DMSO-d6) δ: −64.55 (s, 3F);

Example H11: 2-[5-ethylsulfonyl-6-[3-methyl-6-(trifluoromethyl)imidazo[4,5-c]pyridin-2-yl]-2-pyridyl]acetonitrile (Compound P23, Table P)

(Compound P23, table P)

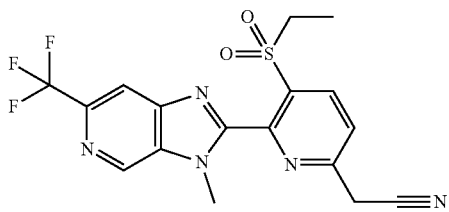

In a microwave vial 2-(6-chloro-3-ethylsulfonyl-2-pyridyl)-3-methyl-6-(trifluoromethyl)imidazo[4,5-c]pyridine (0.20 g, 0.49 mmol) was dissolved in DMF (1.0 mL). The vial was flushed with argon and TMSCN (0.10 mL, 0.74 mmol), difluorozinc (0.031 g, 0.30 mmol), Pd$_2$(dba)$_3$ (0.0091 g, 0.0099 mmol) and XANTPHOS (0.012 g, 0.020 mmol) were added. The vial was capped and heated in the microwave at 140° C. for 30 min. The reaction mixture was diluted with ethyl acetate and filtered over hyflo. The filtrate was extracted with water and brine, dried over Na$_2$SO$_4$, filtered and concentrated in vacuo. The crude product was purified by flash chromatography on silica gel to give the title compound.

LCMS (method 1): 410 (M+H+); retention time: 0.84 min.

1H NMR (400 MHz, CHLOROFORM-d) δ ppm 1.40 (t, J=7.52 Hz, 3H) 3.83 (q, J=7.34 Hz, 2H) 3.97 (s, 3H) 4.17 (s, 2H) 7.89 (d, J=8.44 Hz, 1H) 8.15 (s, 1H) 8.63 (d, J=8.07 Hz, 1H) 9.04 (s, 1H)

Example H12: 1-[5-ethylsulfonyl-6-[3-methyl-6-(trifluoromethyl)imidazo[4,5-c]pyridin-2-yl]-2-pyridyl]cyclopropanecarbonitrile (Compound P17, Table P)

(Compound P17, table P)

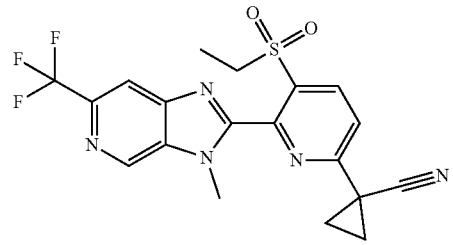 [SMILES: CCS(=O)(=O)c1ccc(C2(C#N)CC2)nc1-c1nc2cc(C(F)(F)F)ncc2n1C]

A sample of 2-[5-ethylsulfonyl-6-[3-methyl-6-(trifluoromethyl)imidazo[4,5-c]pyridin-2-yl]-2-pyridyl]acetonitrile (0.11 g, 0.27 mmol) was dissolved in acetonitrile (2.8 mL). Cesium carbonate (0.27 g, 0.81 mmol) was added followed by adding 1,2-dibromoethane (0.047 mL, 0.54 mmol). The mixture was stirred at 80° C. for 1 hour. LC-MS analysis showed consumption of the starting material and mass of desired product. The reaction was quenched with water and acetonitrile and the evaporated. The residue was diluted with ethyl acetate washed with water and brine, dried over Na$_2$SO$_4$, filtered and concentrated in vacuo. The crude product was purified by flash chromatography on silica gel to give the title compound LCMS (method 1): 436 (M+H+); retention time: 0.94 min.

1H NMR (400 MHz, CHLOROFORM-d) δ ppm 1.38 (t, J=7.52 Hz, 3H) 1.88-2.02 (m, 4H) 3.73 (d, J=7.70 Hz, 2H) 3.86 (s, 3H) 8.12-8.19 (m, 2H) 8.54 (d, J=8.44 Hz, 1H) 9.02 (s, 1H)

Example H13: 2-[3-ethylsulfonyl-6-[2-(3-fluorophenyl)ethynyl]-2-pyridyl]-3-methyl-6-(trifluoromethyl)imidazo[4,5-c]pyridine (Compound P20, Table P)

(Compound P20, table P)

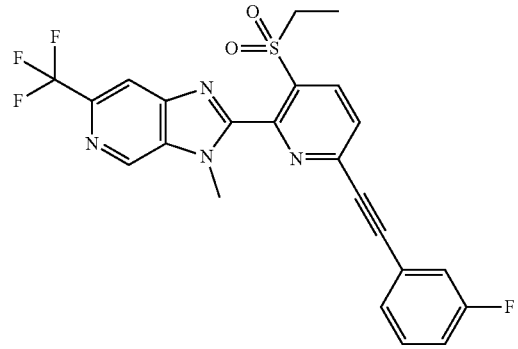

A sample of 2-(6-chloro-3-ethylsulfonyl-2-pyridyl)-3-methyl-6-(trifluoromethyl)imidazo[4,5-c]pyridine (0.10 g, 0.25 mmol), 1-ethynyl-3-fluoro-benzene (0.044 mL, 0.37 mmol), DIPEA (0.086 mL, 0.49 mmol), copper(I)iodide (0.0024 g, 0.012 mmol) in tetrahydrofurane (4.0 mL) were mixed in a vial and the clear, pale yellow solution was flushed with argon. PdCl$_2$(PPH$_3$)$_2$ (0.0088 g, 0.012 mmol) was added and the mixture was stirred at room temperature overnight. Reaction after this time showed completion. The crude mixture was purified by flash chromatography to give the title compound as a beige solid.

LCMS (method 1): 489 (M+H$^+$); retention time: 1.11 min.
$^1$H NMR (400 MHz, CHLOROFORM-d) δ ppm 1.39 (t, J=7.34 Hz, 3H) 3.78 (q, J=7.46 Hz, 2H) 3.96 (s, 3H) 7.14-7.24 (m, 1H) 7.32-7.38 (m, 1H) 7.37-7.48 (m, 2H) 7.92 (d, J=8.44 Hz, 1H) 8.14 (s, 1H) 8.54 (d, J=8.44 Hz, 1H) 9.02 (s, 1H)

Compounds in tables 1-88 can be prepared analogously to the methods described above.

TABLE P

Examples of compounds of formula (I)

| Compound No. | Compound | Melting Point | MS/NMR |
|---|---|---|---|
| P1 | | 255-256 | LCMS (method 1): 481/483 (M + H)$^+$ R$_t$ = 1.11 min |
| P2 | | — | LCMS (method 1): 541 (M + H)$^+$ Rt = 1.14 min 1.14 min, (M + H) = 541 |
| P3 | | 261-263 | LCMS (method 1): 505 (M + H)$^+$ R$_t$ = 1.07 min |

TABLE P-continued

Examples of compounds of formula (I)

| Compound No. | Compound | Melting Point | MS/NMR |
|---|---|---|---|
| P4 | | 140-142 | LCMS (method 1): 583 (M + H)+ R$_t$ = 1.17 min |
| P5 | | 170-172 | LCMS (method 1): 583 (M + H)+ R$_t$ = 1.17 min |
| P6 | | 118-128 | LCMS (method 1): 549/551 (M + H)+ R$_t$ = 1.14 min |
| P7 | | 289-291 | LCMS (method 1): 533/535/537 (M + H)+ R$_t$ = 1.20 min |

TABLE P-continued

Examples of compounds of formula (I)

| Compound No. | Compound | Melting Point | MS/NMR |
|---|---|---|---|
| P8 | | 223-225 | LCMS (method 1): 483 (M + H)⁺ R$_t$ = 1.10 min |
| P9 | | 201-202 | LCMS (method 1): 537 (M + H)⁺ R$_t$ = 1.17 min |
| P10 | | 180-181 | LCMS (method 1): 481 (M + H)⁺ R$_t$ = 0.93 min |
| P11 | | 200-201 | LCMS (method 1): 503/505 (M + H)⁺ R$_t$ = 1.14 min |

TABLE P-continued

Examples of compounds of formula (I)

| Compound No. | Compound | Melting Point | MS/NMR |
|---|---|---|---|
| P12 | | 194-195 | LCMS (method 1): 421/423 (M + H)+ R$_t$ = 0.97 min |
| P13 | | 130-131 | LCMS (method 1): 444 (M + H)+ R$_t$ = 1.07 |
| P14 | | 150-152 | LCMS (method 1): 444 (M + H)+ R$_t$ = 1.01 min |
| P15 | | 185-187 | LCMS (method 1): 413 (M + H)+ R$_t$ = 1.01 min |
| P16 | | — | LCMS (method 1): 438 (M + H)+ R$_t$ = 0.86 min |

TABLE P-continued

Examples of compounds of formula (I)

| Compound No. | Compound | Melting Point | MS/NMR |
|---|---|---|---|
| P17 | | — | LCMS (method 1): 436 (M + H)+ R$_t$ = 0.95 min |
| P18 | | — | LCMS (method 1): 465 (M + H)+ R$_t$ = 1.07 min |
| P19 | | — | LCMS (method 1): 507 (M + H)+ R$_t$ = 1.12 min |
| P20 | | — | LCMS (method 1): 489 (M + H)+ R$_t$ = 1.10 min |

TABLE P-continued

Examples of compounds of formula (I)

| Compound No. | Compound | Melting Point | MS/NMR |
|---|---|---|---|
| P21 | 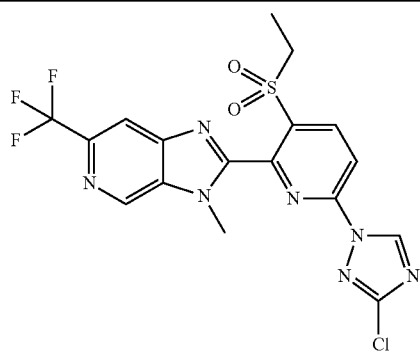 | — | LCMS (method 1): 472/474 (M + H)⁺ R_t = 0.94 min |
| P22 | 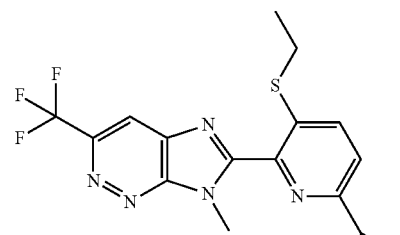 | — | 1H NMR (400 MHz, DMSO) δ 0.97-1.00 (m, 2H), 1.02-1.07 (m, 2H), 1.19 (t, 3H), 2.22-2.28 (m, 1H), 2.98 (q, 2H), 4.08 (s, 3H), 7.58 (d, 1H), 7.98 (d, 1H), 8.71 (s, 1H |
| P23 | 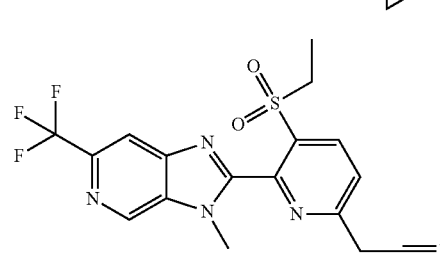 | | LCMS (method 1): 410 (M + H)⁺ R_t = 0.84 min |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 88 and P of the present invention"):

an adjuvant selected from the group of substances consisting of petroleum oils (628)+TX,
an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50,439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure B, (839)+TX, trimedlure B2 (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis (4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3, 5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+

TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX; and microbials including: *Acinetobacter iwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain I-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera nucleopolyhedrovirus* (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium*

*longisporum* (Vertiblast®)+TX, *Lecanicillium muscarium* (Vertikil®)+TX, *Lymantria dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacffius polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (SpotLess Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. Poae (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near ambrosioides (Requiem®)+TX, Chrysanthemum extract (Crisant®)+TX, extract of neem oil (Trilogy®)+TX, essentials oils of Labiatae (Botania®)+TX, extracts of clove rosemary peppermint and thyme oil (Garden insect killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable pheromone®)+TX, Peachtree Borer Pheromone (Isomate-P®)+TX, Tomato Pinworm Pheromone (3M Sprayable pheromone®)+TX, Entostat powder (extract from palm tree) (Exosex CM®)+TX, (E+TX,Z+TX,Z)-3+TX,8+TX,11 Tetradecatrienyl acetate+TX, (Z+TX, Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline cucumeris®)+TX, *Amblyseius fallacis* (Fallacis®)+TX, *Amblyseius swirskii* (Bugline swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (Encarsia max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus califomicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Online i®)+TX, *Orius laevigatus* (Thripor-L®+TX, Oriline I®)+TX, *Orius majusculus* (Oriline m®)+TX, *Orius strigicoffis* (Thripor-S®)+TX, *Pauesia juniperorum*+TX, *Pediobius foveolatus*+TX, *Phasmarhabditis hermaphrodita* (Nemaslug®)+TX, *Phymastichus coffee*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline sf®+TX, Scia-rid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Growers Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassium thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprote.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used. CAS Reg. No" means the Chemical Abstracts Registry Number.

The active ingredient mixture of the compounds of formula I selected from Tables 1 to 88 and P with active ingredients described above comprises a compound selected from Tables 1 to 88 and P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 88 and P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 88 and P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1: *Bemisia tabaci* (Cotton White Fly): Feeding/Contact Activity

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation. The following compounds resulted in at least 80% mortality at an application rate of 200 ppm: P9, P13 and P14.

Example B2: *Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation. The following compounds gave an effect of at least 80% in at least one of the two categories (mortality or growth inhibition) at an application rate of 200 ppm: P1, P2, P3, P4, P5, P6, P7, P8, P9, P10, P11, P12, P13, P14, and P15.

Example B3: *Euschistus heros* (Neotropical Brown Stink Bud)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation. The following compounds gave an effect of at least 80% in at least one of the two categories (mortality or growth inhibition) at an application rate of 200 ppm:
P1, P3, P8, P9, P10, P13, P14, and P15

Example B4: *Myzus persicae* (Green Peach Aphid): Feeding/Contact Activity

Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation. The following compounds resulted in at least 80% mortality at an application rate of 200 ppm: P10, P13, P14 and P15.

Example B5: *Myzus persicae* (Green Peach Aphid). Systemic Activity

Roots of pea seedlings infested with an aphid population of mixed ages were placed directly into aqueous test solutions prepared from 10,000 DMSO stock solutions. The samples were assessed for mortality 6 days after placing seedlings into test solutions. The following compound resulted in at least 80% mortality at a test rate of 24 ppm: P10.

Example B6: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation. The following compounds gave an effect of at least 80% in at least one of the two categories (mortality or growth inhibition) at an application rate of 200 ppm: P1, P2, P3, P4, P6, P8, P9, P10, P11, P12, P13, P14 and P15.

Example B7: *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample. The following compounds resulted in at least 80% control at an application rate of 200 ppm: P1, P2, P3, P4, P5, P6, P8, P9, P10, P11, P12, P13, P14, and P15.

Example B8: *Spodoptera littoralis* (Egyptian Cotton Leaf Worm) Systemic Activity Test compounds were applied by pipette from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation. The following compounds gave an effect of at least 80% in at least one of the three categories (mortality, anti-feeding, or growth inhibition) at a test rate of 12.5 ppm:

P10, P13, P14 and P15.

Example B9: *Tetranychus urticae* (Two-Spotted Spider Mite): Feeding/Contact Activity Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation. The following compounds resulted in at least 80% mortality at an application rate of 200 ppm: P10 and P13.

Example B10: *Thrips tabaci* (Onion Thrips) Feeding/Contact Activity

Sunflower leaf discs were placed on agar in 24-well microtiter plates and sprayed with aqueous test solutions prepared from 10,000 ppm DMSO stock solutions. After drying the leaf discs were infested with a thrips population of mixed ages. The samples were assessed for mortality 6 days after infestation. The following compounds resulted in at least 80% mortality at an application rate of 200 ppm: P3 and P10.

Example B11: *Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction. The following compounds gave at least 80% control of *Aedes aegypti* after 48 h and/or 24 h: P9, P10, P11, P13, P14 and P15.

Example B12: *Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction. The following compounds gave at least 80% control of *Anopheles stephensi* after 48 h and/or 24 h: P10 and P13.

Comparative Example

Prior art compound: Compound V12.03 described on page 196 of WO 2015/000715:

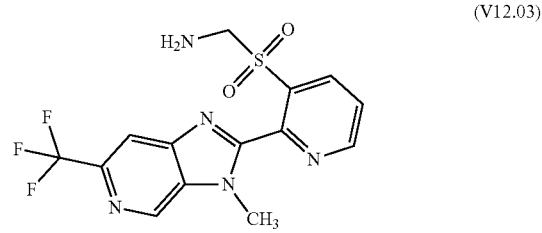 [SMILES: Cn1c(-c2ncccc2S(=O)(=O)CN)nc2cc(C(F)(F)F)ncc21]

(V12.03)

Compounds of this Invention:

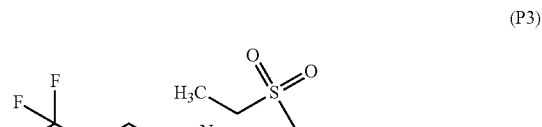

(P3)

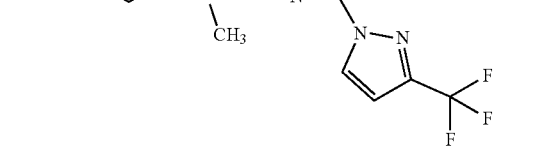

(P1)

The compounds V12.03, P1 and P3 are structurally identical except for the substitution pattern at the pyridine moiety. The pyridine moiety of the prior art compound V12.03 is unsubstituted, the compounds P1 and P3 of this invention are substituted by a pyrazole and phenyl group respectively at the 6-position of the pyridine ring. The pyrazole group is substituted by trifluoromethyl and the phenyl group is substituted by chloro.

Example B13

Insecticidal action against *Diabrotica balteata* (Corn root worm), *Plutella xylostella* (Diamond black moth), and *Spodoptera littoralis* (Egyptian cotton leaf worm). The tests were carried out as described in biological examples B2, B6 and B7, respectively, with the larval feeding/contact activity being reported as Breakpoint ($BP_{80}$) values in parts per million (i.e. the lowest concentration which gives 80% larval mortality).

TABLE B13

Insecticidal action against *Diabrotica balteata* (Corn root worm), *Plutella xylostella* (Diamond black moth), and *Spodoptera littoralis* (Egyptian cotton leaf worm).

| Compound No. | Compound | BP$_{80}$ Values in ppm | | |
|---|---|---|---|---|
| | | *Diabrotica balteata* | *Plutella xylostella* | *Spodoptera littoralis* |
| V12.03 | 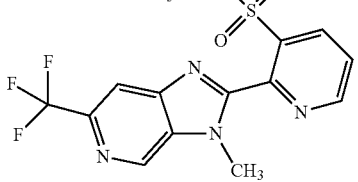 | 16 | 250 | 250 |
| P1 | 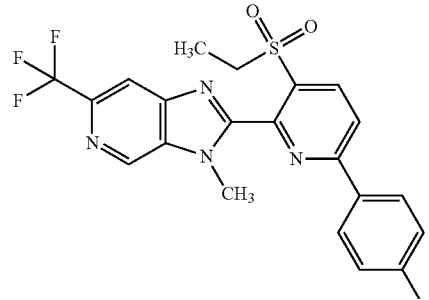 | 3 | 12 | 12 |
| P3 | 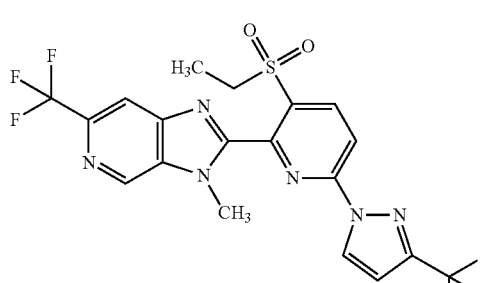 | 0.8 | 12 | 0.8 |

As is evident from Table B13, the compounds P1 and P3 according to this invention show a superior insecticidal action against *Diabrotica balteata* (Corn root worm), *Plutella xylostella* (Diamond black moth), and *Spodoptera littoralis* (Egyptian cotton leaf worm) compared to compound V12.03 of the prior art.

This surprising enhancement of insecticidal activity was not to be expected in view of the close structural similarity of these compounds.

Example B14: Comparison of the Insecticidal Activity of Compounds of this Invention with the Prior Art In order to demonstrate the surprising increase in insecticidal activity in comparison with the prior art, the insecticidal activity of the following compounds have been tested:

Prior art compound: Compound V12.01 described on page 196 of WO 2015/000715:

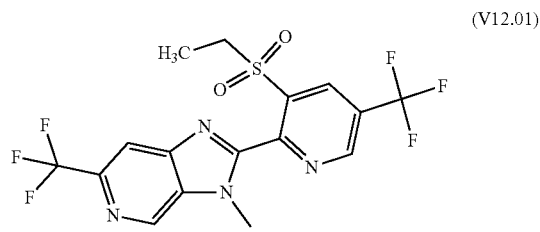 [SMILES: CCS(=O)(=O)c1cc(C(F)(F)F)cnc1-c1nc2cc(C(F)(F)F)ncc2n1C]

(V12.01)

Compounds of this Invention:

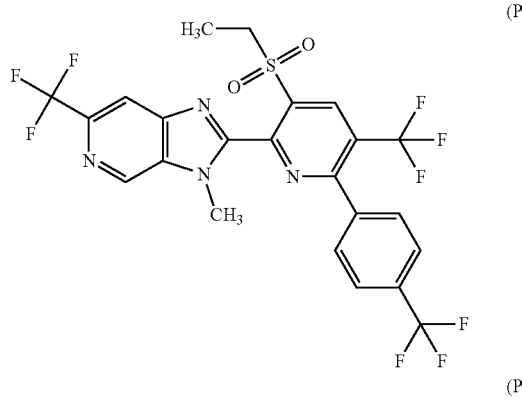

(P4)

(P5)

The compounds V12.01, P4 and P5 are structurally identical except for the substitution pattern at the pyridine moiety. The pyridine moiety of the prior art compound V12.03 is unsubstituted at the 6-position, the compounds P1 and P3 of this invention are substituted by a phenyl moiety at the 6-position of the pyridine moiety. The phenyl moiety is substituted by trifluoromethyl at the 3- and 4-position respectively. In all three compounds, the 5-position of the pyridine moiety is substituted by trifluoromethyl.

Example B14

Insecticidal action against *Diabrotica balteata* (Corn root worm). The test were carried out as described in biological example B6 with the larval feeding contact activity being reported as Breakpoint ($BP_{80}$) values in parts per million (i.e. the lowest concentration which gives 80% larval mortality).

TABLE B14

Insecticidal action against *Diabrotica balteata* (Corn root worm).

| Compound No. | Compound | $BP_{80}$ Values in ppm *Diabrotica balteata* |
|---|---|---|
| V12.01 | 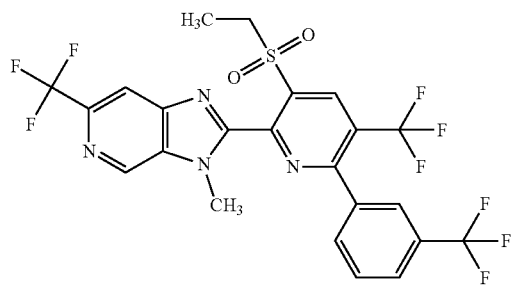 [SMILES: CCS(=O)(=O)c1cc(C(F)(F)F)c(-c2cccc(C(F)(F)F)c2)nc1-c1nc2cc(C(F)(F)F)ncc2n1C] | 16 |
| P4 |  | 10 |

TABLE B14-continued

Insecticidal action against *Diabrotica balteata* (Corn root worm).

| Compound No. | Compound | BP$_{80}$ Values in ppm *Diabrotica balteata* |
|---|---|---|
| P5 | 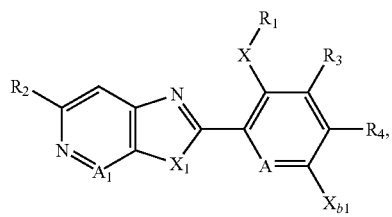 | 10 |

Table B14: Insecticidal Action Against

As is evident from Table B14, the compounds P4 and P5 according to this invention show a superior insecticidal action against *Diabrotica balteata* (Corn root worm) compared to compound V12.01 of the prior art.

This surprising enhancement of insecticidal activity was not to be expected in view of the close structural similarity of these compounds.

The invention claimed is:
1. A method comprising:
reacting a compound of Formula (II),

II wherein
Xb$_1$ is a leaving group, boron derived functional group, or trialkyl tin derivative;
A represents CH, N or the N-oxide;
A$_1$ is CH, N or the N-oxide;
X is S, SO or SO$_2$;
R$_1$ is C$_1$-C$_4$alkyl, C$_1$-C$_4$haloalkyl, C$_3$-C$_6$cycloalkyl, C$_3$-C$_6$cycloalkyl-C$_1$-C$_4$alkyl; or
R$_1$ is C$_3$-C$_8$cycloalkyl-C$_1$-C$_4$alkyl mono- or polysubstituted by substituents selected from the group consisting of halogen, cyano and C$_1$-C$_4$alkyl; or
R$_1$ is C$_2$-C$_8$alkenyl, C$_2$-C$_6$haloalkenyl or C$_2$-C$_8$alkynyl;
R$_2$ is halogen, cyano, C$_1$-C$_8$haloalkyl or C$_1$-C$_8$haloalkyl substituted by one or two substituents selected from the group consisting of hydroxyl, methoxy and cyano; or
R$_2$ is C$_1$-C$_4$haloalkylsulfanyl, C$_1$-C$_4$haloalkylsulfinyl, C$_1$-C$_4$haloalkylsulfonyl, O(C$_1$-C$_4$haloalkyl), or —C(O)C$_1$-C$_4$haloalkyl; or
R$_2$ is C$_3$-C$_8$cycloalkyl which can be mono- or polysubstituted by substituents selected from the group consisting of halogen, cyano and C$_1$-C$_4$alkyl;

X$_1$ is NR$_5$, wherein R$_5$ is hydrogen, C$_1$-C$_4$alkyl, C$_2$-C$_6$alkenyl, C$_2$-C$_6$alkynyl, C$_1$-C$_4$alkoxy-C$_1$-C$_4$alkyl or C$_3$-C$_6$cycloalkyl; or
X$_1$ is oxygen or sulfur;
R$_3$ is hydrogen or C$_1$-C$_2$-alkyl; and
R$_4$ is hydrogen, halogen or C$_1$-C$_3$haloalkyl,
with Yb$_1$-Q, Yb$_2$-Q, or a Q which contains an appropriate NH functionality,
wherein
Yb$_1$ is a boron-derived functional group or leaving group;
Yb$_2$ is a trialkyl tin derivative or leaving group; and
Q is phenyl which can be mono- or polysubstituted by substituents selected from the group consisting of halogen, cyano, C$_1$-C$_4$alkyl, C$_1$-C$_4$haloalkyl, C$_1$-C$_4$haloalkoxy, C$_1$-C$_4$alkoxy, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl; or
Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, C$_1$-C$_4$alkyl, C$_1$-C$_4$haloalkyl, C$_1$-C$_4$haloalkoxy, C$_1$-C$_4$alkoxy, C$_1$-C$_4$alkylsulfanyl, C$_1$-C$_4$alkylsulfinyl, C$_1$-C$_4$alkylsulfonyl, —C(O)C$_1$-C$_4$alkyl, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl; or
Q is a five- to six-membered, aromatic, partially saturated or fully saturated ring system linked via a nitrogen atom to the ring which contains the group A, said ring system contains 1, 2 or 3 heteroatoms selected from the group consisting of nitrogen, oxygen and sulphur, with the proviso that said ring system cannot contain more than one oxygen atom and more than one sulfur atom and can be mono- or polysubstituted by substituents selected from the group consisting of halogen, cyano, C$_1$-C$_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl;

Q is $C_3$-$C_6$cycloalkyl, or $C_3$-$C_6$cycloalkyl mono- or polysubstituted by substituents selected from the group consisting of halogen, cyano, $CONH_2$, carboxyl, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl; or Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl; or Q is $C_1$-$C_6$alkyl, or $C_1$-$C_6$alkyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl;

to form a compound of formula (I)

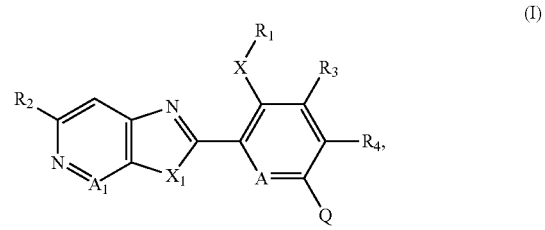

wherein $R_1$, $R_2$, $R_3$, $R_4$, A, $A_1$, X, $X_1$, and Q are as defined above;

with the proviso that:
when $Xb_1$ is a leaving group, $Yb_1$ is a boron-derived functional group and $Yb_2$ is a trialkyl tin derivative; and
when $X_{b1}$ is a boron derived functional group or trialkyl tin derivative, $Yb_1$ and $Yb_2$ are leaving groups or the reacting is not with the Q which contains an appropriate NH functionality.

2. The method of claim 1, wherein the reacting is with $Yb_1$-Q.

3. The method of claim 2, wherein $Yb_1$ is $B(OH)_2$ or $B(OR_{b1})_2$, wherein $R_{b1}$, is a $C_1$-$C_4$alkyl group or the two groups $OR_{b1}$ form together with the boron atom a five membered ring.

4. The method of claim 3, wherein reacting further comprises the presence of a palladium based catalyst, a base, and a solvent.

5. The method of claim 3, wherein the reacting is a Suzuki Reaction.

6. The method of claim 1, wherein the reacting is with $Yb_2$-Q.

7. The method of claim 6, wherein $Yb_2$ is tri-n-butyl tin.

8. The method of claim 7, wherein the reacting further comprises the presence of a palladium catalyst and inert solvent.

9. The method of claim 7, wherein the reacting is a Stille Reaction.

10. The method of claim 1, wherein the reacting is with Q which contains an appropriate NH functionality.

11. The method of claim 10, wherein the reacting is in the presence of a base.

12. The method of claim 11, wherein the reacting is in the presence of a copper catalyst and inert solvent.

* * * * *